US012667302B2

(12) United States Patent
Shimuta et al.

(10) Patent No.: US 12,667,302 B2
(45) Date of Patent: Jun. 30, 2026

(54) ORAL BODY DEVICE

(71) Applicant: Murata Manufacturing Co., Ltd.,
Nagaokakyo (JP)

(72) Inventors: Toru Shimuta, Nagaokakyo (JP);
Keisuke Danno, Nagaokakyo (JP);
Kouki Ejiri, Nagaokakyo (JP); Hideki
Ejima, Nagaokakyo (JP)

(73) Assignee: MURATA MANUFACTURING CO.,
LTD., Nagaokakyo (JP)

( * ) Notice: Subject to any disclaimer, the term of this
patent is extended or adjusted under 35
U.S.C. 154(b) by 903 days.

(21) Appl. No.: 17/969,973

(22) Filed: Oct. 20, 2022

(65) Prior Publication Data

US 2023/0045404 A1     Feb. 9, 2023

Related U.S. Application Data

(63) Continuation of application No.
PCT/JP2021/020466, filed on May 28, 2021.

(30) Foreign Application Priority Data

Jun. 19, 2020     (JP) ................................. 2020-106457

(51) Int. Cl.
*A61B 5/00* (2006.01)

(52) U.S. Cl.
CPC ........ *A61B 5/4277* (2013.01); *A61B 2562/08*
(2013.01); *A61B 2562/227* (2013.01)

(58) Field of Classification Search
CPC .............. A61B 5/4277; A61B 2562/08; A61B
2562/227; A61B 5/682; A61B 1/247;
A61B 5/228
See application file for complete search history.

(56) References Cited

U.S. PATENT DOCUMENTS 4,344,419 A  *  8/1982  Burgin ..................... A61B 1/32
600/246
8,231,531 B2 *  7/2012  Brister ................. A61B 5/0031
600/347
(Continued)

FOREIGN PATENT DOCUMENTS

CN          104506671 A       4/2015
CN          212307915 U  *   1/2021
(Continued)

OTHER PUBLICATIONS

International Search Report in PCT/JP2021/020466, mailed Aug.
10, 2021, 3 pages.

*Primary Examiner* — Jacqueline Cheng
*Assistant Examiner* — Tho Q Tran
(74) *Attorney, Agent, or Firm* — ArentFox Schiff LLP

(57) ABSTRACT

An oral body device is provided for attaching to and
detaching from an oral appliance that has an electrical
connection portion. The device includes a body, and an
attachment/detachment operation unit that has an electrical
connection conductor and is configured to detachably attach
the oral appliance to the body portion by operating appli-
cation and release of force to the oral appliance. Moreover,
the attachment/detachment operation unit fixedly attaches
the oral appliance in a state in which the electrical connec-
tion portion is electrically connected to the electrical con-
nection conductor by applying a force to the oral appliance,
and releases the fixation by releasing the force applied to the
oral appliance to detach the oral appliance.

18 Claims, 42 Drawing Sheets

(56)     References Cited

U.S. PATENT DOCUMENTS

| | | | |
|---|---|---|---|
| 2007/0055112 A1* | 3/2007 | Lesko .................. | A61B 1/0669 600/241 |
| 2016/0135728 A1 | 5/2016 | Furukawa et al. | |
| 2017/0027432 A1* | 2/2017 | Wachs .................... | A61B 1/06 |
| 2017/0340196 A1 | 11/2017 | Elazar et al. | |
| 2019/0200903 A1 | 7/2019 | Watson | |
| 2022/0133141 A1* | 5/2022 | Mock .................... | A61B 1/227 348/77 |

FOREIGN PATENT DOCUMENTS

| | | | |
|---|---|---|---|
| JP | H11-104086 A | 4/1999 | |
| JP | 2004170296 A | 6/2004 | |
| JP | 2011092233 A | 5/2011 | |
| JP | 2019517864 A | 6/2019 | |
| KR | 10-1919447 B1 | 11/2018 | |
| KR | 10-2020-0065357 A | 6/2020 | |
| WO | 2014041585 A1 | 3/2014 | |
| WO | 2015125222 A1 | 8/2015 | |

* cited by examiner

ORAL BODY DEVICE

CROSS REFERENCE TO RELATED APPLICATIONS

This application is a continuation of PCT Application No. PCT/JP2021/020466, filed May 28, 2021, which claims priority to Japanese Patent Application No. 2020-106457, filed Jun. 19, 2020, the entire contents of each of which are hereby incorporated by reference in their entirety.

TECHNICAL FIELD

The present invention relates to an oral body device to and from which an oral appliance can be attached and detached.

BACKGROUND

International Publication No. 2015/125222 (hereafter "Patent Document 1") discloses an intraoral moisture measuring instrument. The intraoral moisture measuring instrument described in Patent Document 1 includes a swing member, a moisture content detection unit provided at a front end of the swing member, and a biasing member that biases the swing member in one direction of a swing direction.

In recent years, there has been a demand for an oral body device to and from which an oral appliance used in an oral cavity can be attached and detached, in which the oral appliance can be easily attached to and detached from the oral body device.

SUMMARY OF THE INVENTION

Accordingly, in an exemplary aspect, an oral device is provided in which an oral appliance having an electrical connection portion can be attached and detached. In this aspect, the oral device includes a body portion; and an attachment/detachment operation unit that has an electrical connection conductor and is configured to detachably attach the oral appliance to the body portion by operating application and release of force to the oral appliance. Moreover, the attachment/detachment operation unit fixedly attaches the oral appliance when the electrical connection portion and the electrical connection conductor are electrically connected to each other by applying a force to the oral appliance, and releases fixation and detaches the oral appliance by releasing the force applied to the oral appliance.

According to the exemplary embodiments of the present invention, an oral body device is provided to and from which an oral appliance can be easily attached and detached.

DETAILED DESCRIPTION OF EMBODIMENTS

Figure 1:
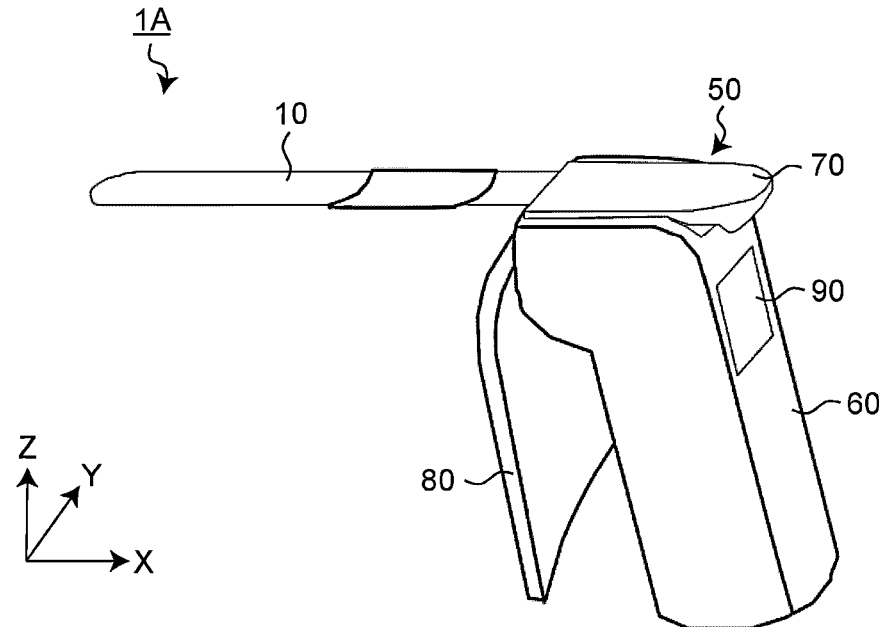
FIG. 1 is a schematic perspective view of an exemplary aspect of an oral device of Embodiment 1.

In general, in the moisture measuring instrument described above in Patent Document 1, the moisture in the oral cavity is measured by bringing a moisture content detection unit (sensor unit) provided on a front end side of the swing member that swings with respect to a main body into contact with a measurement site in the oral cavity. Further, in the moisture measuring instrument described in Patent Document 1, the sensor unit and the swing member are configured as a detachable portion that is detachable from the main body. As a result, the sanitary state of the measuring instrument is maintained in a more appropriate state. In such a device, the detachable portion is detached from the main body by pulling a front end side of the detachable portion.

However, since the detachable portion is a portion that comes into contact with the measurement site in the oral cavity, saliva adheres to the detachable portion after use. Therefore, when a user grips and pulls the front end side of the detachable portion at the time of detaching the detachable portion from the main body, saliva adheres to the user's hand.

In view of limitations of such conventional devices, there is a need for an oral body device, to and from which an oral appliance that comes into contact with a measurement site in the oral cavity can be attached and detached, in which the oral appliance can be easily attached to and detached from the oral body device. Specifically, there is a need for an oral body device from which an oral appliance can be detached after use by the operation of the oral body device without getting saliva on the user's hands.

Therefore, the present inventors have found a configuration in which an oral appliance is attached and detached by operating application and release of force to and from the oral appliance.

Accordingly, an oral body device of an exemplary aspect is provided to and from which an oral appliance having an electrical connection portion can be attached and detached. In this aspect, the device includes a body; and an attachment/detachment operation unit that has an electrical connection conductor and is configured to detachably attach the oral appliance to the body portion by operating application and release of force to the oral appliance. Moreover, the attachment/detachment operation unit fixedly attaches the oral appliance in a state in which the electrical connection portion and the electrical connection conductor are electrically connected to each other by applying a force to the oral appliance, and releases fixation and detaches the oral appliance by releasing the force applied to the oral appliance. With such a configuration, the oral appliance can be easily attached and detached.

The attachment/detachment operation unit can include: an arrangement surface on which the oral appliance is arranged; and a pressing member that applies a force in a direction intersecting the arrangement surface. With such a configuration, the oral appliance can be more easily attached and detached.

The pressing member includes one end (e.g., a first end) provided on the arrangement surface side and another end (e.g., a second end) provided on a side opposite to the one end, and can be configured to be rotatable around a rotation shaft arranged between the one end and the other end. With such a configuration, the oral appliance can be more easily attached and detached.

The pressing member can include a protrusion protruding toward the arrangement surface between the one end and the rotation shaft. With such a configuration, the oral appliance can be prevented from falling off.

The pressing member has a contact surface that comes into contact with the oral appliance, and can be configured to be slidable in an oblique direction with respect to the arrangement surface. With such a configuration, the oral appliance can be more easily attached and detached.

The pressing member includes one end provided on the arrangement surface side and another end provided on a side opposite to the one end, brings the contact surface into contact with the oral appliance by sliding in a first oblique direction from the one end toward the other end, and can release contact between the contact surface and the oral appliance while pushing out the oral appliance by sliding in a second oblique direction opposite to the first oblique direction. With such a configuration, the oral appliance can be more easily detached.

The pressing member can include a protrusion protruding from the contact surface toward the arrangement surface. With such a configuration, the oral appliance can be prevented from falling off.

A protrusion protruding toward the pressing member can be provided on the arrangement surface. With such a configuration, the oral appliance can be prevented from falling off.

The arrangement surface is curved in a concave shape or a convex shape, and the pressing member can be curved in a concave shape or a convex shape along a shape of the arrangement surface. With such a configuration, the oral appliance can be deformed and fixed.

The oral body device further includes: a detection unit that detects whether or not the oral appliance is attached to the attachment/detachment operation unit; and a control unit that determines whether or not use of the oral appliance is possible based on a detection result of the detection unit, in which the control unit determines whether or not the oral appliance attached to the attachment/detachment operation unit has been used, determines that use of the oral appliance is not possible when the oral appliance is determined to have been used, and after use of the oral appliance is determined to be not possible, can determine that use of the oral appliance is possible when the detection unit detects that a used oral appliance has been detached and that an unused oral appliance has been attached. With such a configuration, it is possible to easily determine whether or not use of the oral appliance is possible by detecting whether or not the oral appliance has been used.

The oral body device can further include a display unit that displays information on whether or not use of the oral appliance is possible. With such a configuration, it is possible to easily know whether or not use of the oral appliance is possible.

The control unit, when the oral appliance is determined to have been used, stops use of the oral appliance; and can enable use of the oral appliance based on a determination that use of the oral appliance is possible. With such a configuration, use of the used oral appliance can be stopped.

The body portion can include: a grip portion to be gripped by a user; a guard that protects the grip portion. With such a configuration, it is possible to prevent saliva or the like from flowing to the grip portion.

The electrical connection portion of the oral appliance is one or a plurality of electrodes, the electrical connection conductor of the oral body device is one or a plurality of connection terminals, and the attachment/detachment operation unit can electrically connect the one or the plurality of electrodes to the one or the plurality of connection terminals by bringing the one or the plurality of electrodes into physical contact with the one or the plurality of connection terminals. With such a configuration, the electrical connection between the oral appliance and the oral body device can be easily performed.

The electrical connection portion of the oral appliance is an RFID tag, the electrical connection conductor of the oral body device is a body side antenna, and the attachment/detachment operation unit can electrically connect the RFID tag and the body side antenna to each other by wirelessly connecting the RFID tag and the body side antenna. With such a configuration, the electrical connection between the oral appliance and the oral body device can be easily performed.

The oral body device can further include a calculation unit that calculates an amount of moisture based on information acquired by the oral appliance. With such a configuration, the amount of moisture in the oral cavity can be measured.

The electrical connection portion of the oral appliance includes a plurality of electrodes, the electrical connection conductor includes a plurality of connection terminals provided on both main surfaces of a substrate, the attachment/detachment operation unit includes a plurality of pressing members that is respectively arranged on both main surfaces of the substrate and applies a force in a direction intersecting both the main surfaces of the substrate, and the plurality of pressing members can fix the oral appliance by applying a force in a direction intersecting both main surfaces of the substrate in a state where the plurality of electrodes and the plurality of connection terminals are respectively in contact with each other. With such a configuration, it is possible to easily realize electrical connection between the oral appliance and the oral body device.

The plurality of pressing members each can have a protrusion protruding toward both main surfaces of the substrate. With such a configuration, the oral appliance can be firmly fixed to the oral body device.

Moreover, the electrical connection conductor can include a connection terminal provided on one main surface of a substrate; and a movable component that moves toward the connection terminal and comes into contact with the connection terminal, when the movable component contacts the electrical connection portion of the oral appliance, the movable component contacts the connection terminal by moving toward the connection terminal, the attachment/detachment operation unit includes a pressing member that is arranged on one main surface of the substrate and applies a force in a direction intersecting the one main surface of the substrate, and the pressing member can fix the oral appliance by applying a force in a direction intersecting one main surface of the substrate in a state in which the electrical connection portion, the movable component, and the connection terminal are in contact with each other. With such a configuration, it is possible to easily and stably realize the electrical connection between the oral appliance and the oral body device.

An exemplary embodiment will be described below with reference to the accompanying drawings. Note that the following description is merely illustrative in nature and is not intended to limit the present disclosure, applications thereof, or uses thereof. Further, the drawings are schematic, and ratios of respective dimensions and the like do not necessarily match actual ones.

Exemplary Embodiment 1

Figure 2:
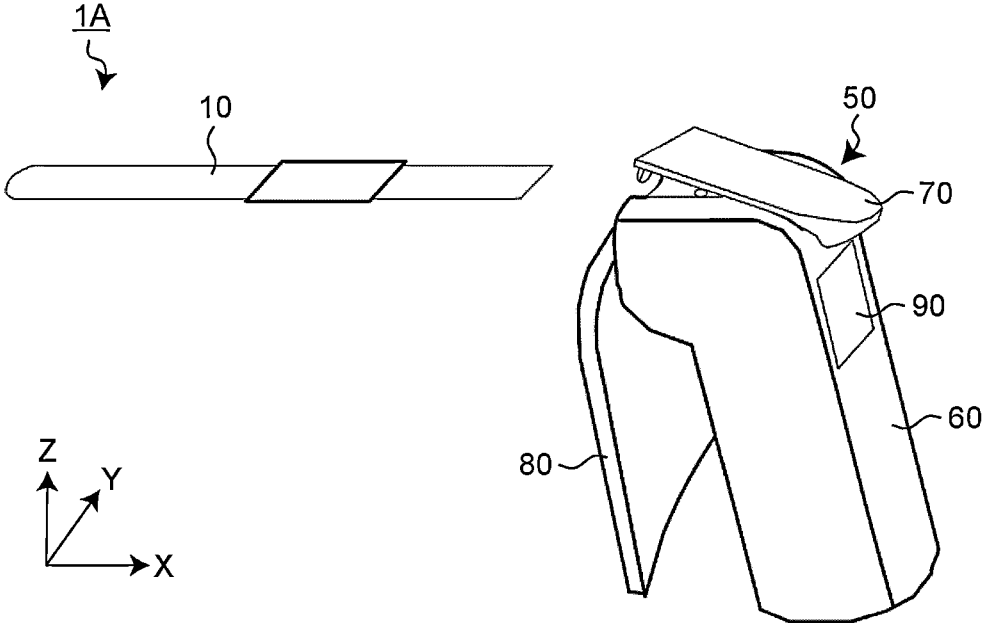
FIG. 2 is a schematic perspective view of an exemplary aspect of the oral device of Embodiment 1.

[Oral Device]
FIG. 1 and FIG. 2 are schematic perspective views of an exemplary aspect of an oral device 1A of Embodiment 1. FIG. 1 illustrates a state in which an oral appliance 10 is attached to an oral body device 50. FIG. 2 illustrates a state in which the oral appliance 10 is detached from the oral body device 50. X, Y, and Z directions in the figures indicate a length direction, a width direction, and a height direction of the oral device 1A, respectively.

As illustrated in FIG. 1 and FIG. 2, the oral device 1A includes the oral appliance 10 and the oral body device 50. The oral device 1A is a disposable-type device. In the oral device 1A, the oral appliance 10 to be used in the oral cavity is detachably attached to the oral body device 50. After the oral appliance 10 is attached to the oral body device 50 and used, the oral appliance 10 is detached from the oral body device 50.

The oral device 1A performs a function by bringing the oral appliance 10 into contact with a site in the oral cavity. The function includes, for example, a sensing function and/or an energy irradiation function.

The sensing function acquires information related to biological information in the oral cavity. In an exemplary aspect, the biological information is various physiological and anatomical information generated by a living body. The biological information is, for example, information such as dryness (degree of wetness, water content), tongue pressure, occlusal force, chewing function, swallowing function, tongue-lip movement function, poor hygiene, saliva components, exhaled gas components, body temperature, and hardness. The information related to the biological information is, for example, information such as electrostatic capacity, impedance (resistance), pressure, potential, color tone, temperature, hardness, and vibration. The oral device 1A brings the oral appliance 10 into contact with a measurement site in the oral cavity of the user, and acquires information related to biological information of the measurement site with which the oral appliance 10 is brought into contact. The oral device 1A measures the state in the oral cavity by acquiring biological information with the oral body device 50 based on the information acquired by the oral appliance 10. The oral body device 50 measures, for example, an amount of moisture, an amount of salivation, an occlusal force, a tongue pressure, a color tone of the tongue, and/or an amount of various substances contained in saliva.

The energy irradiation function irradiates the oral cavity with energy. The energy is, for example, energy such as light, heat, ultrasonic waves, or electromagnetic waves.

The oral device 1A can be used as, for example, a hygrometer, a bite force meter, a tongue pressure meter, a laser treatment device, a thermotherapy device, an ultrasonic echo, an ultrasonic treatment device, or an electromagnetic irradiation device.

In Embodiment 1, an exemplary aspect in which the oral device 1A is a hygrometer will be described.

Figure 3:
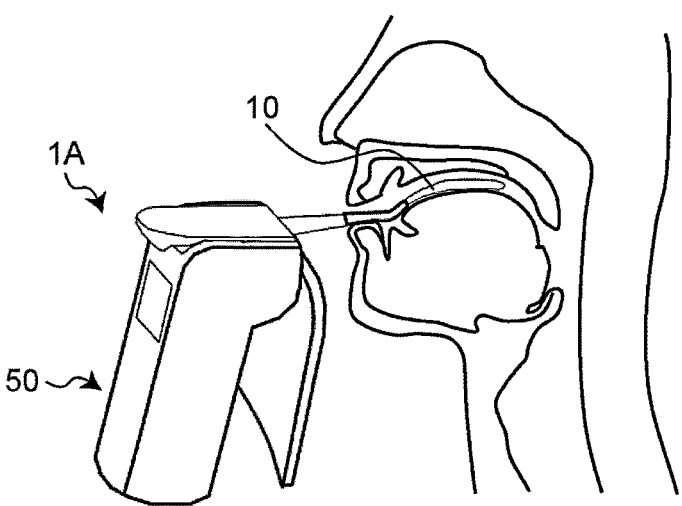
FIG. 3 is a schematic view illustrating an exemplary aspect of a state in which the oral device of Embodiment 1 is used.

FIG. 3 is a schematic view illustrating an exemplary aspect of a state in which the oral device 1A of Embodiment 1 is used. As illustrated in FIG. 3, the oral device 1A brings the oral appliance 10 into contact with a measurement site in the oral cavity of the user. The measurement site is, for example, the tongue, buccal mucosa, palate, or the like in the oral cavity. The oral appliance 10 comes into contact with the measurement site by deforming along the shape of the measurement site. The oral device 1A starts measurement in a state in which the oral appliance 10 is brought into contact with the measurement site in the oral cavity.

Figure 4:
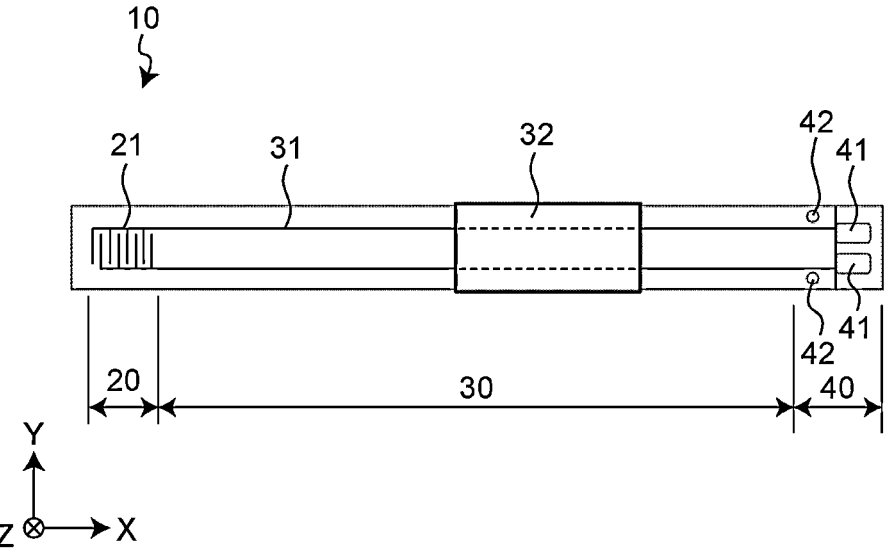
FIG. 4 is a schematic view illustrating an exemplary aspect of an oral appliance.
Figure 5:
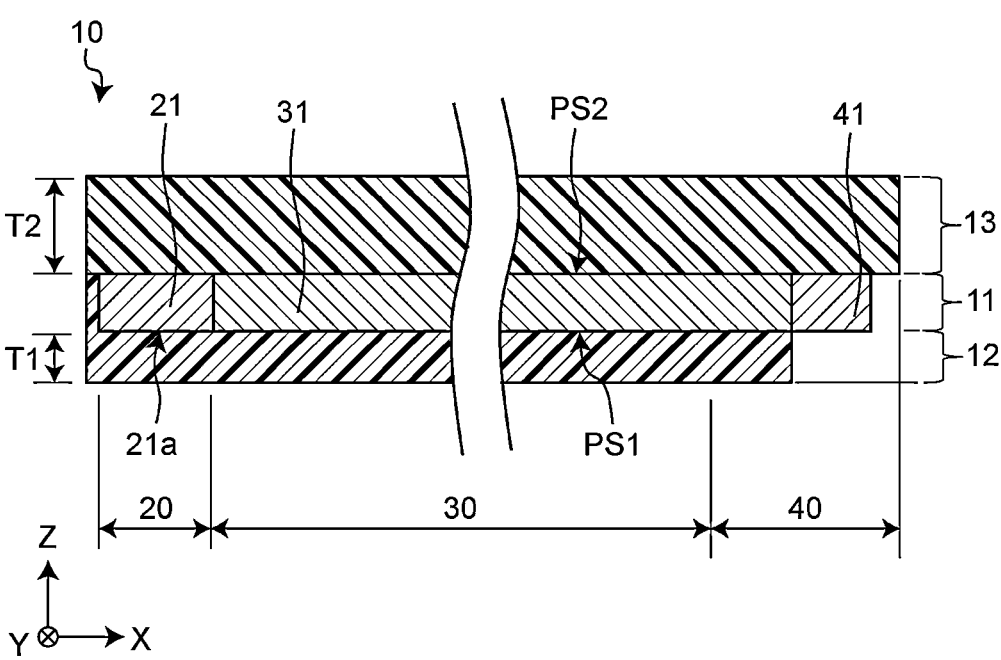
FIG. 5 is a schematic cross-sectional view of an exemplary aspect of the oral appliance of FIG. 4 in an enlarged manner.
Figure 6:
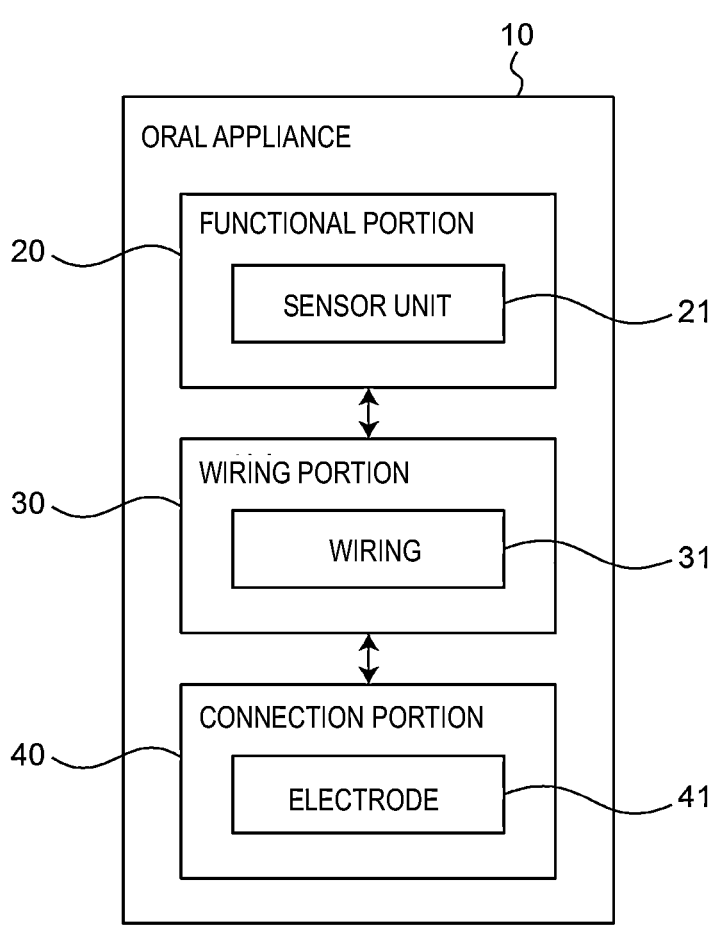
FIG. 6 is a block diagram illustrating a main configuration of an exemplary aspect of an oral appliance.

[Oral Appliance]
FIG. 4 is a schematic view illustrating an exemplary aspect of the oral appliance 10. FIG. 5 is a schematic cross-sectional view of an exemplary aspect of the oral appliance 10 of FIG. 4 in an enlarged manner. FIG. 6 is a block diagram illustrating a configuration of an exemplary aspect of the oral appliance 10.

As illustrated in FIG. 4 to FIG. 6, the oral appliance 10 includes a functional portion 20, a wiring portion 30, and a connection portion 40.

In Embodiment 1, the oral appliance 10 is configured as a sensing probe that is attachable to and detachable from the oral body device 50. The oral appliance 10 is a sheet-shaped appliance having an electrical connection portion. The oral appliance 10 is formed in a rectangular sheet shape having a longitudinal direction. Further, the oral appliance 10 has flexibility and can be deformed.

The electrical connection portion is electrically connected to the oral body device 50. In Embodiment 1, the electrical connection portion includes one or a plurality of electrodes 41.

<Functional Portion>

The functional portion 20 (or functional unit) is a portion that exhibits a sensing function, and is provided on a front end side of the oral appliance 10. The functional portion 20 includes a sensor unit 21 that acquires information in the oral cavity. The sensor unit 21 has a sensor surface 21a arranged on the measurement site side in the oral cavity of the user. The functional portion 20 acquires intraoral information by bringing the sensor surface 21a side of the sensor unit 21 into surface contact with the measurement site. In Embodiment 1, the sensor unit 21 includes an electrostatic capacity sensor and acquires electrostatic capacity.

<Wiring Portion>

The wiring portion 30 is arranged between the functional portion 20 and the connection portion 40. The wiring portion 30 includes a wiring 31 that electrically connects the functional portion 20 and the electrode 41 of the connection portion 40. The wiring 31 is formed of a conductive material. For example, the wiring 31 is formed by a wiring conductor pattern.

In an exemplary aspect, a thickness of a wiring layer 11 is preferably equal to or more than 1 μm and equal to or less than 50 μm. More preferably, the thickness of the wiring layer 11 is equal to or more than 2 μm and equal to or less than 25 μm.

In addition, the wiring portion 30 includes a protective layer 32 that covers the periphery of the wiring portion 30. The protective layer 32 is arranged at a portion where teeth touch when the oral appliance 10 is arranged in the oral cavity. The protective layer 32 only needs to be arranged between the functional portion 20 and the connection portion 40. For example, the protective layer 32 is formed of a protective film having a thickness of equal to or more than 100 μm and equal to or less than 10 mm. The protective film can be formed of a material such as resin or a foam.

<Connection Portion>

The connection portion 40 is a portion to be attached to the oral body device 50, and is provided on a rear end side opposite to a front end of the oral appliance 10. The connection portion 40 includes one or the plurality of electrodes 41. In Embodiment 1, the connection portion 40 includes two electrodes 41. It is noted that the number of the electrodes 41 is not limited to two.

The one or the plurality of electrodes 41 is formed of a material having conductivity.

In Embodiment 1, when the connection portion 40 is attached to the oral body device 50, the plurality of electrodes 41 is electrically connected by a physical contact with a plurality of connection terminals provided in the oral body device 50.

In addition, the connection portion 40 is provided with a mounting hole 42. The mounting hole 42 is a through-hole into which a protrusion 73a of an attachment/detachment operation unit 70 described later is inserted. In Embodiment 1, two mounting holes 42 are provided in the connection portion 40.

Note that, the mounting hole 42 is not limited to a through-hole, and can be a notch or a recess. The mounting hole 42 can have any size as long as the protrusion 73a of the attachment/detachment operation unit 70 can be inserted therein. In addition, the connection portion 40 only needs to be provided with one or a plurality of mounting holes 42.

As illustrated in FIG. 5, the oral appliance 10 is formed of the wiring layer 11 and a plurality of insulating layers 12 and 13. In Embodiment 1, the wiring layer 11 and the plurality of insulating layers 12 and 13 are stacked.

<Wiring Layer>

The wiring layer 11 includes the sensor unit 21, the wiring 31, and the plurality of electrodes 41. The wiring layer 11 has a first main surface PS1 and a second main surface PS2 opposite to the first main surface PS1. In the oral appliance 10, the first main surface PS1 side is a side that comes into contact with a measurement site in the oral cavity. In Embodiment 1, the sensor surface 21a of the sensor unit 21 is arranged on the first main surface PS1 side of the wiring layer 11. On the first main surface PS1 side of the wiring layer 11, the plurality of electrodes 41 is exposed from the insulating layer 12.

<Plurality of Insulating Layers>

The plurality of insulating layers 12 and 13 includes the first insulating layer 12 arranged on a first main surface PS1 of the wiring layer 11 and a second insulating layer 13 arranged on the second main surface PS2 of the wiring layer 11.

A thickness T1 of the first insulating layer 12 is smaller than a thickness T2 of the second insulating layer 13. The thickness T1 of the first insulating layer 12 is preferably equal to or less than 25 μm. The thickness T2 of the second insulating layer 13 is preferably equal to or more than 10 μm and equal to or less than 200 μm.

For example, the wiring layer 11 and the plurality of insulating layers 12 and 13 can be formed of a flexible printed circuit board.

Note that the oral appliance 10 described above is an exemplary aspect, and the configuration of the oral appliance 10 is not limited thereto. The oral appliance 10 can be any appliance having an electrical connection portion. In addition, the shape of an oral appliance 10 is not limited to a sheet shape. Alternatively, the oral appliance 10 can include a shield layer in addition to the wiring layer 11 and the plurality of insulating layers 12 and 13.

[Oral Body Device]

Figure 7:
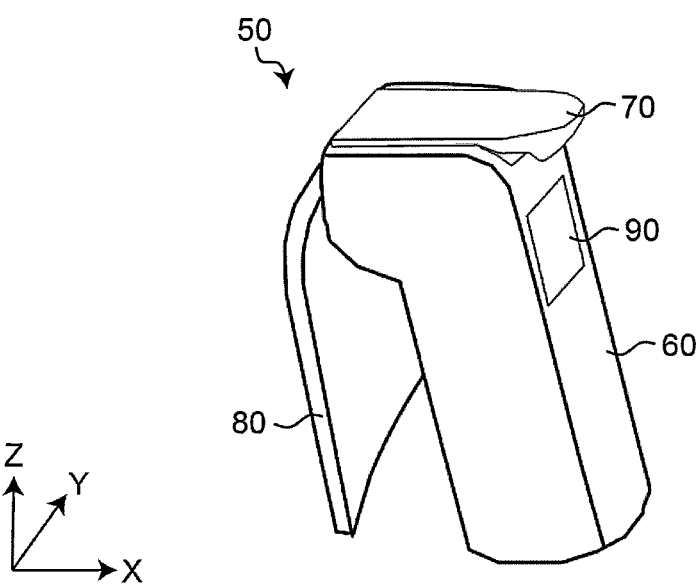
FIG. 7 is a schematic perspective view of an exemplary aspect of an oral body device.
Figure 8:
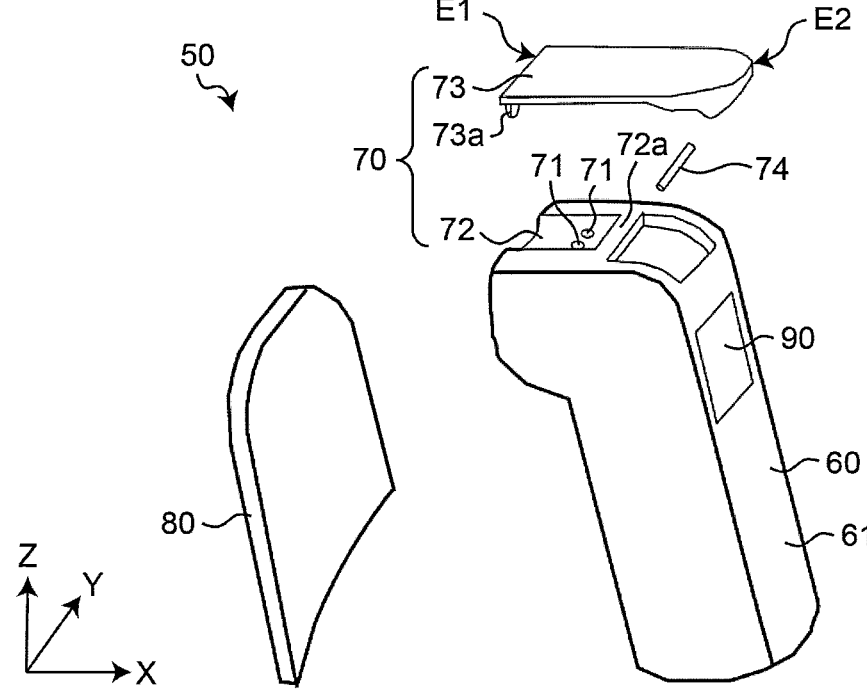
FIG. 8 is a schematic exploded view of an exemplary aspect of the oral body device of FIG. 7.
Figure 9:
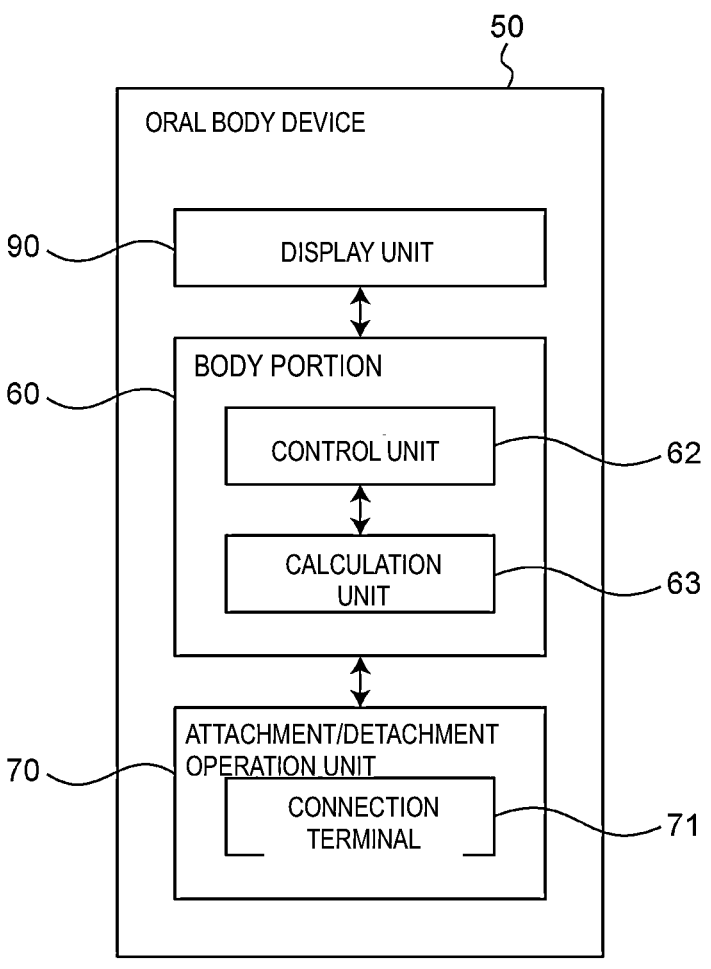
FIG. 9 is a block diagram illustrating a main configuration of an exemplary aspect of the oral body device.

FIG. 7 is a schematic perspective view of an exemplary aspect of the oral body device 50. FIG. 8 is a schematic exploded view of an exemplary aspect of the oral body device 50 of FIG. 7. FIG. 9 is a block diagram illustrating a configuration of an exemplary aspect of the oral body device 50. It is noted that, hereinafter, the oral body device 50 can be referred to as the body device 50.

As illustrated in FIG. 7 to FIG. 9, the body device 50 includes a body portion 60, the attachment/detachment operation unit 70, a guard 80, and a display unit 90. Note that in Embodiment 1, an exemplary aspect in which the body device 50 includes the guard 80 and the display unit 90 will be described, but the exemplary aspects are not limited thereto. The guard 80 and the display unit 90 are not essential components. For example, the display unit 90 can be provided in a device different from the body device 50.

In the body device 50, the oral appliance 10 can be detachably attached to the attachment/detachment operation unit 70. Further, the body device 50 calculates the amount of a measurement target based on the information related to the biological information acquired by the oral appliance 10. Specifically, the body device 50 calculates the amount of moisture (e.g., degree of wetness) based on the electrostatic capacity acquired by the oral appliance 10.

<Body Portion>

The body portion 60 is a body portion of the body device 50. The body portion 60 is formed of a rod-shaped member having a longitudinal direction. The body portion 60 includes a grip portion 61 to be gripped by a user. The grip portion 61 is formed by the external shape of the body portion 60.

The attachment/detachment operation unit 70 is arranged on one end side of the body portion 60. The guard 80 and the display unit 90 are arranged in the body portion 60.

Moreover, the body portion 60 includes a control unit 62 and a calculation unit 63.

The control unit 62 integrally controls the components forming the oral device 1A. The control unit 62 includes, for example, a memory storing a program and a processing circuit corresponding to a processor such as a central processing unit (CPU). For example, in the control unit 62, the processor executes a program stored in the memory to perform the algorithms and functions described herein.

The control unit 62 controls the calculation unit 63 and the display unit 90.

The calculation unit 63 calculates the amount of a measurement target based on the information acquired by the oral appliance 10. In Embodiment 1, the calculation unit 63 calculates the amount of moisture based on the electrostatic capacity acquired by the oral appliance 10.

The calculation unit 63 can be realized by a semiconductor element or the like. The function of the calculation unit 63 can be configured only by hardware or can be realized by a combination of hardware and software in an alternative exemplary aspect.

In Embodiment 1, the calculation unit 63 includes a moisture content calculation circuit. The moisture content calculation circuit calculates the amount of moisture from the electrostatic capacity acquired by the oral appliance 10 based on a relational expression between the electrostatic capacity and the amount of moisture.

Information on the amount of moisture calculated by the calculation unit 63 is transmitted to the display unit 90.

<Attachment/Detachment Operation Unit>

The attachment/detachment operation unit 70 is configured to detachably attach the oral appliance 10 to the body portion 60 by operating application and release of a force to the oral appliance 10. In Embodiment 1, the attachment/detachment operation unit 70 is configured to detachably attach the oral appliance 10 in a direction intersecting a direction in which the body portion 60 extends. That is, an attachment/detachment direction of the oral appliance 10 is a direction intersecting the direction in which the body portion 60 extends.

The attachment/detachment operation unit 70 has an electrical connection conductor. The electrical connection conductor is a conductor that is electrically connected to the oral appliance 10. Specifically, the electrical connection conductor is electrically connected to an electrical connection portion of the oral appliance 10. In Embodiment 1, the electrical connection conductor is one or a plurality of connection terminals 71. The one or the plurality of connection terminals 71 is formed of a material having conductivity. The one or the plurality of connection terminals 71 is electrically connected by a physical contact with one or the plurality of electrodes 41 provided at the connection portion 40 of the oral appliance 10.

The attachment/detachment operation unit 70 fixedly attaches the oral appliance 10 in a state in which the electrode 41 and the connection terminal 71 are electrically connected by applying a force to the connection portion 40 of the oral appliance 10. In addition, the attachment/detachment operation unit 70 releases the fixation and detaches the oral appliance 10 by releasing the force applied to the connection portion 40 of the oral appliance 10. Further, when the oral appliance 10 is detached, the electrical connection between the electrode 41 and the connection terminal 71 can be released.

As further shown, the attachment/detachment operation unit 70 includes an arrangement surface 72 on which the oral appliance 10 is arranged, and a pressing member 73 that applies a force in a direction intersecting the arrangement surface 72. In Embodiment 1, the pressing member 73 is arranged above the arrangement surface 72.

The arrangement surface 72 is provided on an end surface on one end side of the body portion 60. The arrangement surface 72 is a surface on which the oral appliance 10 can slide. The arrangement surface 72 can be formed by denting the end surface on the one end side of the body portion 60 in a concave shape, or can be formed as a flat surface.

The one or the plurality of connection terminals 71 is arranged on the arrangement surface 72. The one or the plurality of connection terminals 71 is arranged at positions corresponding to the one or the plurality of electrodes 41 when the oral appliance 10 is arranged and fixed on the arrangement surface 72. In Embodiment 1, two connection terminals 71 are arranged on the arrangement surface 72. Note that the number of connection terminals 71 is not limited to two.

The arrangement surface 72 is provided with a positioning member 72a extending toward the pressing member 73. The positioning member 72a determines the position in the X direction on the arrangement surface 72. For example, the positioning member 72a can be formed by a step formed on the arrangement surface 72, or can be formed to protrude in a convex shape from the arrangement surface 72 toward the pressing member 73. For example, when the oral appliance 10 is slid in the X direction and arranged on the arrangement surface 72, the oral appliance 10 is slid until an end portion of the connection portion 40 of the oral appliance 10 comes into contact with the positioning member 72a. As described above, when the oral appliance 10 is attached to the attachment/detachment operation unit 70, the oral appliance 10 is slid until coming into contact with the positioning member 72a, whereby the position of the oral appliance 10 in the X direction can be easily determined. This facilitates attachment at a position where the electrode 41 of the oral appliance 10 and the connection terminal 71 arranged on the arrangement surface 72 are in physical contact with each other, and electrical connection can be easily performed.

The pressing member 73 is a member configured for operating application and release of force to the oral appliance 10. The pressing member 73 is configured to apply a force in a direction intersecting the arrangement surface 72. Thus, pressing member 73 can fix the oral appliance 10 to the arrangement surface 72 in a state in which the electrode 41 and the connection terminal 71 are electrically connected.

The pressing member 73 is formed of a plate-shaped member having one end E1 and the other end E2. The one end E1 is provided on the arrangement surface 72 side. The other end E2 is provided on a side opposite to the one end E1. A rotation shaft 74 is arranged between the one end E1 and the other end E2 of the pressing member 73. The pressing member 73 is configured to be rotatable around the rotation shaft 74. In addition, the one end E1 of the pressing member 73 is biased in a direction approaching the arrangement surface 72 by, for example, an elastic body. Exemplary aspects of the elastic body include a spring, rubber, and the like.

The pressing member 73 has the protrusion 73a protruding toward the arrangement surface 72 between the one end E1 and the rotation shaft 74. The protrusion 73*a* is inserted into the mounting hole 42 provided in the connection portion 40 of the oral appliance 10. In Embodiment 1, the pressing member 73 has two protrusions 73*a* provided at the one end E1 of the pressing member 73. Note that the pressing member 73 only needs to have one or a plurality of the protrusions 73*a*.

The attachment/detachment operation unit 70 operates application and release of force to the oral appliance 10 by operating a rotation operation of the pressing member 73. To be specific in this exemplary aspect, in a state in which the pressing member 73 is not operated, the one end E1 of the pressing member 73 moves in a direction approaching the arrangement surface 72 by the biasing force of the elastic body, and presses against the oral appliance 10 arranged on the arrangement surface 72. Accordingly, the oral appliance 10 can be fixed so as to be sandwiched between the arrangement surface 72 and the pressing member 73, and the oral appliance 10 can be attached to the attachment/detachment operation unit 70. In addition, by inserting the protrusion 73*a* of the pressing member 73 into the mounting hole 42 of the connection portion 40, the oral appliance 10 can be fixed so as not to be detached from the attachment/detachment operation unit 70.

When the oral appliance 10 is detached from the attachment/detachment operation unit 70, the one end E1 of the pressing member 73 moves in a direction away from the arrangement surface 72 by pressing down the other end E2 of the pressing member 73. Accordingly, a pressing force against the oral appliance 10 by the pressing member 73 is released, and the oral appliance 10 can be detached from the attachment/detachment operation unit 70. In this way, since the oral appliance 10 can be detached by the operation of the attachment/detachment operation unit 70, the oral appliance 10 can be easily detached without touching a used oral appliance 10.

Note that in Embodiment 1, an exemplary aspect in which the pressing member 73 is biased by an elastic body has been described, but the exemplary aspects are not limited thereto. In the pressing member 73, the force can be applied to the pressing member 73 in a direction intersecting the arrangement surface 72 by a mechanism other than the elastic body, for example, a lock mechanism, a slide mechanism, and/or an electromagnetic force. In addition, a suction portion can be provided to apply a force to the oral appliance 10 by a suction force.

<Guard>

The guard 80 is arranged on the body portion 60 and protects the grip portion 61. When the user uses the oral device 1A, the guard 80 prevents saliva from adhering to the hand of the user holding the grip portion 61.

In Embodiment 1, the guard 80 is arranged on the body portion 60 on the side to which the oral appliance 10 is attached. The side to which the oral appliance 10 is attached refers to the side to and from which the oral appliance 10 is attached and detached. In addition, the guard 80 is formed of a plate-shaped member.

<Display Unit>

The display unit 90 is arranged in the body portion 60 and displays information on the oral device 1A. The information on the oral device 1A includes, for example, information on a measurement subject.

In Embodiment 1, the information on the measurement subject is information on the amount of moisture. For example, the calculation unit 63 calculates the amount of moisture based on the electrostatic capacity acquired by the oral appliance 10. The calculation unit 63 transmits information on the amount of moisture to the display unit 90.

The display unit 90 is, for example, a display such as an electronic display.

Note that the body device 50 can include an input unit for inputting input information from the user. For example, the input unit can have one or a plurality of buttons for receiving an input from the user. The one or the plurality of buttons can include, for example, a power button for switching power ON/OFF, a measurement start button for starting measurement, and the like.

[Exemplary Operation of Attachment/Detachment Operation Unit]

Figure 10A:
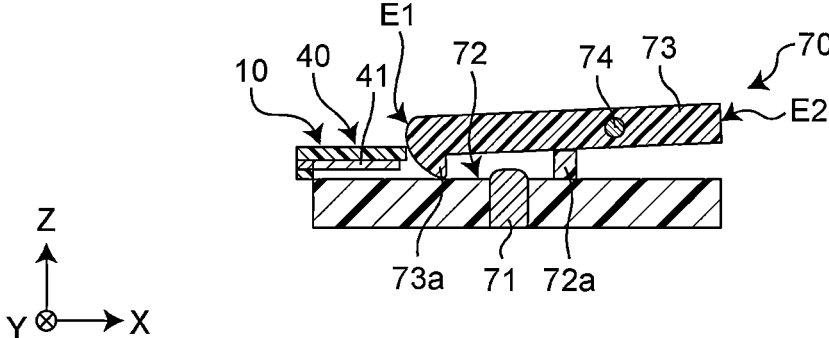
FIG. 10A is a schematic diagram illustrating an exemplary aspect of an operation of an attachment/detachment operation unit.
Figure 10B:
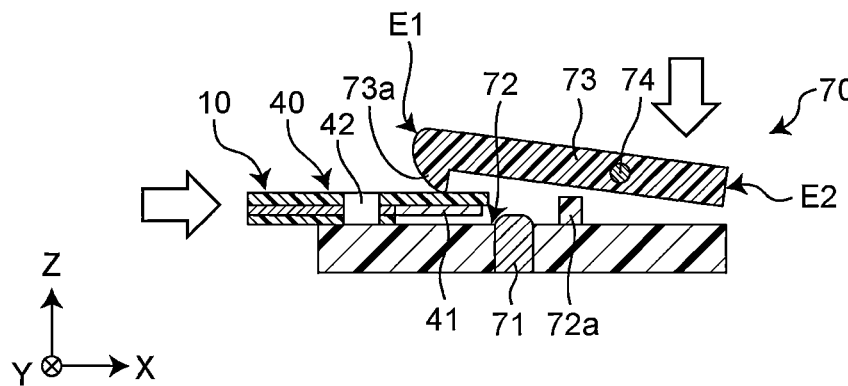
FIG. 10B is a schematic diagram illustrating an exemplary aspect of the operation of the attachment/detachment operation unit.
Figure 10C:
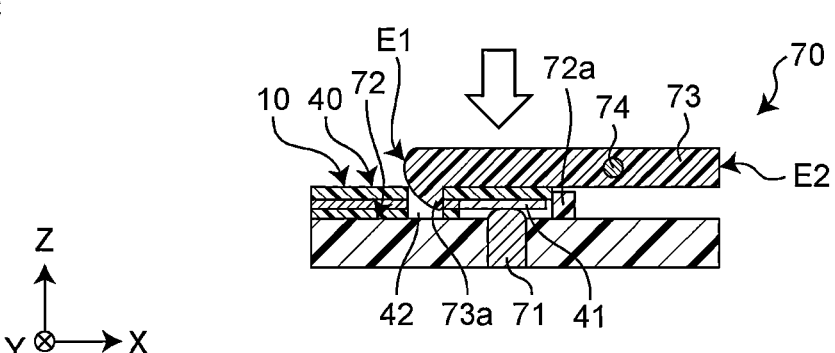
FIG. 10C is a schematic diagram illustrating an exemplary aspect of the operation of the attachment/detachment operation unit.
Figure 11:
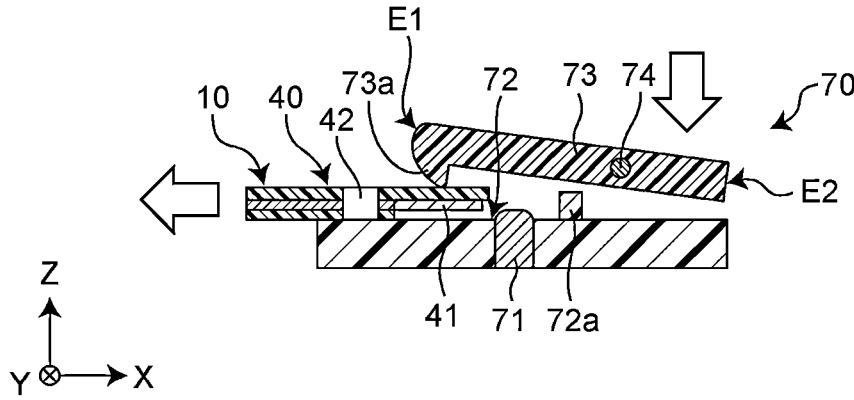
FIG. 11 is a schematic diagram illustrating an exemplary aspect of the operation of the attachment/detachment operation unit.

An exemplary aspect of the operation of the attachment/detachment operation unit 70 will be described with reference to FIGS. 10A to 10C and FIG. 11. FIGS. 10A to 10C and FIG. 11 are schematic diagrams illustrating an exemplary aspect of the operation of the attachment/detachment operation unit 70. FIGS. 10A to 10C illustrate an exemplary aspect of an operation of attaching the oral appliance 10. FIG. 11 illustrates an exemplary aspect of an operation for detaching the oral appliance 10.

First, an exemplary aspect of the operation of attaching the oral appliance 10 will be described. As illustrated in FIG. 10A, before the oral appliance 10 is attached, the one end E1 of the pressing member 73 is pressed against the arrangement surface 72 by the biasing force of the elastic body. Meanwhile, the other end E2 of the pressing member 73 is lifted upward.

As illustrated in FIG. 10B, the other end E2 of the pressing member 73 is pressed downward. As a result, the pressing member 73 rotates around the rotation shaft 74, and the one end E1 of the pressing member 73 moves upward. That is, when a force is applied in a direction in which the other end E2 of the pressing member 73 is pressed down, the one end E1 of the pressing member 73 moves in a direction away from the arrangement surface 72, and a space is formed between the arrangement surface 72 and the pressing member 73.

In a state in which the one end E1 of the pressing member 73 is lifted upward, the connection portion 40 of the oral appliance 10 is slid on the arrangement surface 72 and inserted into the attachment/detachment operation unit 70. In particular, the oral appliance 10 is slid until the end portion of the connection portion 40 comes into contact with the positioning member 72*a*. The connection portion 40 of the oral appliance 10 is positioned at a position where the electrode 41 and the connection terminal 71 are in physical contact with each other. Thus, the electrode 41 and the connection terminal 71 are electrically connected to each other.

As illustrated in FIG. 10C, in a state in which the connection portion 40 of the oral appliance 10 is arranged on the arrangement surface 72, the force applied to the other end E2 of the pressing member 73 is released. As a result, the one end E1 of the pressing member 73 moves toward the arrangement surface 72 and presses against the connection portion 40 of the oral appliance 10. The connection portion 40 of the oral appliance 10 is sandwiched and fixed between the arrangement surface 72 and the pressing member 73.

Further, the protrusion 73*a* provided at the one end E1 of the pressing member 73 is inserted into the mounting hole 42 of the connection portion 40 of the oral appliance 10. As such, the oral appliance 10 can be prevented from falling off from the attachment/detachment operation unit 70.

In this manner, the attachment/detachment operation unit 70 fixedly attaches the oral appliance 10 to the body device 50 in a state in which the electrode 41 and the connection terminal 71 are electrically connected to each other by applying the pressing force to the oral appliance 10 by the pressing member 73.

Next, an exemplary aspect of the operation of detaching the oral appliance 10 will be described. As illustrated in FIG. 11, the other end E2 of the pressing member 73 is pressed downward. As a result, the pressing member 73 rotates around the rotation shaft 74, and the one end E1 of the pressing member 73 moves upward. That is, when a force is applied in a direction in which the other end E2 of the pressing member 73 is pressed down, the one end E1 of the pressing member 73 moves in a direction away from the arrangement surface 72. Accordingly, the pressing force applied by the pressing member 73 to the connection portion 40 of the oral appliance 10 is released. Further, the protrusion 73a of the pressing member 73 comes out of the mounting hole 42 of the connection portion 40.

In this way, the attachment/detachment operation unit 70 releases the fixation by releasing the pressing force applied to the oral appliance 10 by the pressing member 73 and detaches the oral appliance 10 from the body device 50.

[Effects]

According to the oral body device 50 according to Embodiment 1, the following effects can be achieved.

The oral body device 50 can attach and detach the oral appliance 10 having an electrical connection portion thereto and therefrom. The oral body device 50 includes the body portion 60 and the attachment/detachment operation unit 70. The attachment/detachment operation unit 70 has an electrical connection conductor, and is configured to detachably attach the oral appliance 10 to the body portion 60 by operating application and release of force to the oral appliance 10. The attachment/detachment operation unit 70 fixedly attaches the oral appliance 10 in a state in which the electrical connection portion and the electrical connection conductor are electrically connected by applying a force to the oral appliance 10. In addition, the attachment/detachment operation unit 70 releases the force applied to the oral appliance 10 to thereby release the fixation and detach the oral appliance 10.

With such a configuration, the oral appliance 10 can be easily attached and detached. Specifically, the oral body device 50 can easily perform the attachment and detachment of the oral appliance 10 by the operation of the attachment/detachment operation unit 70.

After the oral appliance 10 is used, the user releases the force fixing the oral appliance 10 by the operation of the attachment/detachment operation unit 70, and can detach the oral appliance 10 from the body device 50. That is, the user can easily detach the oral appliance 10 without touching the oral appliance 10. Thus, the user can detach the oral appliance 10 from the body device 50 without touching the used oral appliance 10 to which saliva or the like has adhered.

While the oral appliance 10 is attached to the body device 50, the electrical connection portion of the oral appliance 10 and the electrical connection conductor of the body device 50 can be easily electrically connected. In addition, attachment of the oral appliance 10 to the body device 50 and electrical connection between the oral appliance 10 and the body device 50 can be realized by one mechanism. As such, the number of components forming the body device 50 can be reduced, and the device cost can also be reduced.

By configuring the oral appliance 10 used in the oral cavity to be attachable to and detachable from the body device 50, it can be used without using a cover or the like. Accordingly, in a case where the oral appliance 10 is used for the purpose of sensing, the oral appliance 10 can be brought into direct contact with a measurement site in the oral cavity, and thus measurement accuracy can be improved.

The attachment/detachment operation unit 70 includes the arrangement surface 72 on which the oral appliance 10 is arranged, and the pressing member 73 that applies a force in a direction intersecting the arrangement surface 72. With such a configuration, the attachment/detachment operation unit 70 presses against the oral appliance 10 arranged on the arrangement surface 72 by the pressing member 73, and can fixedly attach the oral appliance 10 to the body device 50. In addition, the oral appliance 10 can be easily detached from the body device 50 by releasing the pressing force of the pressing member 73. In this manner, the oral appliance 10 can be easily attached and detached by applying and releasing the pressing force of the pressing member 73 to the oral appliance 10 arranged on the arrangement surface 72.

The pressing member 73 has the one end E1 provided on the arrangement surface 72 side and the other end E2 provided on a side opposite to the one end E1, and is configured to be rotatable around the rotation shaft 74 arranged between the one end E1 and the other end E2. With such a configuration, it is possible to easily apply and release the pressing force by the pressing member 73. That is, the operability of the attachment/detachment operation unit 70 is improved. As such, the oral appliance 10 can be more easily attached and detached.

The pressing member 73 has the protrusion 73a protruding toward the arrangement surface 72 between the one end E1 and the rotation shaft 74. With such a configuration, it is possible to prevent the oral appliance 10 from coming off from the attachment/detachment operation unit 70. For example, by inserting the protrusion 73a into the mounting hole 42 provided in the oral appliance 10, it is possible to prevent the oral appliance 10 from moving in a detaching direction. Accordingly, the oral appliance 10 can be more firmly fixed.

The body portion 60 includes the grip portion 61 gripped by a user and the guard 80 that protects the grip portion 61. With such a configuration, the guard 80 can protect the hand of the user gripping the grip portion 61 from adhesion of saliva or the like.

Moreover, in an exemplary aspect, The electrical connection portion of the oral appliance 10 is one or the plurality of electrodes 41. The electrical connection conductor of the oral body device 50 is one or the plurality of connection terminals 71. The attachment/detachment operation unit 70 brings one or the plurality of electrodes 41 into physical contact with one or the plurality of connection terminals 71 to thereby electrically connect them. With such a configuration, it is possible to easily perform electrical connection between the oral appliance 10 and the body device 50.

The oral body device 50 includes the calculation unit 63 that calculates the amount of moisture based on the information acquired by the oral appliance 10. With such a configuration, the amount of moisture in the oral cavity can be measured.

Note that in Embodiment 1, an exemplary aspect in which the oral device 1A is an oral moisture meter that measures the amount of moisture in the oral cavity has been described, but the exemplary aspects are not limited thereto. The oral device 1A only needs to be a device that acquires intraoral information and/or a device that irradiates the oral cavity with energy.

Although an exemplary aspect in which the sensor unit 21 of the oral appliance 10 includes an electrostatic capacity sensor has been described in Embodiment 1, the exemplary aspects are not limited thereto. For example, the sensor unit 21 only needs to include a sensor that can acquire biological information. For example, the sensor unit 21 only needs to include at least one of an impedance measurement sensor, a resistance sensor, a weight sensor, a humidity sensor, a pressure sensor, a color sensor, a temperature sensor, a hardness sensor, a vibration sensor, a biosensor, and the like.

In Embodiment 1, an exemplary aspect in which the calculation unit 63 calculates the amount of moisture from the electrostatic capacity has been described, but the exemplary aspects are not limited thereto. The calculation unit 63 only needs to be configured to calculate the intraoral information based on the information acquired by the oral appliance 10.

In Embodiment 1, an exemplary aspect in which the attachment/detachment operation unit 70 is configured to detachably attach the oral appliance 10 in a direction intersecting the direction in which the body portion 60 extends has been described, but the exemplary aspects are not limited thereto. For example, the attachment/detachment operation unit 70 can be configured to detachably attach the oral appliance 10 parallel to the direction in which the body portion 60 extends.

In Embodiment 1, an exemplary aspect in which the attachment/detachment operation unit 70 includes the positioning member 72a has been described, but the exemplary aspects are not limited thereto. For example, the attachment/detachment operation unit 70 need not include the positioning member 72a.

In Embodiment 1, an exemplary aspect in which the connection terminal 71 is arranged on the arrangement surface 72 has been described, but the exemplary aspects are not limited thereto. For example, the connection terminal 71 can be arranged on the pressing member 73.

In Embodiment 1, an exemplary aspect in which the oral appliance 10 is attached and detached by applying and releasing the pressing force to the oral appliance 10 by the pressing member 73 has been described, but the exemplary aspects are not limited thereto. For example, the oral appliance 10 can be attached and detached by the pressing force and/or the electromagnetic force by the pressing member 73. For example, the electrode 41 of the oral appliance 10 can be formed of a metal that reacts to magnets. Exemplary aspects of the metal that reacts to magnets include iron, cobalt, nickel, and the like. Further, the body device 50 can be provided with a magnet. The electrode 41 of the oral appliance 10 can be attracted to the arrangement surface 72 by the magnetic force of the magnet provided in the body device 50.

In Embodiment 1, an exemplary aspect in which the pressing member 73 is configured to be rotatable around the rotation shaft 74 has been described, but the exemplary aspects are not limited thereto. The pressing member 73 only needs to have a configuration configured to apply and release a force to the oral appliance 10 arranged on the arrangement surface 72.

In Embodiment 1, an exemplary aspect in which the pressing member 73 has the protrusion 73a has been described, but the present invention is not limited thereto. For example, the pressing member 73 does not have to include the protrusion 73a in an alternative aspect.

In Embodiment 1, an exemplary aspect in which the protrusion 73a is provided at the one end E1 of the pressing member 73 has been described, but the exemplary aspects are not limited thereto. The protrusion 73a only needs to be provided at a position where the protrusion 73a is inserted into the mounting hole 42 of the oral appliance 10.

In Embodiment 1, an exemplary aspect in which the electrical connection portion of the oral appliance 10 is the electrode 41 and the electrical connection conductor of the body device 50 is the connection terminal 71 has been described, but the exemplary aspects are not limited thereto. Further, it is noted that a "state in which the electrical connection portion and the electrical connection conductor are electrically connected" is not limited to a state in which the electrical connection portion and the electrical connection conductor are physically in contact with each other. The "state in which the electrical connection portion and the electrical connection conductor are electrically connected" can include a state in which the electrical connection portion and the electrical connection conductor are electrically connected in a non-contact manner in an alternative aspect. For example, the electrical connection can be realized by wirelessly connecting the electrical connection portion and the electrical connection conductor using a wireless communication device such as an RFID tag.

(Modification 1)

Figure 12:
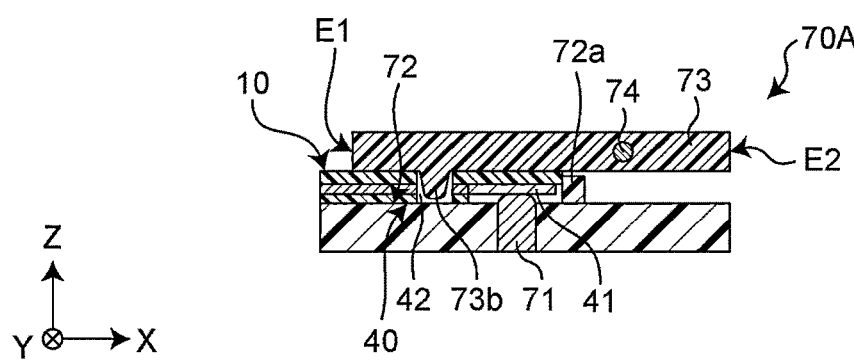
FIG. 12 is a schematic diagram illustrating an attachment/detachment operation unit of Modification 1 of an exemplary aspect.

FIG. 12 is a schematic diagram illustrating an attachment/detachment operation unit 70A of Modification 1. As illustrated in FIG. 12, a protrusion 73b can be arranged between the one end E1 of the pressing member 73 and the rotation shaft 74. Also in such a configuration, the oral appliance 10 can be more firmly fixed.

(Modification 2)

Figure 13A:
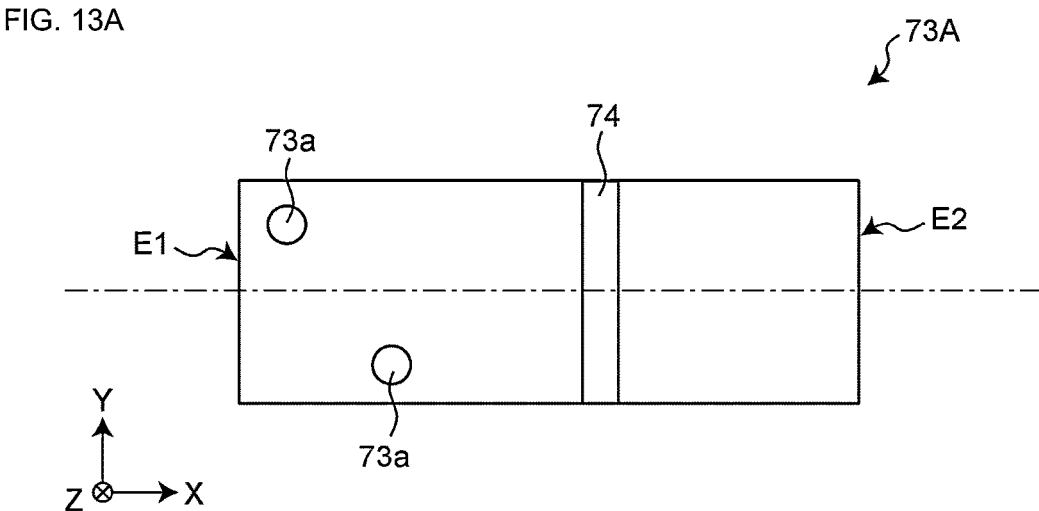
FIG. 13A is a schematic view illustrating a pressing member of Modification 2 of an exemplary aspect.
Figure 13B:
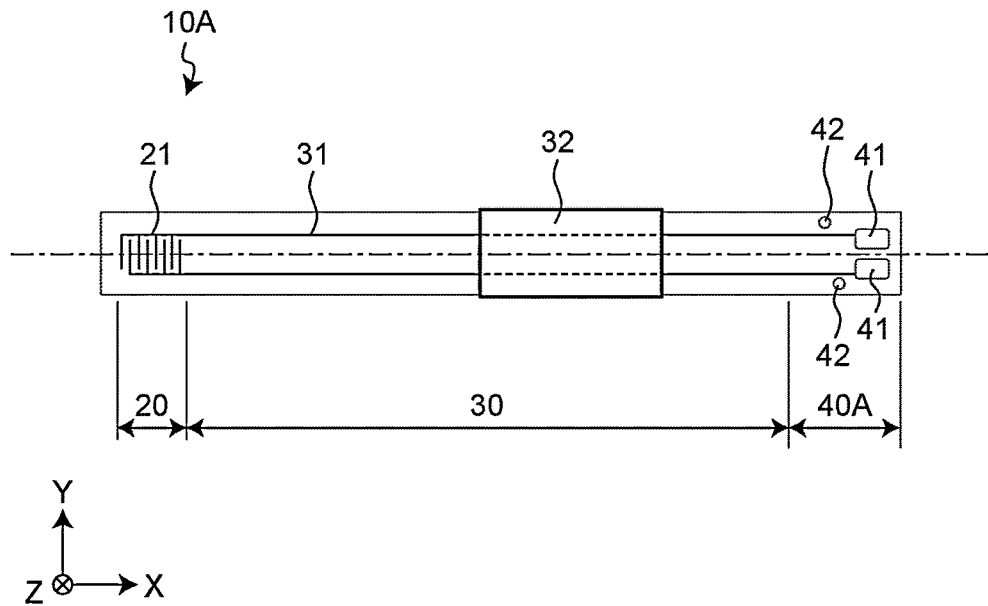
FIG. 13B is a schematic view illustrating an oral appliance of Modification 2 of an exemplary aspect.

FIG. 13A is a schematic view illustrating a pressing member 73A of Modification 2. FIG. 13B is a schematic view illustrating an oral appliance 10A of Modification 2. As illustrated in FIG. 13A, when the pressing member 73A is viewed from the Z direction, the two protrusions 73a are arranged to be bilaterally asymmetric with respect to a center line extending in the X direction. In addition, as illustrated in FIG. 13B, when the oral appliance 10A is viewed from the Z direction, the two mounting holes 42 in a connection portion 40A are arranged to be bilaterally asymmetric with respect to a center line extending in the X direction. With such a configuration, the attachment direction of the oral appliance 10A can be defined. Thus, the oral appliance 10A can be attached without making the mistake of the front surface and the back surface thereof (Modification 3)

Figure 14A:
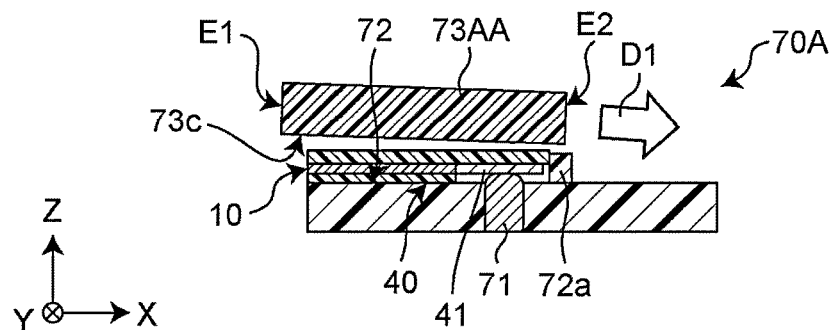
FIG. 14A is a schematic diagram illustrating an operation of an attachment/detachment operation unit of Modification 3 of an exemplary aspect.
Figure 14B:
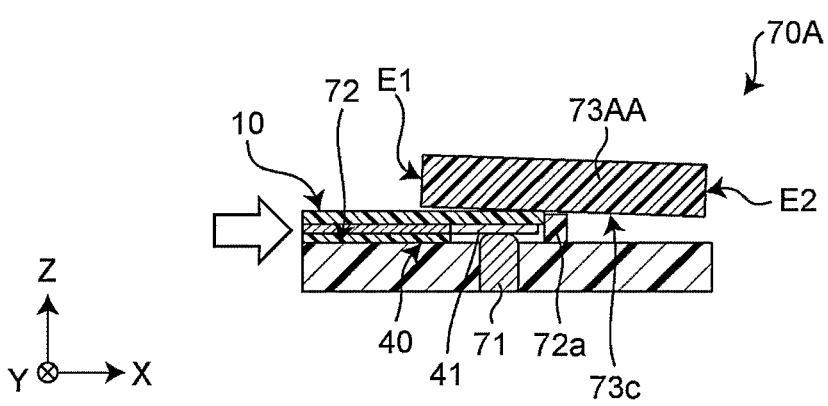
FIG. 14B is a schematic diagram illustrating the operation of the attachment/detachment operation unit of Modification 3 of an exemplary aspect.
Figure 14C:
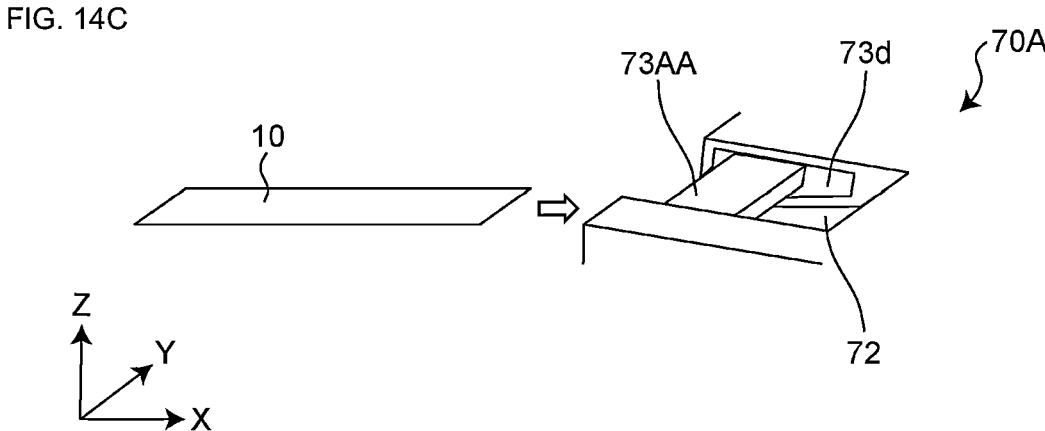
FIG. 14C is a schematic perspective view illustrating the operation of the attachment/detachment operation unit of Modification 3 of an exemplary aspect.
Figure 14D:
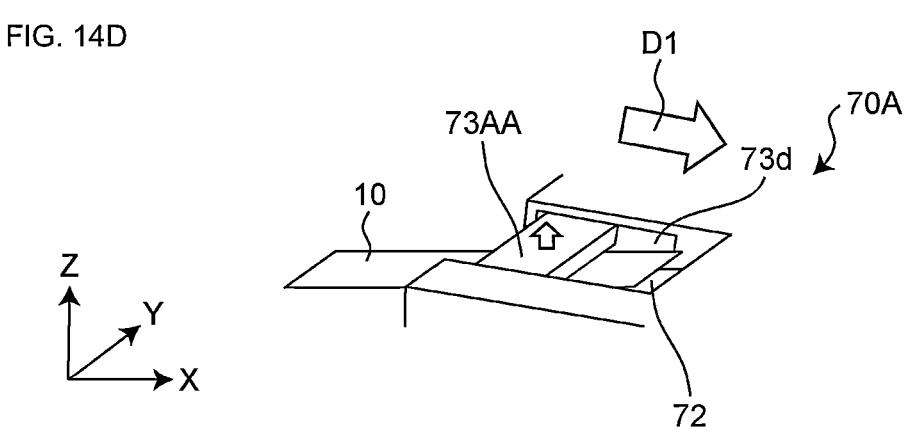
FIG. 14D is a schematic perspective view illustrating the operation of the attachment/detachment operation unit of Modification 3 of an exemplary aspect.
Figure 14E:
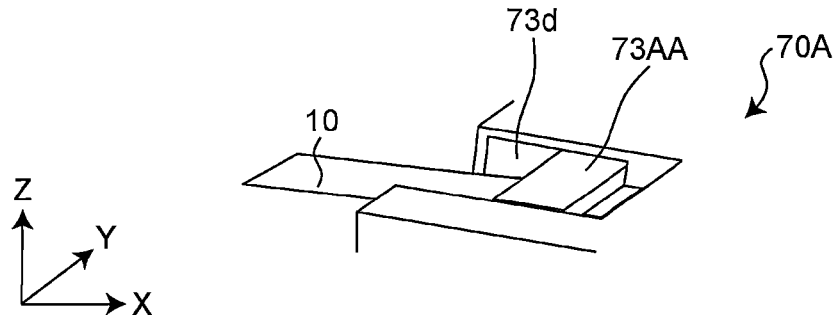
FIG. 14E is a schematic perspective view illustrating the operation of the attachment/detachment operation unit of Modification 3 of an exemplary aspect.

FIG. 14A and FIG. 14B are schematic diagrams illustrating the motion of the attachment/detachment operation unit 70A of Modification 3. FIGS. 14C to 14E are schematic perspective views illustrating the operation of the attachment/detachment operation unit 70A of Modification 3. FIGS. 14A to 14E illustrate an exemplary aspect of an attachment operation of the oral appliance 10.

In Modification 3, the attachment/detachment operation unit 70A is configured to slide a pressing member 73AA. As shown, the pressing member 73AA is formed of a plate-shaped member having the one end E1 provided on the arrangement surface 72 side and the other end E2 provided on the side opposite to the one end E1. The pressing member 73AA has a contact surface 73c that comes into contact with the oral appliance 10. For example, the contact surface 73c is a flat surface provided on the arrangement surface 72 side. The pressing member 73AA is configured to be slidable in an oblique direction with respect to the arrangement surface 72. For example, the attachment/detachment operation unit 70A includes a slide mechanism that slides the pressing member 73AA in the oblique direction with respect to the arrangement surface 72. The pressing member 73AA is inclined in a range of equal to or more than 2° and equal to or less than 20° with respect to the arrangement surface 72, for example. In addition, the pressing member 73AA is inclined in a state in which the one end E1 is lifted with respect to the body portion 60 more than the other end E2.

An exemplary aspect of the attachment operation of the oral appliance 10 on the attachment/detachment operation unit 70A in Modification 3 will be described. As illustrated in FIG. 14A, in a state in which the oral appliance 10 is arranged on the arrangement surface 72, the pressing member 73AA slides in a first oblique direction D1 from the one end E1 toward the other end E2. Accordingly, as illustrated in FIG. 14B, the pressing member 73AA comes into contact with the oral appliance 10. To be specific, the contact surface 73c of the pressing member 73AA comes into contact with the connection portion 40 of the oral appliance 10. A friction force is generated by contact between the contact surface 73c of the pressing member 73AA and the connection portion 40 of the oral appliance 10. To be specific, the pressing member 73AA slides in the first oblique direction D1 and the contact surface 73c and the connection portion 40 of the oral appliance 10 come into contact with each other, whereby the friction force is generated in a direction opposite to the direction in which the oral appliance 10 is detached. By this friction force, the oral appliance 10 can be fixed so as to be drawn toward the other end E2 side of the pressing member 73AA. Thus, the oral appliance 10 can be fixed to the body portion 60.

Next, the slide mechanism will be described. As illustrated in FIGS. 14C to 14E, the attachment/detachment operation unit 70A is provided with a slide groove 73d into which both side ends of the pressing member 73AA are inserted as the slide mechanism. FIGS. 14C to 14E are a schematic perspective view illustrating the operation of the attachment/detachment operation unit of Modification 3. The slide groove 73d is a concave groove extending in the X direction of the body device 50. A width of the slide groove 73d becomes smaller toward the attachment direction of the oral appliance 10, that is, an insertion direction (X direction). The width of the slide groove 73d is a length in the Z direction in FIGS. 14C to 14E. For example, when the body device 50 is viewed from the Y direction, an upper side of the slide groove 73d extends obliquely with respect to the arrangement surface 72, whereas a lower side of the slide groove 73d extends parallel to the arrangement surface 72. Further, in FIGS. 14C to 14E, a width on the left end side of the slide groove 73d on which the pressing member 73AA is positioned is larger than a thickness of the pressing member 73AA. Therefore, when the pressing member 73AA is positioned on the left end side of the slide groove 73d, the pressing member 73AA can move in the vertical direction (Z direction).

As illustrated in FIG. 14C, the oral appliance 10 is inserted along the arrangement surface 72 of the attachment/detachment operation unit 70A. At this time, the pressing member 73AA is positioned on the left end side of the slide groove 73d. As illustrated in FIG. 14D, when the oral appliance 10 is arranged on the arrangement surface 72, the pressing member 73AA is pushed upward. In this state, the pressing member 73AA is slid in the first oblique direction D1. To be specific, the pressing member 73AA is moved from the left end toward the right end of the slide groove 73d. At this time, the pressing member 73AA slides along the upper side of the slide groove 73d. The upper side of the slide groove 73d extends obliquely with respect to the arrangement surface 72. Therefore, the pressing member 73AA slides toward the first oblique direction D1 which is an oblique direction with respect to the arrangement surface 72. As illustrated in FIG. 14E, the pressing member 73AA is arranged at the right end of the slide groove 73d to thereby fix the oral appliance 10.

Figure 15A:
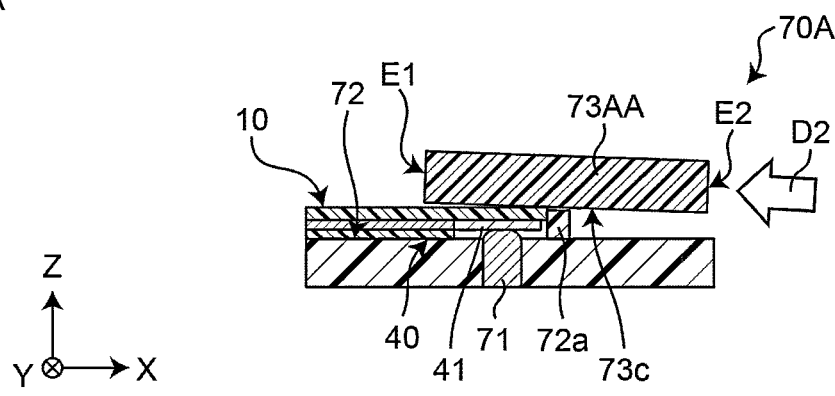
FIG. 15A is a schematic diagram illustrating the operation of the attachment/detachment operation unit of Modification 3 of an exemplary aspect.
Figure 15B:
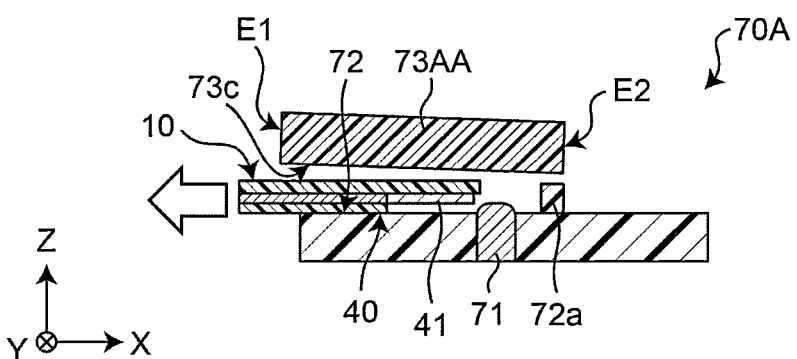
FIG. 15B is a schematic diagram illustrating the operation of the attachment/detachment operation unit of Modification 3 of an exemplary aspect.

An exemplary aspect of the detachment operation of the oral appliance 10 from the attachment/detachment operation unit 70A in Modification 3 will be described. FIGS. 15A and 15B illustrate an exemplary aspect of a removal operation of the oral appliance 10. As illustrated in FIG. 15A, the pressing member 73AA slides in a second oblique direction D2 opposite to the first oblique direction D1. The second oblique direction D2 is a direction from the other end E2 toward the one end E1 of the pressing member 73AA. As illustrated in FIG. 15B, by sliding of the pressing member 73AA in the second oblique direction D2, the contact between the contact surface 73c of the pressing member 73AA and the connection portion 40 of the oral appliance 10 is released while pushing out the oral appliance 10 in the detaching direction. As a result, the fixation of the oral appliance 10 is released, and the oral appliance 10 can be easily detached. Further, since the oral appliance 10 can be pushed out in the detaching direction by the pressing member 73AA, the user can detach the oral appliance 10 by the operation of the attachment/detachment operation unit 70A without touching the oral appliance 10.

Figure 15C:
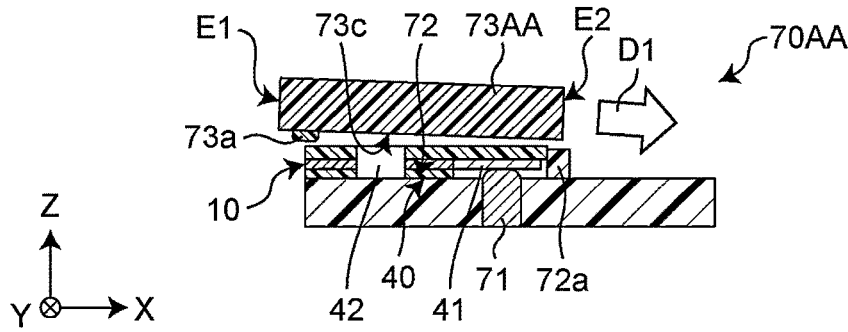
FIG. 15C is a schematic diagram illustrating the operation of another attachment/detachment operation unit of Modification 3 of an exemplary aspect.
Figure 15D:
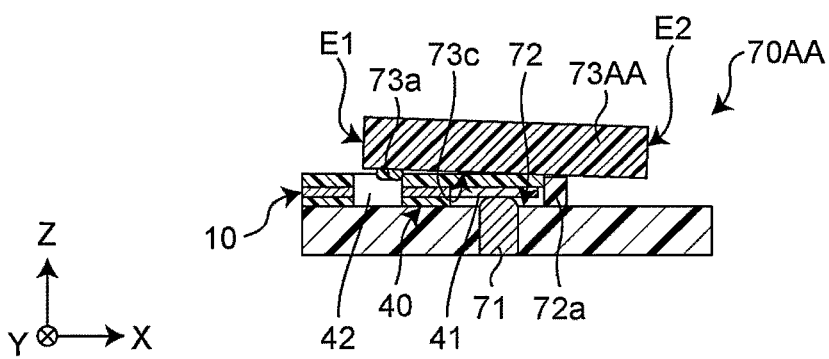
FIG. 15D is a schematic diagram illustrating the operation of the other attachment/detachment operation unit of Modification 3 of an exemplary aspect.

It is noted that in Modification 3, the pressing member 73AA can have a protrusion protruding from the contact surface 73c toward the arrangement surface 72. FIG. 15C and FIG. 15D are schematic diagrams illustrating an operation of another attachment/detachment operation unit of Modification 3.

As illustrated in FIG. 15C, the pressing member 73AA can have the protrusion 73a protruding from the contact surface 73c toward the arrangement surface 72. As illustrated in FIG. 15D, the protrusion 73a can be inserted into the mounting hole 42 of the oral appliance 10. Accordingly, the oral appliance 10 can be more firmly fixed.

(Modification 4)

Figure 15E:
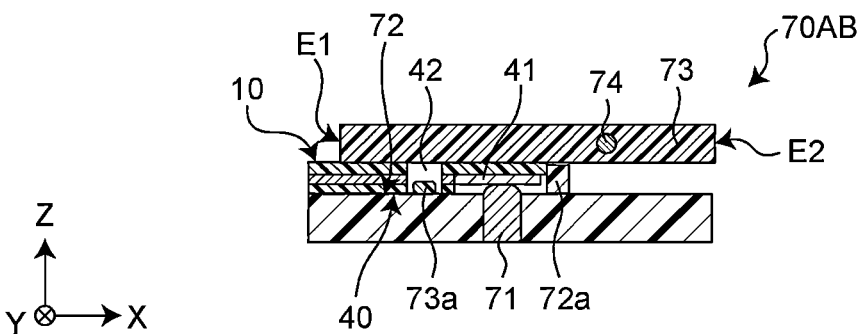
FIG. 15E is a schematic diagram illustrating an attachment/detachment operation unit of Modification 4 of an exemplary aspect.

FIG. 15E is a schematic diagram illustrating an attachment/detachment operation unit 70AB of Modification 4. As illustrated in FIG. 15E, in the attachment/detachment operation unit 70AB, the protrusion 73a can be provided on the arrangement surface 72. Note that the attachment/detachment operation unit 70AB has the same configuration as the attachment/detachment operation unit 70 of Embodiment 1 except for the position of the protrusion 73a. Also in such a configuration, it is possible to prevent the oral appliance 10 from moving in the detaching direction. Accordingly, the oral appliance 10 can be more firmly fixed.

(Modification 5)

Figure 15F:
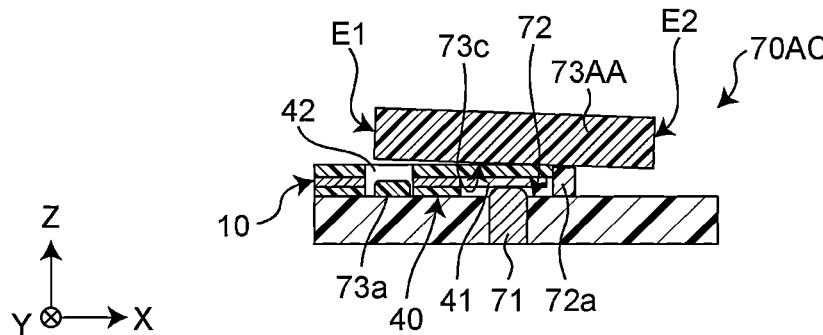
FIG. 15F is a schematic diagram illustrating an attachment/detachment operation unit of Modification 5 of an exemplary aspect.

FIG. 15F is a schematic diagram illustrating an attachment/detachment operation unit 70AC of Modification 5. As illustrated in FIG. 15F, in the attachment/detachment operation unit 70AC, the protrusion 73a can be provided on the arrangement surface 72. Note that the attachment/detachment operation unit 70AC has the same configuration as that of another attachment/detachment operation unit 70AA of Modification 3 except for the position of the protrusion 73a. Also in such a configuration, it is possible to prevent the oral appliance 10 from moving in the detaching direction. Accordingly, the oral appliance 10 can be more firmly fixed.

Exemplary Embodiment 2

An oral device according to Embodiment 2 of the present invention will be described. Note that in Embodiment 2, differences from Embodiment 1 will be mainly described. In Embodiment 2, configurations identical or equivalent to those in Embodiment 1 are denoted by the same reference numerals and are described. Further, in Embodiment 2, the description overlapping with Embodiment 1 will be omitted.

Figure 16:
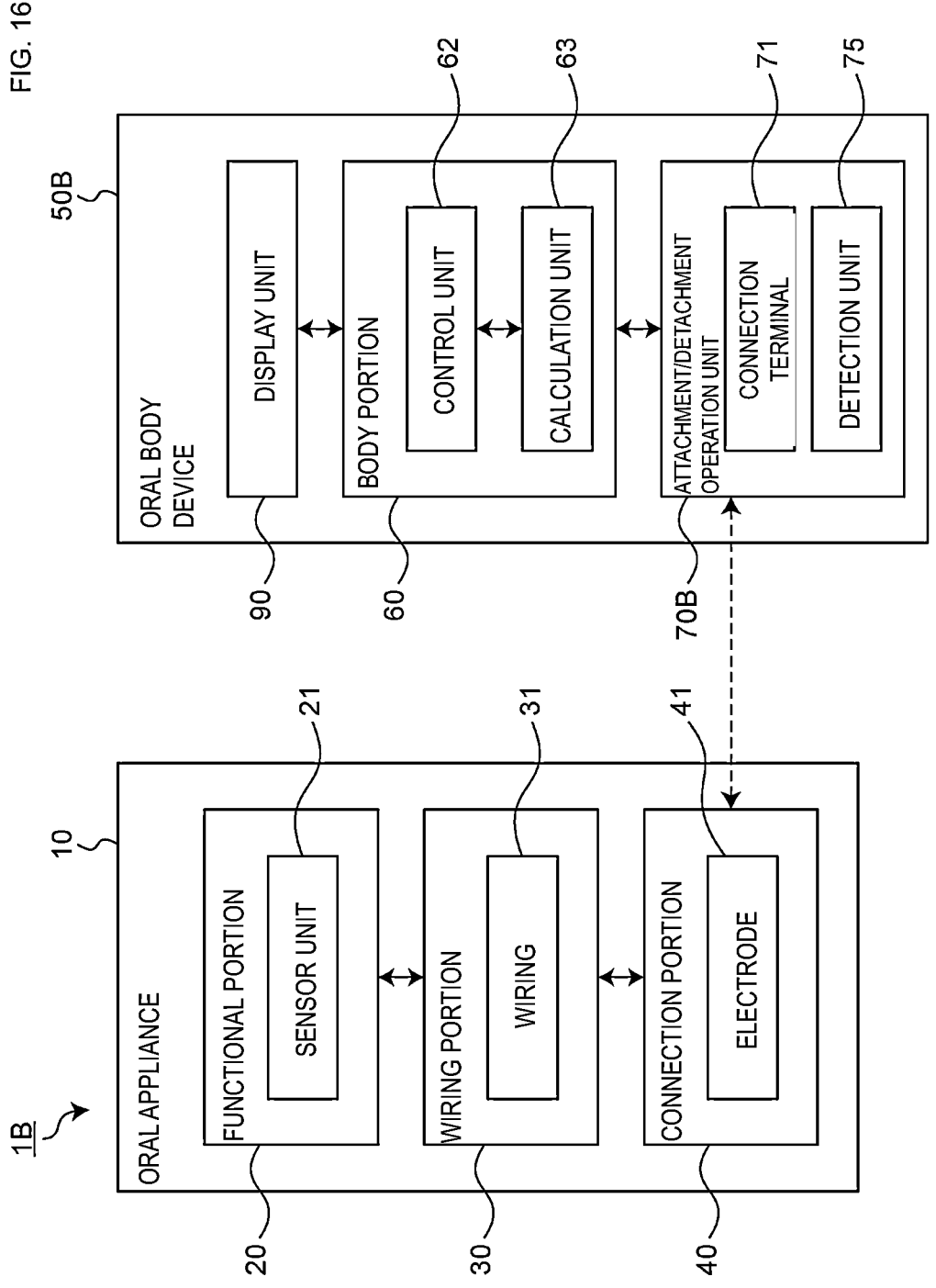
FIG. 16 is a block diagram illustrating a main configuration of an exemplary aspect of an oral device of Embodiment 2.

An exemplary aspect of the oral device of Embodiment 2 will be described with reference to FIG. 16. FIG. 16 is a block diagram illustrating a main configuration of an exemplary aspect of an oral device 1B of Embodiment 2.

It should be appreciated that Embodiment 2 is different from Embodiment 1 in that an oral body device 50B includes a detection unit 75.

As illustrated in FIG. 16, an attachment/detachment operation unit 70B of the oral body device 50B includes the detection unit 75. The detection unit 75 detects whether or not the oral appliance 10 is attached to the attachment/detachment operation unit 70B. Detection by the detection unit 75 will be described later. Information on the detection result of the detection unit 75 is transmitted to the control unit 62.

The control unit 62 determines whether or not use of the oral appliance 10 is possible (e.g., the available operational state of the oral appliance 10) based on the detection result of the detection unit 75. To be specific, the control unit 62 stops the use of the oral appliance 10 after the oral appliance 10 is used in a state of being attached to the attachment/detachment operation unit 70B. When the detection unit 75 detects that the used oral appliance 10 has been detached and that an unused oral appliance 10 has been attached, the control unit 62 enables the use of the unused oral appliance 10. Further, the control unit 62 transmits information on whether or not the use of the oral appliance 10 is possible to the display unit 90.

Stopping the use of the oral appliance 10 includes, for example, disabling the operation of the body device 50B.

The control unit 62 determines whether or not the oral appliance 10 attached to the attachment/detachment operation unit 70B has been used. Specifically, the control unit 62 determines whether the oral appliance 10 has been used or has not been used based on the information acquired by the oral appliance 10. For example, the control unit 62 can determine whether or not the oral appliance 10 has been used based on information on whether or not the calculation process of the amount of moisture has been performed by the calculation unit 63. After performing the calculation process, the calculation unit 63 transmits calculation process completion flag information to the control unit 62. Upon receiving the calculation process completion flag information, the control unit 62 determines that the oral appliance 10 has been used. Note that the determination of whether the oral appliance 10 has been used or has not been used is not limited thereto. The determination of whether the oral appliance 10 has been used or has not been used can be based on other information.

When the control unit 62 determines that the oral appliance 10 has been used, the control unit 62 stops the use of the oral appliance 10. In addition, the control unit 62 transmits information indicating that the use of the oral appliance 10 is stopped to the display unit 90.

After stopping the use of the oral appliance 10, the control unit 62 enables the use of the unused oral appliance 10 when the detection unit 75 detects that the used oral appliance 10 has been detached and that the unused oral appliance 10 has been attached.

When the detection unit 75 detects that the used oral appliance 10 has been detached, the control unit 62 clears the calculation process completion flag information. Thus, the body device 50B stands by until the unused oral appliance 10 is attached to the attachment/detachment operation unit 70B.

When the detection unit 75 detects that the unused oral appliance 10 is attached to the attachment/detachment operation unit 70B, the control unit 62 enables the use of the oral appliance 10. In addition, the control unit 62 transmits information indicating that the use of the oral appliance 10 is possible to the display unit 90.

The display unit 90 displays information on whether or not the use of the oral appliance 10 is possible. The information on whether or not the use of the oral appliance is possible includes information indicating that the use of the oral appliance 10 is stopped and information indicating that the use of the oral appliance 10 is possible. For example, the information indicating that the use of the oral appliance 10 has been stopped can be a message prompting replacement of the used oral appliance 10. The information indicating that the use of the oral appliance 10 is possible can be to stop displaying the message.

Note that in Embodiment 2, an exemplary aspect in which the control unit 62 stops the use of the oral appliance 10 after the oral appliance 10 is used in a state of being attached to the attachment/detachment operation unit 70B has been described, but the exemplary aspects are not limited thereto. For example, control unit 62 does not have to stop the use of the oral appliance 10. The control unit 62 can determine whether or not the use of the oral appliance 10 is possible without stopping the use of the oral appliance 10, and can cause the display unit 90 to display information on the determination result of whether or not the use of the oral appliance 10 is possible. For example, in a case where the control unit 62 determines that the oral appliance 10 has been used, the control unit 62 can cause the display unit 90 to display a replacement message without stopping the use of the oral appliance 10.

Figure 17A:
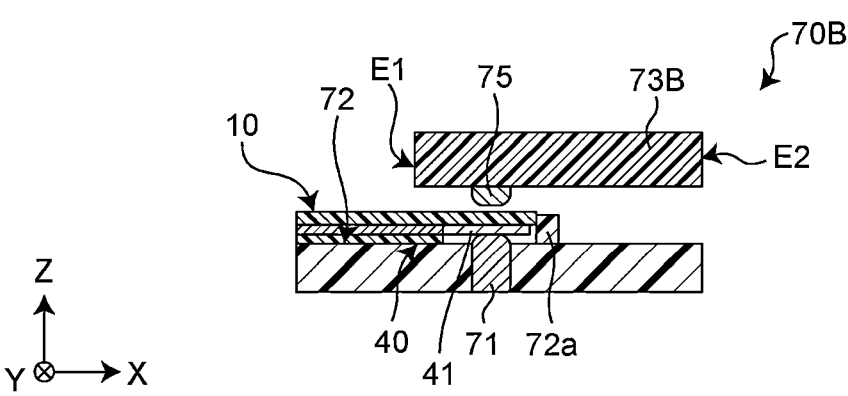
FIG. 17A is a schematic diagram illustrating an exemplary aspect of a motion of a detection unit.
Figure 17B:
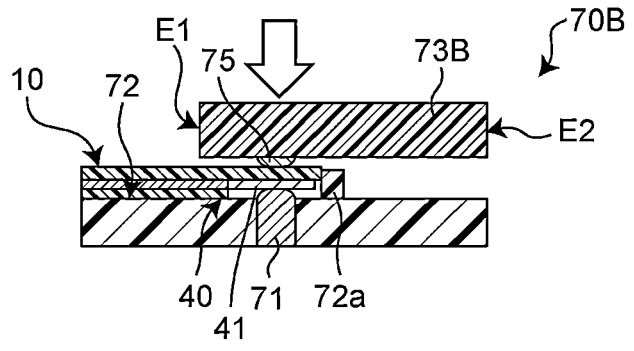
FIG. 17B is a schematic diagram illustrating an exemplary aspect of the motion of the detection unit.
Figure 17C:
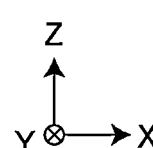
FIG. 17C is a schematic diagram illustrating an exemplary aspect of the motion of the detection unit.
Figure 17C:
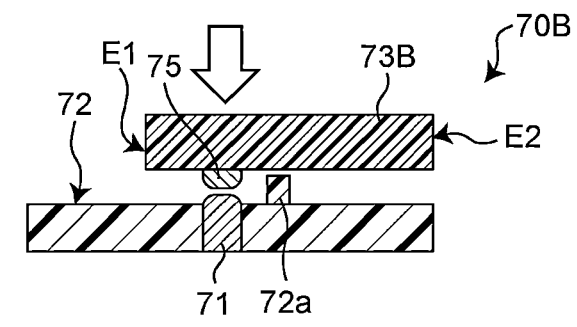

The detection unit 75 will be described with reference to FIGS. 17A to 17C. FIGS. 17A to 17C are schematic diagrams illustrating an exemplary aspect of the motion of the detection unit. As illustrated in FIGS. 17A and 17C, the detection unit 75 comprises a switch. For example, the detection unit 75 is a push-type switch. The push-type switch is turned on when the switch is pushed, and turned off when the switch is not pushed.

The detection unit 75 is arranged on a pressing member 73B. To be specific, the detection unit 75 is arranged on the arrangement surface 72 side of the pressing member 73B. In addition, the detection unit 75 is arranged on the one end E1 side of the pressing member 73B. The detection unit 75 is arranged at a position in physical contact with the connection portion 40 of the oral appliance 10 arranged on the arrangement surface 72.

As illustrated in FIG. 17B, in a case where the oral appliance 10 is arranged on the arrangement surface 72, when pressing against the pressing member 73B toward the arrangement surface 72, the detection unit 75 comes into physical contact with the oral appliance 10. Accordingly, the switch of the detection unit 75 is turned on. When the switch is turned on, the detection unit 75 detects that the oral appliance 10 is attached to the attachment/detachment operation unit 70B.

As illustrated in FIG. 17C, in a case where the oral appliance 10 is not arranged on the arrangement surface 72, even when pressing against the pressing member 73B toward the arrangement surface 72, the detection unit 75 does not come into physical contact with the oral appliance 10. Therefore, the switch of the detection unit 75 remains OFF. When the switch is OFF, the detection unit 75 detects that the oral appliance 10 is detached from the attachment/detachment operation unit 70B.

[Effects]

According to the oral body device 50B according to Embodiment 2, the following effects can be achieved.

The oral body device 50B includes the detection unit 75 that detects whether or not the oral appliance 10 is attached to the attachment/detachment operation unit 70B. The control unit 62 determines whether or not the use of the oral appliance 10 is possible on the detection result of the detection unit 75. The control unit 62 determines whether or not the oral appliance 10 attached to the attachment/detachment operation unit 70B has been used. In a case where the oral appliance 10 is determined to have been used, the control unit 62 determines that the use of the oral appliance 10 is not possible. After it is determined that the use of the oral appliance 10 is not possible, the control unit 62 determines that the use of the oral appliance 10 is possible when the detection unit 75 detects that the used oral appliance 10 has been detached and that the unused oral appliance 10 has been attached.

With such a configuration, it is possible to easily determine whether or not the use of the oral appliance 10 is possible, e.g., the operational state of the oral appliance 10. Thus, reuse of the oral appliance 10 can be prevented.

The display unit 90 displays information on whether or not the use of the oral appliance 10 is possible. With such a configuration, the user can easily know whether or not the oral appliance 10 has been used.

In a case where the oral appliance 10 is determined to have been used, the control unit 62 stops the use of the oral appliance 10. The control unit 62 enables the use of the oral appliance 10 based on the determination that the use of the oral appliance 10 is possible. With such a configuration, it is possible to prevent the user from using the used oral appliance 10 again.

Note that in Embodiment 2, an exemplary aspect has been described in which the display unit 90 displays information indicating whether or not the use of the oral appliance 10 is possible in the body device 50B, but the exemplary aspects are not limited thereto. In the body device 50B, it is not an essential configuration for the display unit 90 to display information on whether or not the use of the oral appliance 10 is possible.

In Embodiment 2, an exemplary aspect in which the display unit 90 displays a message prompting replacement of the used oral appliance 10 has been described, but the exemplary aspects are not limited thereto. For example, the display unit 90 can display a message indicating that it has been used or has not been used. Alternatively, the display unit 90 can indicate information by light, color, sound, or the like.

In Embodiment 2, an exemplary aspect in which the detection unit 75 is configured by a push-type switch has been described, but the exemplary aspects are not limited thereto. The detection unit 75 only needs to have a configuration configured to detect whether or not the oral appliance 10 is attached to the attachment/detachment operation unit 70B. For example, the detection unit 75 can be a sensor such as an electrostatic capacity sensor. In this case, the detection unit 75 can detect attachment/detachment of the oral appliance 10 based on a change in electrostatic capacity.

Alternatively, the detection unit 75 can detect whether or not the oral appliance 10 is attached to the attachment/detachment operation unit 70B based on the information acquired by the oral appliance 10. For example, the detection unit 75 can detect whether or not the oral appliance 10 is attached to the attachment/detachment operation unit 70B based on the electrostatic capacity acquired by the oral appliance and thresholds. In this case, the detection unit 75 can be included in the calculation unit 63. With such a configuration, the number of mechanical components for detection can be reduced, and the cost can be reduced.

In Embodiment 2, an exemplary aspect in which the detection unit 75 is arranged on the pressing member 73B has been described, but the exemplary aspects are not limited thereto. The detection unit 75 only needs to be arranged at a position where the attachment/detachment of the oral appliance 10 can be detected. For example, the detection unit 75 can be arranged on the arrangement surface 72.

(Modification 6)

Figure 18A:
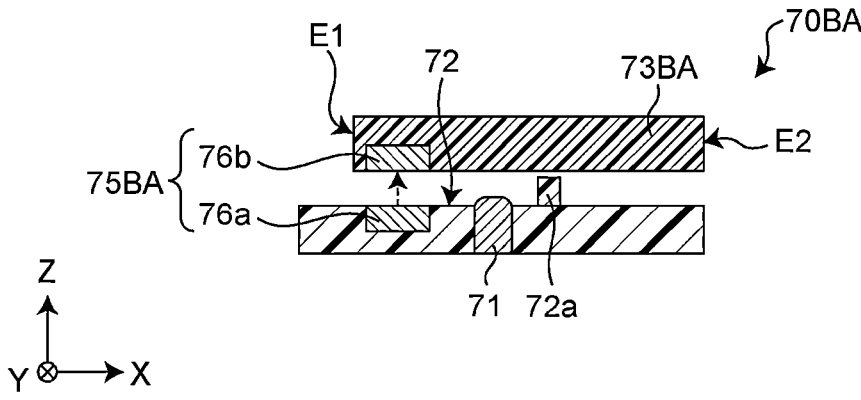
FIG. 18A is a schematic diagram illustrating a motion of a detection unit of Modification 6 of an exemplary aspect.
Figure 18B:
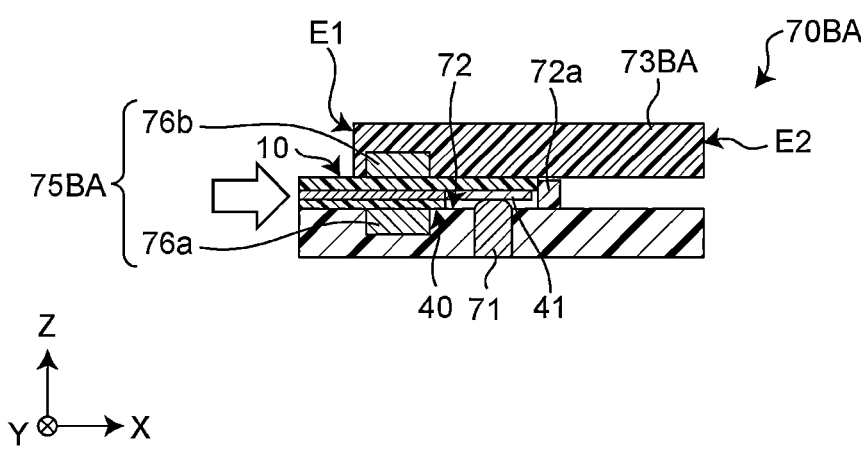
FIG. 18B is a schematic diagram illustrating the motion of the detection unit of Modification 6 of an exemplary aspect.

FIG. 18A and FIG. 18B are schematic diagrams illustrating the motion of a detection unit 75BA of Modification 6. As illustrated in FIG. 18A and FIG. 18B, the detection unit 75BA can be formed by a photosensor. A detection unit 75BA includes a light emitting portion 76a that emits light and a light receiving portion 76b that receives light.

In an attachment/detachment operation unit 70BA, the light emitting portion 76a is arranged on the arrangement surface 72. To be specific, the light emitting portion 76a is arranged in a hole provided in the arrangement surface 72. The light emitting portion 76a emits light toward the light receiving portion 76b.

In the attachment/detachment operation unit 70BA, the light receiving portion 76b is arranged on a pressing member 73BA. To be specific, the light receiving portion 76b is arranged on the arrangement surface 72 side of the pressing member 73BA. In addition, the light receiving portion 76b is arranged on an optical axis of the light emitted by the light emitting portion 76a. In other words, the light receiving portion 76b is arranged above the light emitting portion 76a.

As illustrated in FIG. 18A, when the oral appliance 10 is not arranged on the arrangement surface 72, the light emitted from the light emitting portion 76a is received by the light receiving portion 76b. When the light receiving portion 76b receives the light from the light emitting portion 76a, the detection unit 75BA detects that the oral appliance 10 is detached from the attachment/detachment operation unit 70BA.

As illustrated in FIG. 18B, when the oral appliance 10 is arranged on the arrangement surface 72, the light emitted from the light emitting portion 76a is blocked by the oral appliance 10. Therefore, the light receiving portion 76b does not receive light from the light emitting portion 76a. When the light receiving portion 76b does not receive light from the light emitting portion 76a, the detection unit 75BA detects that the oral appliance 10 is attached to the attachment/detachment operation unit 70BA.

Note that in Modification 6, the oral appliance 10 can be formed of an absorbing material that absorbs light or a light shielding material that blocks light. Such a configuration enables the oral appliance 10 to absorb or block light emitted from the light emitting portion 76a. Therefore, detection accuracy can be improved.

(Modification 7)

Figure 19A:
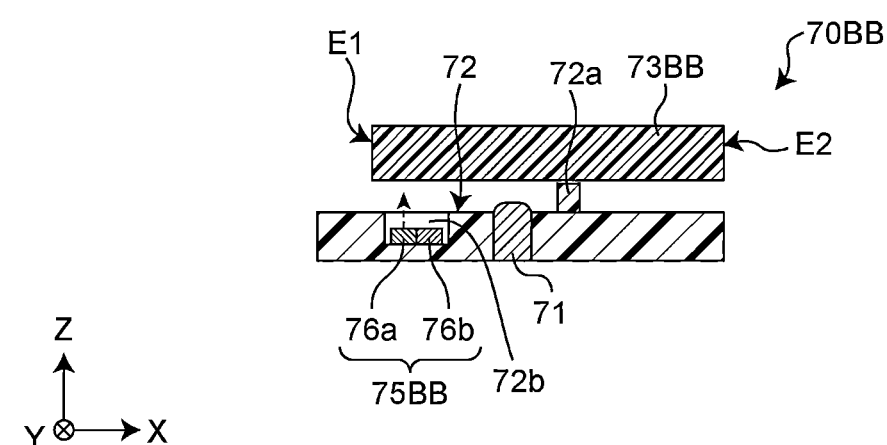
FIG. 19A is a schematic diagram illustrating a motion of a detection unit of Modification 7 of an exemplary aspect.
Figure 19B:
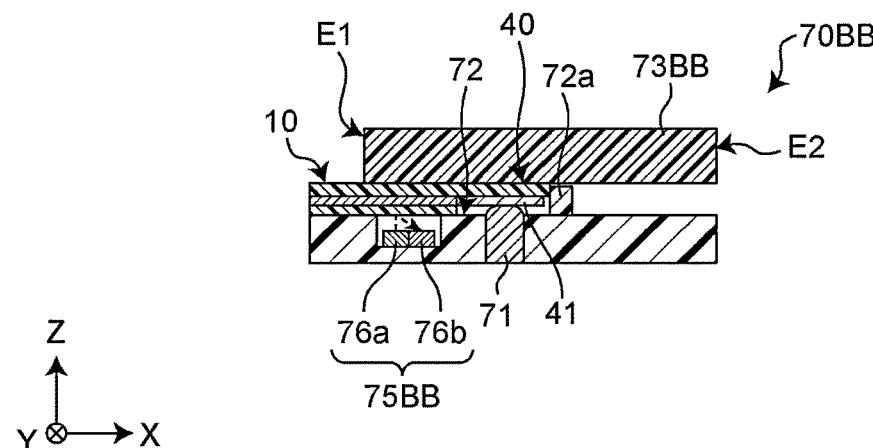
FIG. 19B is a schematic diagram illustrating the motion of the detection unit of Modification 7 of an exemplary aspect.

FIG. 19A and FIG. 19B are schematic diagrams illustrating the motion of a detection unit 75BB of Modification 7. As illustrated in FIG. 19A and FIG. 19B, the detection unit 75BB can be configured by a photosensor as in Modification 6. The detection unit 75BB includes the light emitting portion 76a that emits light and the light receiving portion 76b that receives light.

In the attachment/detachment operation unit 70BB, the light emitting portion 76a and the light receiving portion 76b are arranged on the arrangement surface 72. To be specific, the light emitting portion 76a and the light receiving portion 76b are arranged side by side in a hole provided in the arrangement surface 72. The light emitting portion 76a emits light toward a pressing member 73BB. The light receiving portion 76b receives light emitted from the light emitting portion 76a and reflected by the oral appliance 10.

As illustrated in FIG. 19A, when the oral appliance 10 is not arranged on the arrangement surface 72, the light emitted from the light emitting portion 76a is not reflected by the oral appliance 10. Therefore, the light receiving portion 76b does not receive light. When the light receiving portion 76b does not receive the light from the light emitting portion 76a, the detection unit 75BB detects that the oral appliance 10 is detached from the attachment/detachment operation unit 70BB.

As illustrated in FIG. 19B, when the oral appliance 10 is arranged on the arrangement surface 72, the light emitted from the light emitting portion 76a is reflected by the oral appliance 10. Therefore, the light receiving portion 76b receives the light reflected by the oral appliance 10. When the light receiving portion 76b receives the reflection light from the oral appliance 10, the detection unit 75BB detects that the oral appliance 10 is attached to the attachment/detachment operation unit 70BB.

Note that in Modification 7, the oral appliance 10 can be formed of a reflective material that reflects light. Such a configuration enables light emitted from the light emitting portion 76a by the oral appliance 10 to be reflected. Therefore, the detection accuracy can be improved.

Exemplary Embodiment 3

An oral device according to Embodiment 3 of the present invention will be described. It is noted that in Embodiment 3, differences from Embodiment 1 will be mainly described. In Embodiment 3, configurations identical or equivalent to those in Embodiment 1 are denoted by the same reference numerals and are described. Further, in Embodiment 3, the description overlapping with Embodiment 1 will be omitted.

Figure 20A:
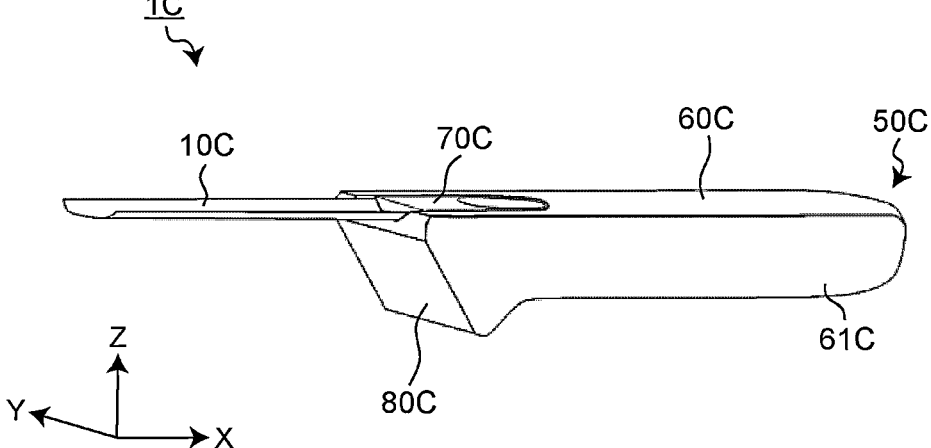
FIG. 20A is a schematic perspective view of an exemplary aspect of an oral device of Embodiment 3.
Figure 20B:
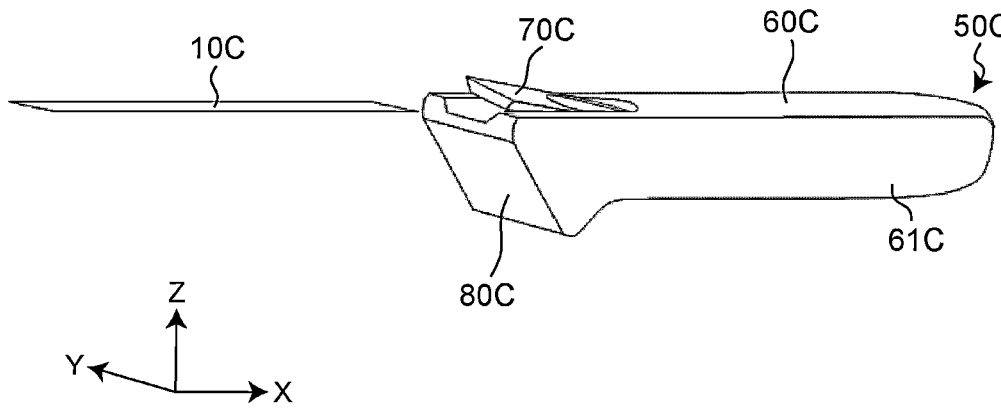
FIG. 20B is a schematic perspective view of an exemplary aspect of the oral device of Embodiment 3.

An exemplary aspect of the oral device of Embodiment 3 will be described with reference to FIG. 20A and FIG. 20B. FIG. 20A and FIG. 20B are schematic perspective views of an exemplary aspect of an oral device 1C of Embodiment 3. Note that in FIG. 20A and FIG. 20B, the display of the display unit 90 is omitted.

Embodiment 3 is different from Embodiment 1 in that a direction in which a body portion 60C of an oral body device 50C extends is the same as the attachment/detachment direction of the oral appliance 10C, and that an attachment/detachment operation unit 70C is configured to deform and fix the oral appliance 10C.

As illustrated in FIG. 20A and FIG. 20B, the body portion 60C of the oral body device 50C is formed of a rod-shaped member extending in the same direction as the attachment/detachment direction of the oral appliance 10C. The attachment/detachment direction of the oral appliance 10C is the X direction in FIG. 20A and FIG. 20B.

A guard 80C is formed by a convex portion that protrudes in a direction intersecting the attachment/detachment direction of the oral appliance 10C. The guard 80C is provided on the side opposite to the side on which the attachment/detachment operation unit 70C is provided in the body portion 60C. The guard 80C protrudes outer side portion relative to a grip portion 61C. In addition, an inclined surface that prevents liquid such as saliva from flowing toward the grip portion 61C is formed on the guard 80C. Accordingly, it is possible to prevent saliva from flowing to the grip portion 61C.

The oral appliance 10C is formed in a sheet shape that is deformable in the longitudinal direction. In Embodiment 3, the entire oral appliance 10C has flexibility. The attachment/detachment operation unit 70C is configured to deform and fix the oral appliance 10C.

The attachment/detachment operation unit 70C includes an arrangement surface 72C that is curved in a concave shape or a convex shape, and a pressing member 73C that is curved in a concave shape or a convex shape along the shape of the arrangement surface 72C.

Figure 21A:
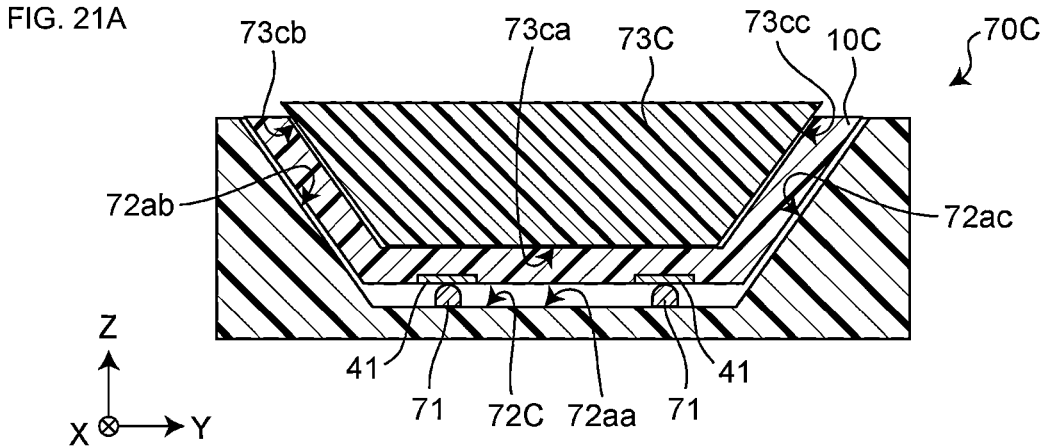
FIG. 21A is a schematic partially enlarged cross-sectional view illustrating an exemplary aspect of an attachment/detachment operation unit in an enlarged manner.
Figure 21B:
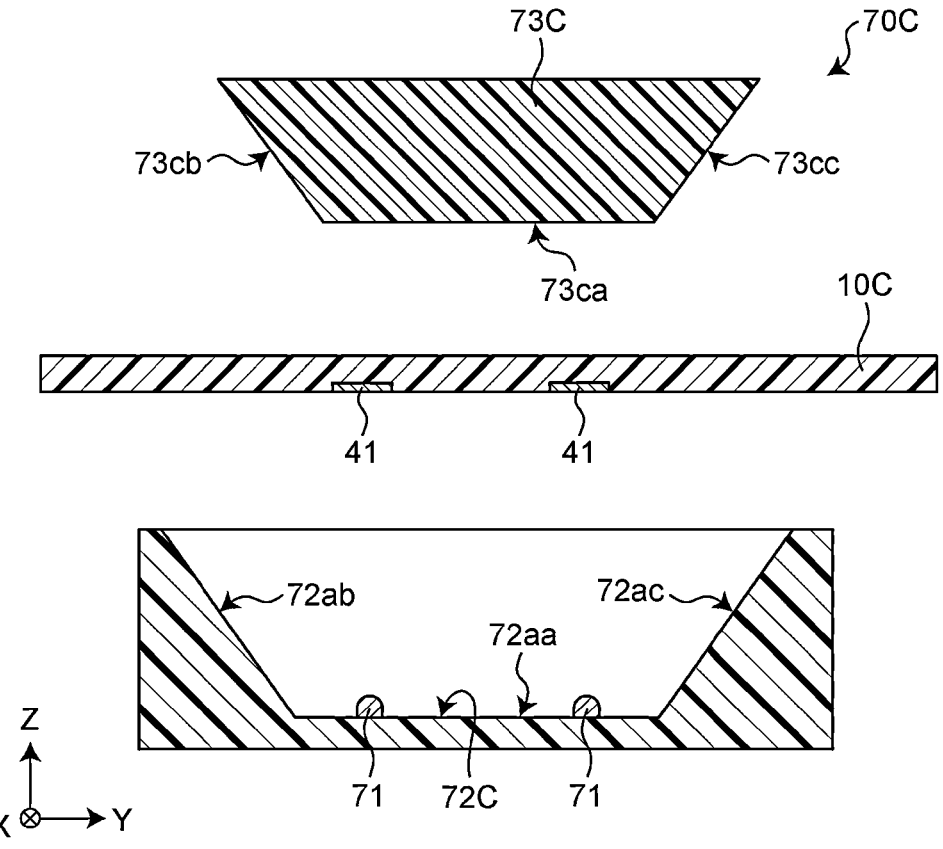
FIG. 21B is a schematic exploded cross-sectional view of the attachment/detachment operation unit of FIG. 21A.

An exemplary aspect of the attachment/detachment operation unit 70C will be described with reference to FIG. 21A and FIG. 21B. FIG. 21A is a schematic partially enlarged cross-sectional view illustrating an exemplary aspect of the attachment/detachment operation unit 70C in an enlarged manner. FIG. 21B is a schematic exploded cross-sectional view of the attachment/detachment operation unit of FIG. 21A. Note that FIG. 21A and FIG. 21B are cross-sectional views of the attachment/detachment operation unit 70C taken along a YZ plane.

As illustrated in FIG. 21A and FIG. 21B, the arrangement surface 72C is formed to be curved in a concave shape. To be specific, the arrangement surface 72C is formed to be recessed in a trapezoidal shape. The arrangement surface 72C includes a flat bottom surface 72aa and a plurality of inclined surfaces 72ab and 72ac extending at an angle toward the bottom surface 72aa. The plurality of connection terminals 71 is arranged on the bottom surface 72aa of the arrangement surface 72C.

The pressing member 73C is formed so as to be convexly curved along the shape of the arrangement surface 72C. In particular, the pressing member 73C is formed in a trapezoidal shape. The pressing member 73C includes a flat bottom surface 73ca and a plurality of inclined surfaces 73cb and 73cc inclined and extending toward the bottom surface 73ca.

As illustrated in FIG. 21A, the oral appliance 10C is attached to the attachment/detachment operation unit 70C by pressing against the oral appliance 10C arranged on the arrangement surface 72C by the pressing member 73C. The oral appliance 10C is fixed in a deformed state along the shapes of the pressing member 73C and the arrangement surface 72C by being sandwiched between the pressing member 73C and the arrangement surface 72C. In Embodiment 3, the oral appliance 10C is deformed into a trapezoidal shape protruding downward in the Z direction.

To be specific, the oral appliance 10C is sandwiched between the bottom surface 72aa of the arrangement surface 72C and the bottom surface 73ca of the pressing member 73C, between the inclined surface 72ab of the arrangement surface 72C and an inclined surface 73cb of the pressing member 73C, and between the inclined surface 72ac of the arrangement surface 72C and an inclined surface 73cc of the pressing member 73C.

The plurality of electrodes 41 of the oral appliance 10C is electrically connected to the plurality of connection terminals 71 arranged on the bottom surface 72aa of the arrangement surface 72C by physically contacting the plurality of connection terminals 71.

Thus, the oral appliance 10C is deformed into a trapezoidal shape and fixed to the attachment/detachment operation unit 70C. In this manner, the oral appliance 10C having flexibility is deformed into a trapezoidal shape or the like and can be attached to the attachment/detachment operation unit 70C.

[Effects]

According to the oral body device 50C according to Embodiment 3, the following effects can be achieved.

In the attachment/detachment operation unit 70C of the oral body device 50C, the arrangement surface 72C is curved in a concave shape or a convex shape. The pressing member 73C is curved in a concave shape or a convex shape along the shape of the arrangement surface 72. With such a configuration, the oral appliance 10C having flexibility can be deformed and attached. Thus, the oral appliance 10C can be prevented from hanging down. For example, when saliva or the like adheres to the oral appliance 10C, the oral appliance 10C can hang down due to the weight of the saliva. By deforming the oral appliance 10C into a trapezoidal shape or the like to be attached, the oral appliance 10C can be prevented from hanging down. Meanwhile, when the oral appliance 10C is used in the oral cavity, the oral appliance 10C can be deformed along the shape of the contact site in the oral cavity. This configuration improve the measurement accuracy or radiation accuracy.

Further, the attachment/detachment operation unit 70C deforms and fixes an oral appliance 10C having flexibility. Therefore, when the force applied to the oral appliance 10C is released and the fixation is released, the oral appliance 10C can be easily detached from the attachment/detachment operation unit 70C by a restoring force of the oral appliance 10C.

Further, the arrangement surface 72C and the pressing member 73C are formed in a trapezoidal shape. The plurality of connection terminals 71 is arranged on the flat bottom surface 72aa of the arrangement surface 72C. On the bottom surface 72aa, the plurality of electrodes 41 of the oral appliance 10C and the plurality of connection terminals 71 are in physical contact with each other. This configuration enables the plurality of electrodes 41 to easily be electrically connected to the plurality of connection terminals 71.

Note that in Embodiment 3, an exemplary aspect in which the arrangement surface 72C and the pressing member 73C are formed in a trapezoidal shape has been described, but the exemplary aspects are not limited thereto. The arrangement surface 72C only needs to be curved in a concave shape or a convex shape. The pressing member 73C only needs to be curved in a concave shape or a convex shape along the shape of the arrangement surface 72. For example, the arrangement surface 72C can be formed to protrude in a trapezoidal shape, and the pressing member 73C can be formed to be recessed in a trapezoidal shape. With such a configuration, the oral appliance 10C can be easily fitted to the contact site in the oral cavity.

In Embodiment 3, an exemplary aspect in which the plurality of connection terminals 71 is arranged on the bottom surface 72aa of the arrangement surface 72C has been described, but the exemplary aspects are not limited thereto. For example, the plurality of connection terminals 71 can be arranged on the inclined surfaces 72ab and 72ac. Alternatively, the plurality of connection terminals 71 can be arranged on the bottom surface 73ca and the inclined surfaces 73cb and 73cc of the pressing member 73C.

(Modification 8)

Figure 22:
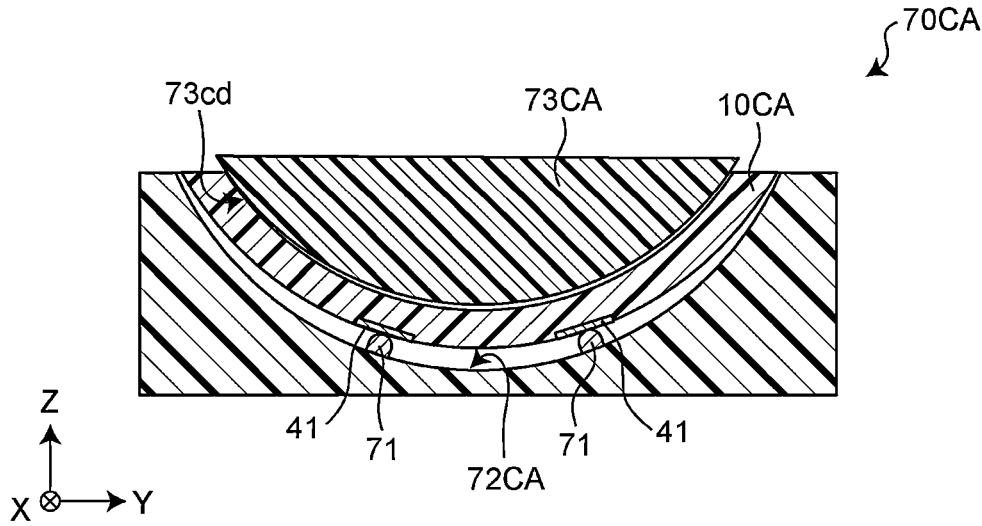
FIG. 22 is a schematic partially enlarged cross-sectional view illustrating an attachment/detachment operation unit of Modification 8 in an enlarged manner according to an exemplary aspect.

FIG. 22 is a schematic partially enlarged cross-sectional view illustrating an attachment/detachment operation unit 70CA of Modification 8 in an enlarged manner. As illustrated in FIG. 22, the attachment/detachment operation unit 70CA includes an arrangement surface 72CA recessed in a semi-circular shape and a pressing member 73CA having a semi-circular shape along the shape of the arrangement surface 72CA. The pressing member 73CA has a semi-circular surface 73cd formed in a semi-circular shape. The oral appliance 10CA is fixed in a semi-circular deformed state by being sandwiched between the arrangement surface 72CA and the semi-circular surface 73cd of the pressing member 73CA. In other words, the oral appliance 10CA is fixed in a state of being deformed into a V-shape protruding downward when viewed from the X direction by being sandwiched between an arrangement surface 72CA and semi-circular surface 73cd of a pressing member 73CA.

(Modification 9)

Figure 23:
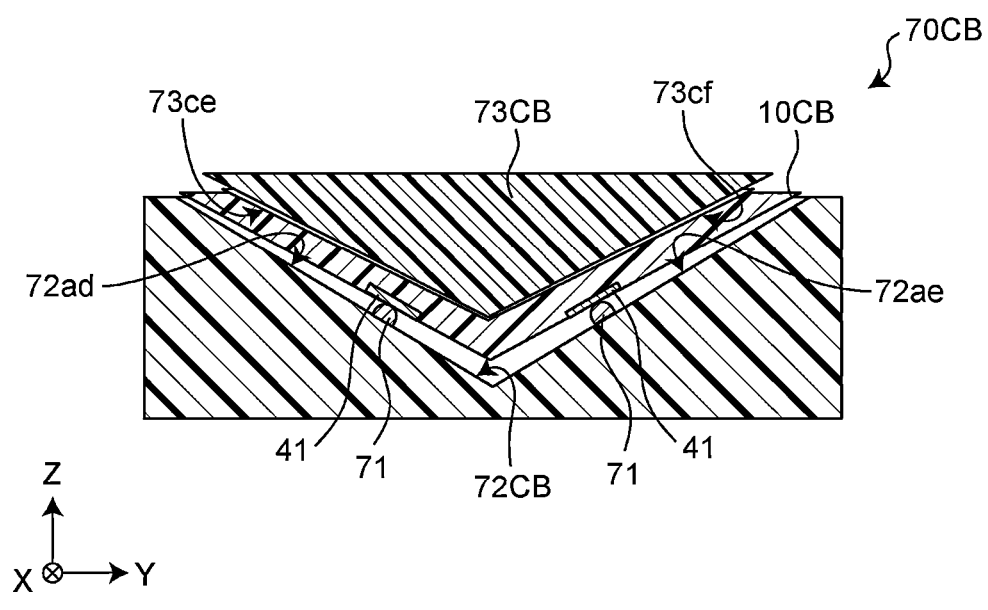
FIG. 23 is a schematic partially enlarged cross-sectional view illustrating an attachment/detachment operation unit of Modification 9 in an enlarged manner according to an exemplary aspect.

FIG. 23 is a schematic partially enlarged cross-sectional view illustrating an attachment/detachment operation unit 70CB of Modification 9 in an enlarged manner. As illustrated in FIG. 23, the attachment/detachment operation unit 70CB has the arrangement surface 72CB recessed in a triangular shape and the pressing member 73CB having a triangular shape along the shape of the arrangement surface 72CB. The arrangement surface 72CB has two inclined surfaces 72ad and 72ae. The pressing member 73CB has two inclined surfaces 73ce and 73cf The oral appliance 10CB is fixed in a state of being deformed into a triangular shape by being sandwiched between the arrangement surface 72CB and the pressing member 73CB. To be specific, the oral appliance 10CB is sandwiched between the inclined surface 72ad of the arrangement surface 72CB and an inclined surface 73ce of the pressing member 73CB, and between the inclined surface 72ae of the arrangement surface 72CB and an inclined surface 73cf of the pressing member 73CB. Accordingly, the oral appliance 10CB is fixed in a state of being deformed into a V-shape protruding downward when viewed from the X direction.

Exemplary Embodiment 4

An oral device according to Embodiment 4 of the present invention will be described. Note that in Embodiment 4, differences from Embodiment 1 will be mainly described. In Embodiment 4, configurations identical or equivalent to those in Embodiment 1 are denoted by the same reference numerals and are described. Further, in Embodiment 4, the description overlapping with Embodiment 1 will be omitted.

Figure 24A:
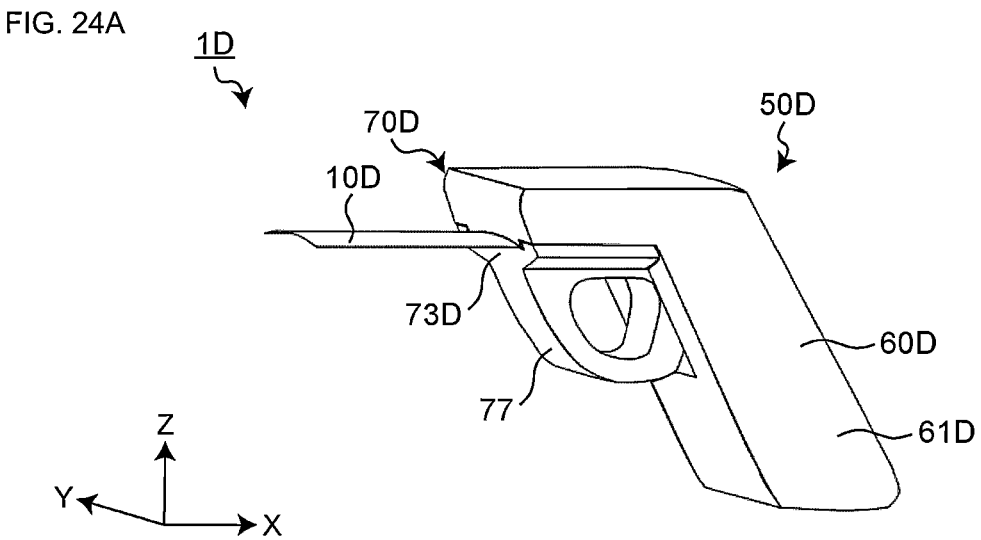
FIG. 24A is a schematic perspective view of an exemplary aspect of an oral device of Embodiment 4.
Figure 24B:
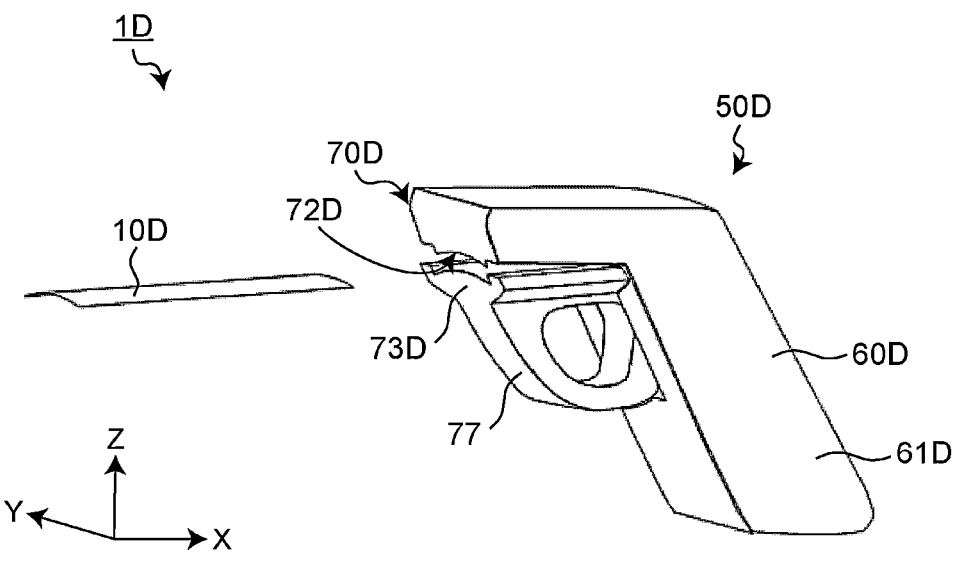
FIG. 24B is a schematic perspective view of an exemplary aspect of the oral device of Embodiment 4.

An exemplary aspect of the oral device of Embodiment 4 will be described with reference to FIG. 24A and FIG. 24B. FIG. 24A and FIG. 24B are schematic perspective views of an exemplary aspect of an oral device 1D of Embodiment 4. Note that in FIG. 24A and FIG. 24B, the display of the display unit 90 is omitted.

Embodiment 4 is different from Embodiment 1 in that the positions of an arrangement surface 72D and a pressing member 73D are reversed in an attachment/detachment operation unit 70D. Further, in Embodiment 4, as in Embodiment 3, the attachment/detachment operation unit 70D is configured to deform and fix an oral appliance 10D.

As illustrated in FIG. 24A and FIG. 24B, in the attachment/detachment operation unit 70D, the pressing member 73D is arranged below the arrangement surface 72D. When the oral appliance 10D is attached, the oral appliance 10D arranged on the arrangement surface 72D is pressed against and fixed by pushing up the pressing member 73D. When the oral appliance 10D is detached, the pressure on the oral appliance 10D is released and fixation is released by pushing down the pressing member 73D.

An oral body device 50D has a so-called gun-type configuration. To be specific, in the attachment/detachment operation unit 70D, the pressing member 73D has a ring-shaped member 77. The ring-shaped member 77 is formed integrally with the pressing member 73D. The motion of the pressing member 73D can be controlled by operating the ring-shaped member 77. For example, the user puts his/her index finger into the ring-shaped member 77 while gripping a grip portion 61D of a body portion 60D. The user can attach and detach the oral appliance 10D by operating the ring-shaped member 77 with the index finger. Further, the function of the guard 80 in Embodiment 1 can be realized by the ring-shaped member 77. For example, when the oral appliance 10D hangs down, the ring-shaped member 77 can protect the user's fingers.

Figure 25:
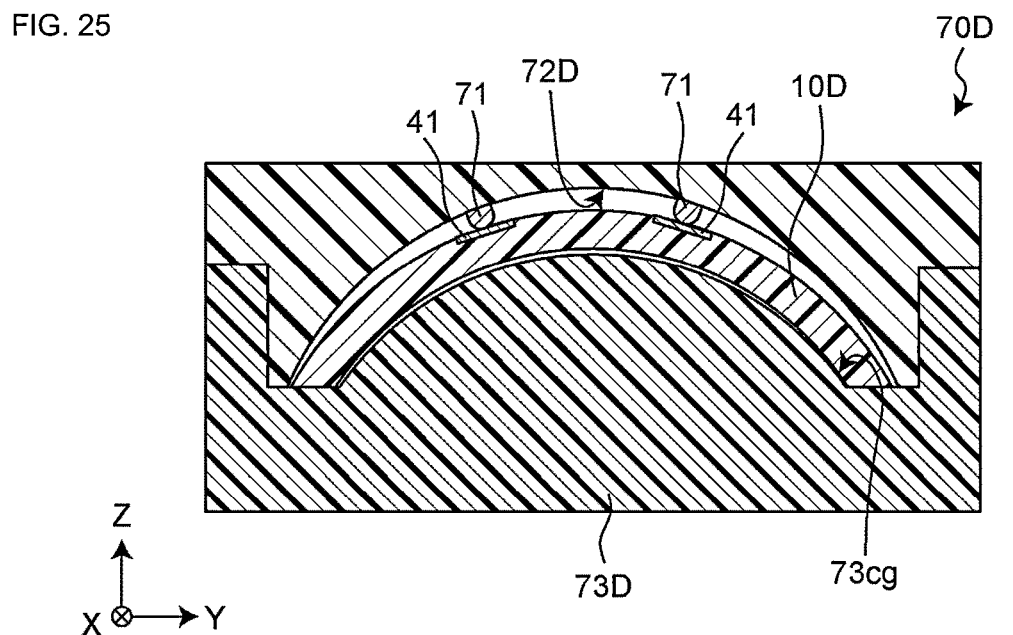
FIG. 25 is a schematic partially enlarged cross-sectional view illustrating an exemplary aspect of an attachment/detachment operation unit in an enlarged manner.

FIG. 25 is a schematic partially enlarged cross-sectional view illustrating an exemplary aspect of the attachment/detachment operation unit 70D in an enlarged manner. FIG. 25 illustrates a state in which the oral appliance 10D is attached to the attachment/detachment operation unit 70D. Note that FIG. 25 is a cross-sectional view when the attachment/detachment operation unit 70D is cut along the YZ plane.

As illustrated in FIG. 25, the attachment/detachment operation unit 70D has the arrangement surface 72D recessed in a semi-circular shape and the pressing member 73D having a semi-circular shape along the shape of the arrangement surface 72D. The plurality of connection terminals 71 is arranged on the arrangement surface 72D. The pressing member 73D has a semi-circular surface 73cg formed in a semi-circular shape.

The oral appliance 10D is fixed in a semi-circular deformed state by being sandwiched between the arrangement surface 72D and the semi-circular surface 73cg of the pressing member 73D. In Embodiment 4, the oral appliance 10D is deformed into a semi-circular shape protruding upward in the Z direction. In addition, the plurality of electrodes 41 of the oral appliance 10D comes into physical contact with the plurality of connection terminals 71 arranged on the arrangement surface 72D. Thus, the plurality of electrodes 41 and the plurality of connection terminals 71 are electrically connected to each other.

[Effects]

According to the oral body device 50D according to Embodiment 4, the following effects can be achieved.

In the attachment/detachment operation unit 70D of the oral body device 50D, the pressing member 73D is arranged below the arrangement surface 72D. The pressing member 73D has the ring-shaped member 77. With such a configuration, the user can easily attach and detach the oral appliance 10D by operating the ring-shaped member 77 of the pressing member 73D.

The attachment/detachment operation unit 70D includes the arrangement surface 72D recessed in a semi-circular shape and the pressing member 73D having a semi-circular shape along the shape of the arrangement surface 72D. With this configuration, the oral appliance 10D is fixed in a state of being deformed into a semi-circular shape protruding upward in the Z direction. As a result, the oral appliance 10D is prevented from hanging down and is easily fitted to the tongue or the like in the oral cavity.

Note that in Embodiment 4, an exemplary aspect in which the arrangement surface 72D and the pressing member 73D are formed in a semi-circular shape has been described, but the exemplary aspects are not limited thereto. For example, the arrangement surface 72D and the pressing member 73D only need to be curved in a concave shape or a convex shape.

In Embodiment 4, an exemplary aspect in which the plurality of connection terminals 71 is arranged on the arrangement surface 72 has been described, but the exemplary aspects are not limited thereto. For example, the plurality of connection terminals 71 can be arranged on the pressing member 73D.

(Modification 10)

Figure 26:
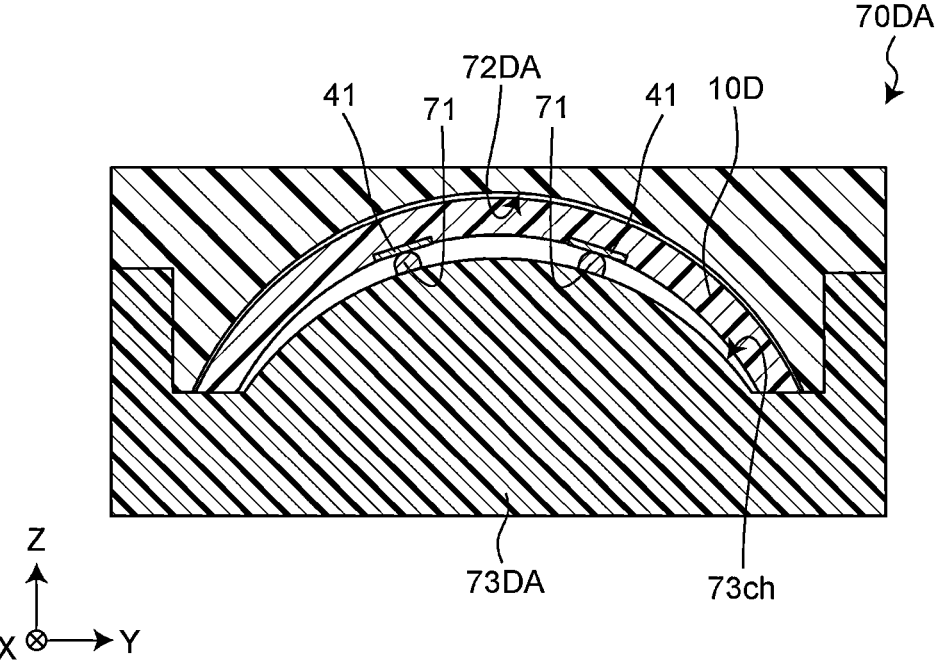
FIG. 26 is a schematic partially enlarged cross-sectional view illustrating an attachment/detachment operation unit of Modification 10 in an enlarged manner according to an exemplary aspect.

FIG. 26 is a schematic partially enlarged cross-sectional view illustrating an attachment/detachment operation unit 70DA of Modification 10 in an enlarged manner. FIG. 26 illustrates a state in which the oral appliance 10D is attached to the attachment/detachment operation unit 70DA. Note that FIG. 26 is a cross-sectional view of the attachment/detachment operation unit 70DA taken along the YZ plane.

As illustrated in FIG. 26, the attachment/detachment operation unit 70DA includes an arrangement surface 72DA recessed in a semi-circular shape and a pressing member 73DA having a semi-circular shape along the shape of the arrangement surface 72DA. The pressing member 73DA has a semi-circular surface 73ch formed in a semi-circular shape. The plurality of connection terminals 71 is arranged on the semi-circular surface 73ch. Also in such a configuration, the plurality of electrodes 41 of the oral appliance 10D can be electrically connected to the plurality of connection terminals 71.

(Modification 11)

Figure 27:
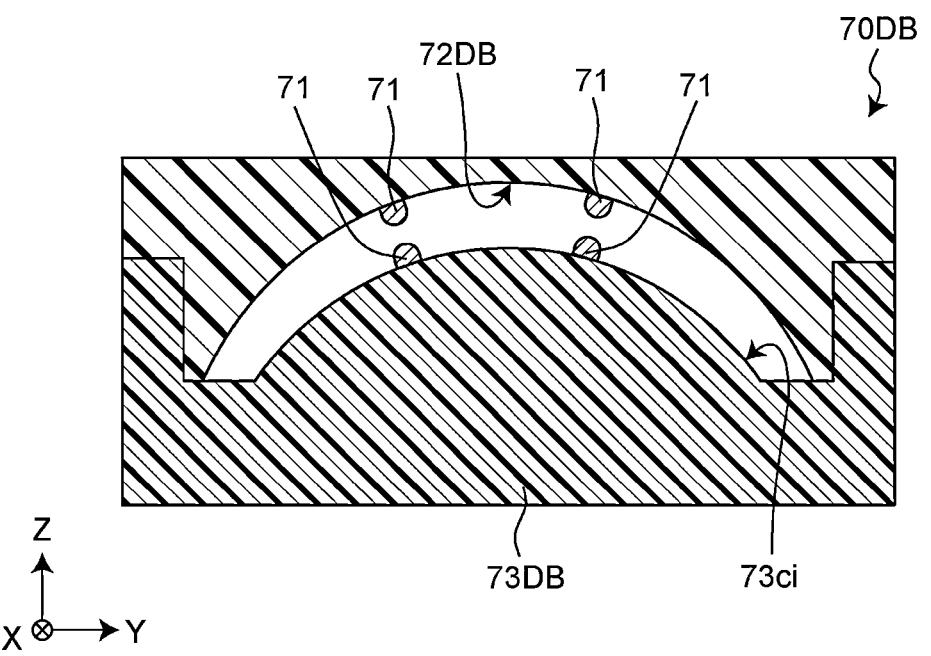
FIG. 27 is a schematic partially enlarged cross-sectional view illustrating an attachment/detachment operation unit of Modification 11 in an enlarged manner according to an exemplary aspect.

FIG. 27 is a schematic partially enlarged cross-sectional view illustrating an attachment/detachment operation unit 70DB of Modification 11 in an enlarged manner. FIG. 27 illustrates a state in which the oral appliance 10D is detached from the attachment/detachment operation unit 70DB. Note that FIG. 27 is a cross-sectional view of the attachment/detachment operation unit 70DB taken along the YZ plane.

As illustrated in FIG. 27, the attachment/detachment operation unit 70DB has an arrangement surface 72DB recessed in a semi-circular shape, and a pressing member 73DB having a semi-circular shape along the shape of the arrangement surface 72DB. The pressing member 73DB has a semi-circular surface 73ci formed in a semi-circular shape. The plurality of connection terminals 71 is arranged on both the arrangement surface 72DB and the semi-circular surface 73ci. Also in such a configuration, the plurality of electrodes 41 of the oral appliance 10D can be electrically connected to the plurality of connection terminals 71. In addition, in both a case where the plurality of electrodes 41 is arranged on the upper surface of the oral appliance 10D and a case where the plurality of electrodes 41 is arranged on the lower surface of the oral appliance 10D, the oral appliance 10D can be attached to the attachment/detachment operation unit 70DB while electrically connecting the plurality of electrodes 41 and the plurality of connection terminals 71.

Embodiment 5

An oral device according to Embodiment 5 of the present invention will be described. Note that in Embodiment 5, differences from Embodiment 1 will be mainly described. In Embodiment 5, configurations identical or equivalent to those in Embodiment 1 are denoted by the same reference numerals and are described. Further, in Embodiment 5, the description overlapping with Embodiment 1 will be omitted.

Figure 28:
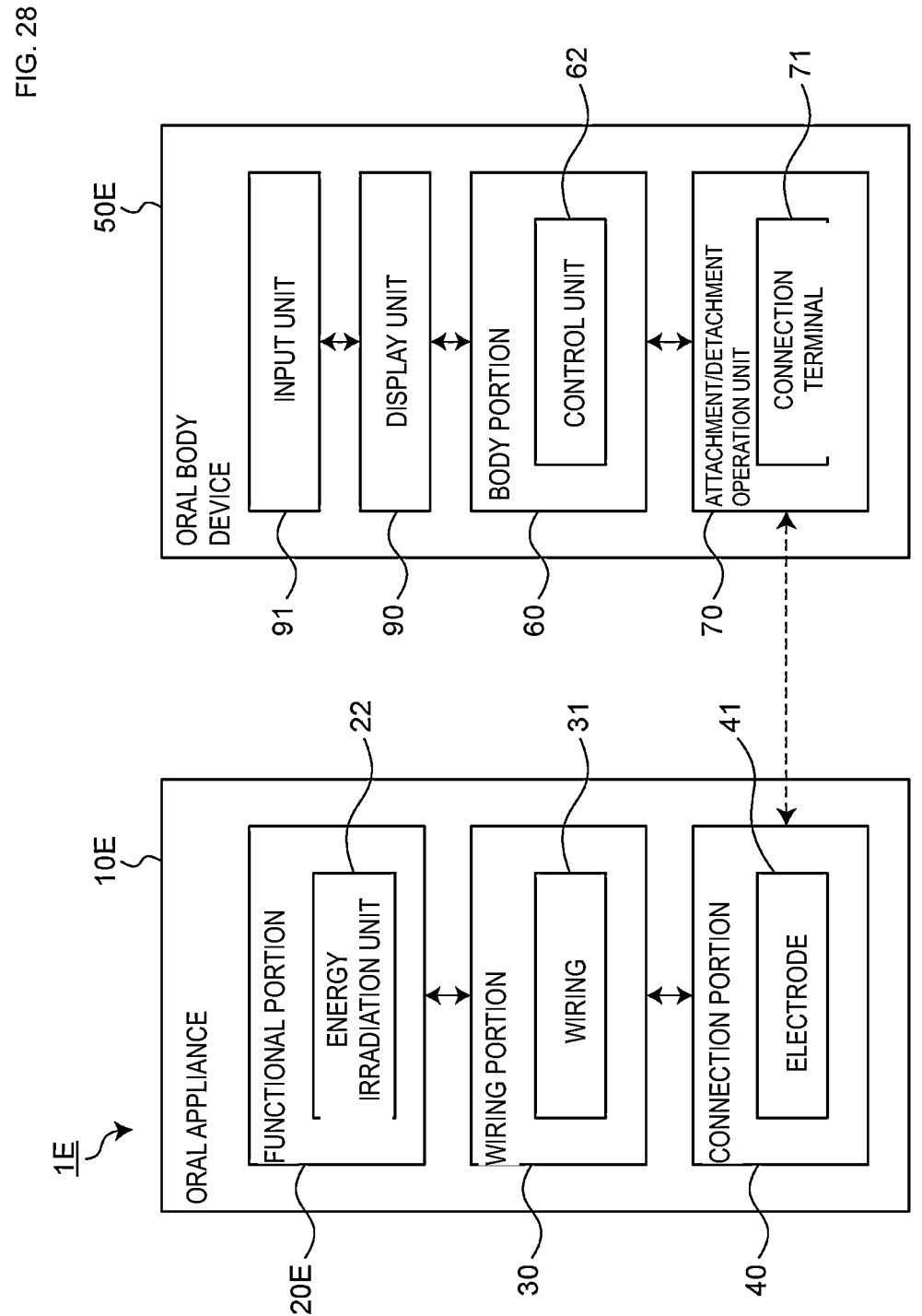
FIG. 28 is a block diagram illustrating a main configuration of an exemplary aspect of an oral device of Embodiment 5.

An exemplary aspect of the oral device of Embodiment 5 will be described with reference to FIG. 28. FIG. 28 is a block diagram illustrating a main configuration of an exemplary aspect of an oral device 1E of Embodiment 5.

Embodiment 5 is different from Embodiment 1 in that a functional portion 20E of an oral appliance 10E has an energy irradiation unit 22 and that an oral body device 50E controls the energy irradiation unit 22.

As illustrated in FIG. 28, in the oral appliance 10E, the functional portion 20E has the energy irradiation unit 22 that irradiates the oral cavity with energy. In Embodiment 5, an exemplary aspect in which the oral appliance 10E is a laser treatment device will be described. The oral appliance 10E is used by being detachably attached to the oral body device 50E.

Figure 29A:
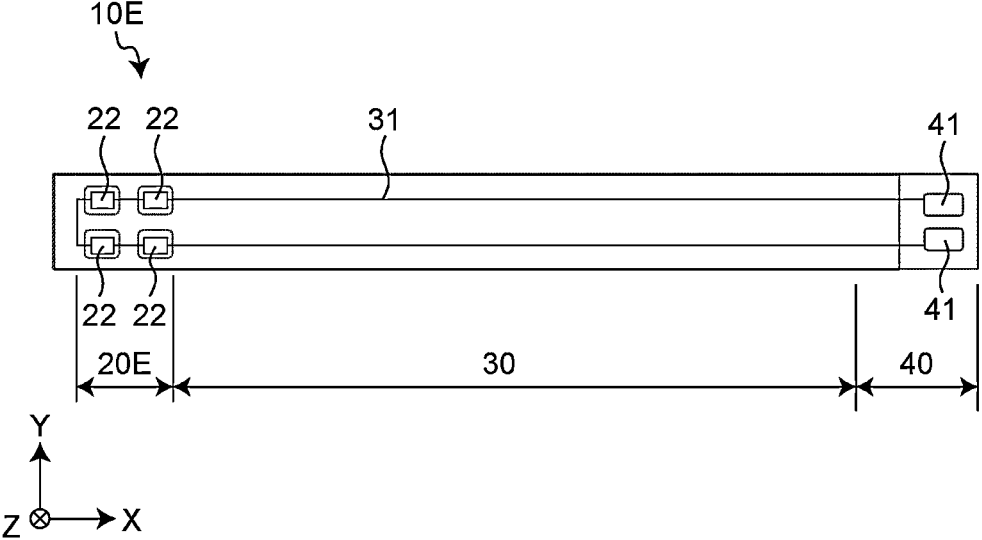
FIG. 29A is a schematic view illustrating an exemplary aspect of an oral appliance.
Figure 29B:
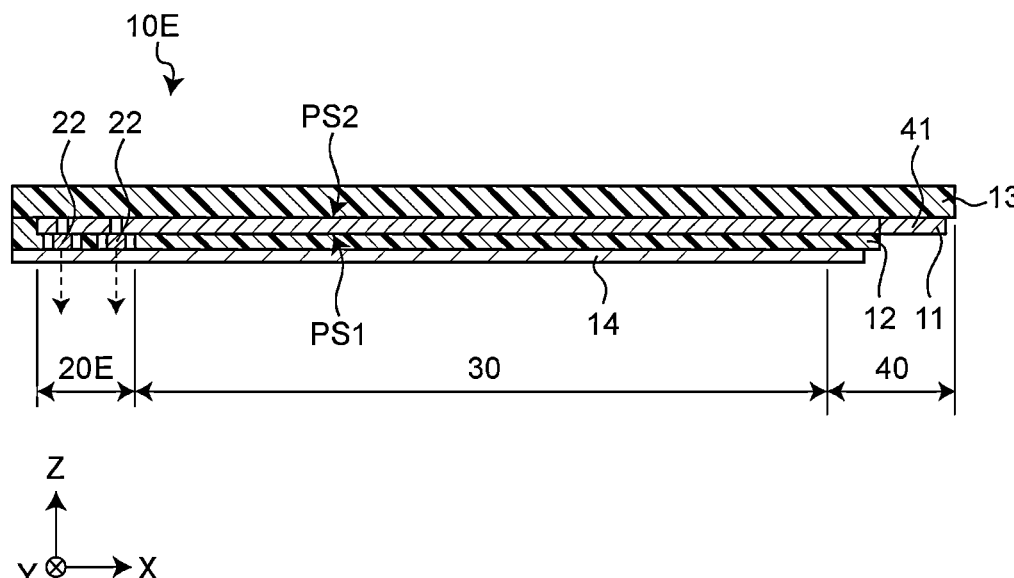
FIG. 29B is a schematic cross-sectional view of an exemplary aspect of the oral appliance of FIG. 29A.

FIG. 29A is a schematic view illustrating an exemplary aspect of the oral appliance 10E. FIG. 29B is a schematic cross-sectional view of an exemplary aspect of the oral appliance of FIG. 29A. As illustrated in FIG. 29A and FIG. 29B, the functional portion 20E has a plurality of the energy irradiation units 22. In Embodiment 5, the functional portion 20E includes four energy irradiation units 22.

The plurality of energy irradiation units 22 is, for example, a vertical cavity surface emitting laser (VCSEL). The plurality of energy irradiation units 22 is mounted on the first main surface PS1 of the wiring layer 11 and covered with a transparent resin film 14. The laser beams from the plurality of energy irradiation units 22 are transmitted through the resin film 14 and radiated to an irradiation site in the oral cavity.

Returning to FIG. 28, the oral body device 50E includes an input unit 91. The input unit 91 acquires input information for operating the energy irradiation unit 22. The user inputs input information to the input unit 91. For example, the input unit 91 can be one or a plurality of operation buttons, a touch panel, a microphone, or the like. The input information input to the input unit 91 is transmitted to the control unit 62. Exemplary aspects of the input information include laser irradiation, laser stop, a timer, an output value, and the like.

The control unit 62 receives input information from the input unit 91 and controls the motion of the oral appliance 10E based on the input information. The control unit 62 controls the plurality of energy irradiation units 22 based on the input information. For example, when input information of laser irradiation is input to the input unit 91, the control unit 62 controls the plurality of energy irradiation units 22 of the oral appliance 10E and causes the plurality of energy irradiation units 22 to radiate laser beams.

[Effects]

According to the oral body device 50E according to Embodiment 5, the following effects can be achieved.

The oral body device 50E is configured to detachably attach the oral appliance 10E having the energy irradiation unit 22, and can control the motion of the oral appliance 10E. Further, after the oral appliance 10E is used, the oral appliance 10E can be easily detached from the body device 50E.

Note that in Embodiment 5, an exemplary aspect in which the energy irradiation unit 22 is a vertical cavity surface emitting laser has been described, but the exemplary aspects are not limited thereto. It is sufficient that the energy irradiation unit 22 can radiate energy.

In Embodiment 5, an exemplary aspect in which the functional portion 20E includes four energy irradiation units 22 has been described, but the exemplary aspects are not limited thereto. The functional portion 20E only needs to have one or the plurality of energy irradiation units 22.

(Modification 12)

Figure 30:
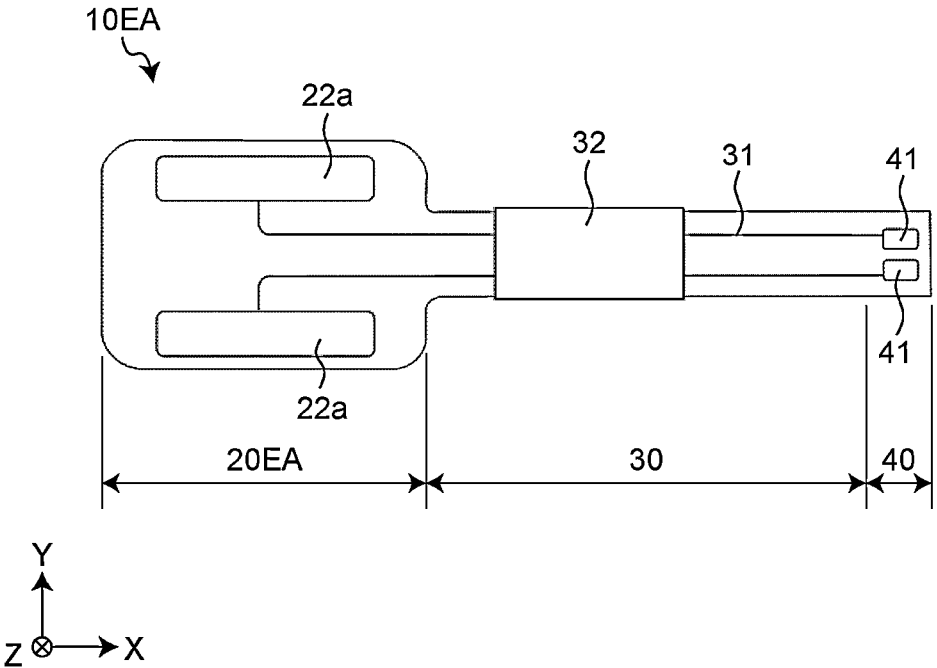
FIG. 30 is a schematic view illustrating an oral appliance of Modification 12 of an exemplary aspect.

FIG. 30 is a schematic view illustrating an oral appliance 10EA of Modification 12. As illustrated in FIG. 30, the oral appliance 10EA is used as a high-frequency therapeutic device. A plurality of energy irradiation units 22a of a functional portion 20EA is a plurality of electrodes through which a high frequency current can flow. A high frequency current is supplied between a plurality of electrodes in a state in which the plurality of electrodes is brought into contact with the inside of the oral cavity. The supply of the high frequency current is controlled by the body device 50E.

Note that in Modification 12, an exemplary aspect in which the oral appliance 10EA is a high frequency therapeutic device has been described, but the exemplary aspects are not limited thereto. The oral appliance 10EA can be a low frequency therapeutic device. In this case, a low frequency current is supplied between the plurality of electrodes.

(Modification 13)

Figure 31A:
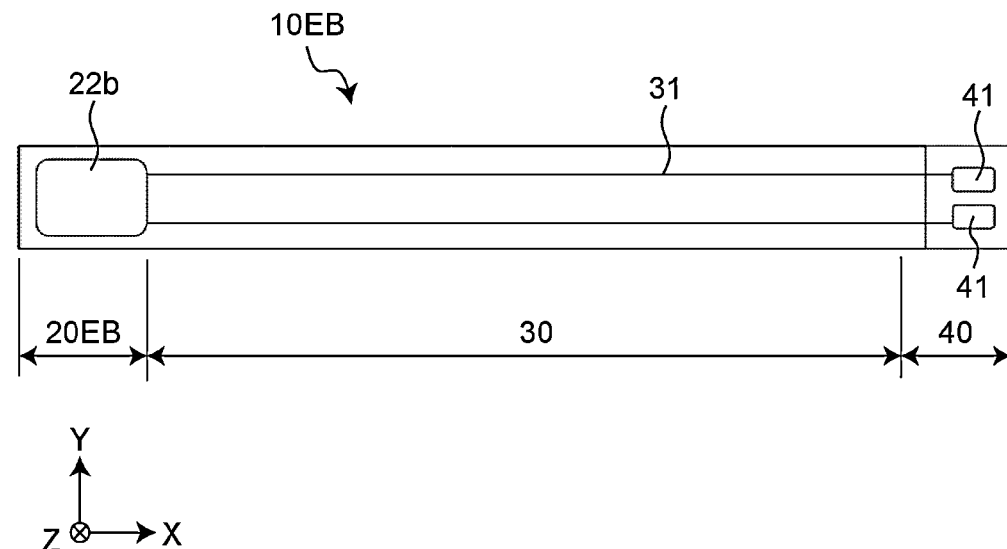
FIG. 31A is a schematic view illustrating an oral appliance of Modification 13 of an exemplary aspect.
Figure 31B:
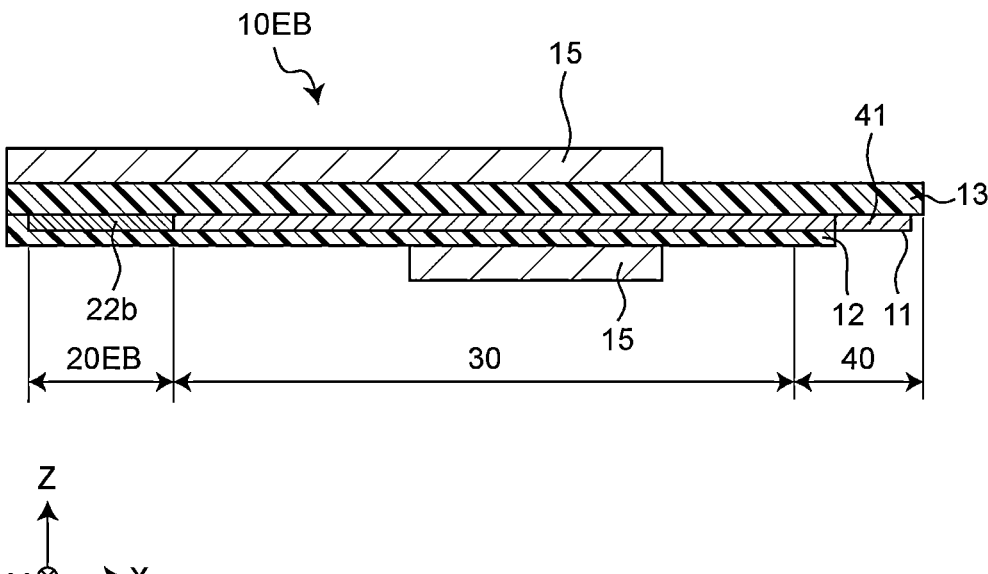
FIG. 31B is a schematic cross-sectional view of the oral appliance of Modification 13 of FIG. 31A.

FIG. 31A is a schematic view illustrating an oral appliance 10EB of Modification 13. FIG. 31B is a schematic cross-sectional view of the oral appliance 10EB of Modification 13 of FIG. 31A. As illustrated in FIG. 31A and FIG. 31B, the oral appliance 10EB is used as a hyperthermia device. An energy irradiation unit 22b of a functional portion 20EB is a seat heater. A seat heater performs heating by using heat generated by a resistor. Further, the oral appliance 10EB can be covered with a heat insulating material 15 except for a portion heated by the energy irradiation unit 22b.

Exemplary Embodiment 6

An oral device according to Embodiment 6 of the present invention will be described. Note that in Embodiment 6, differences from Embodiment 1 will be mainly described. In Embodiment 6, configurations identical or equivalent to those in Embodiment 1 are denoted by the same reference numerals and are described. Further, in Embodiment 6, the description overlapping with Embodiment 1 will be omitted.

Figure 32:
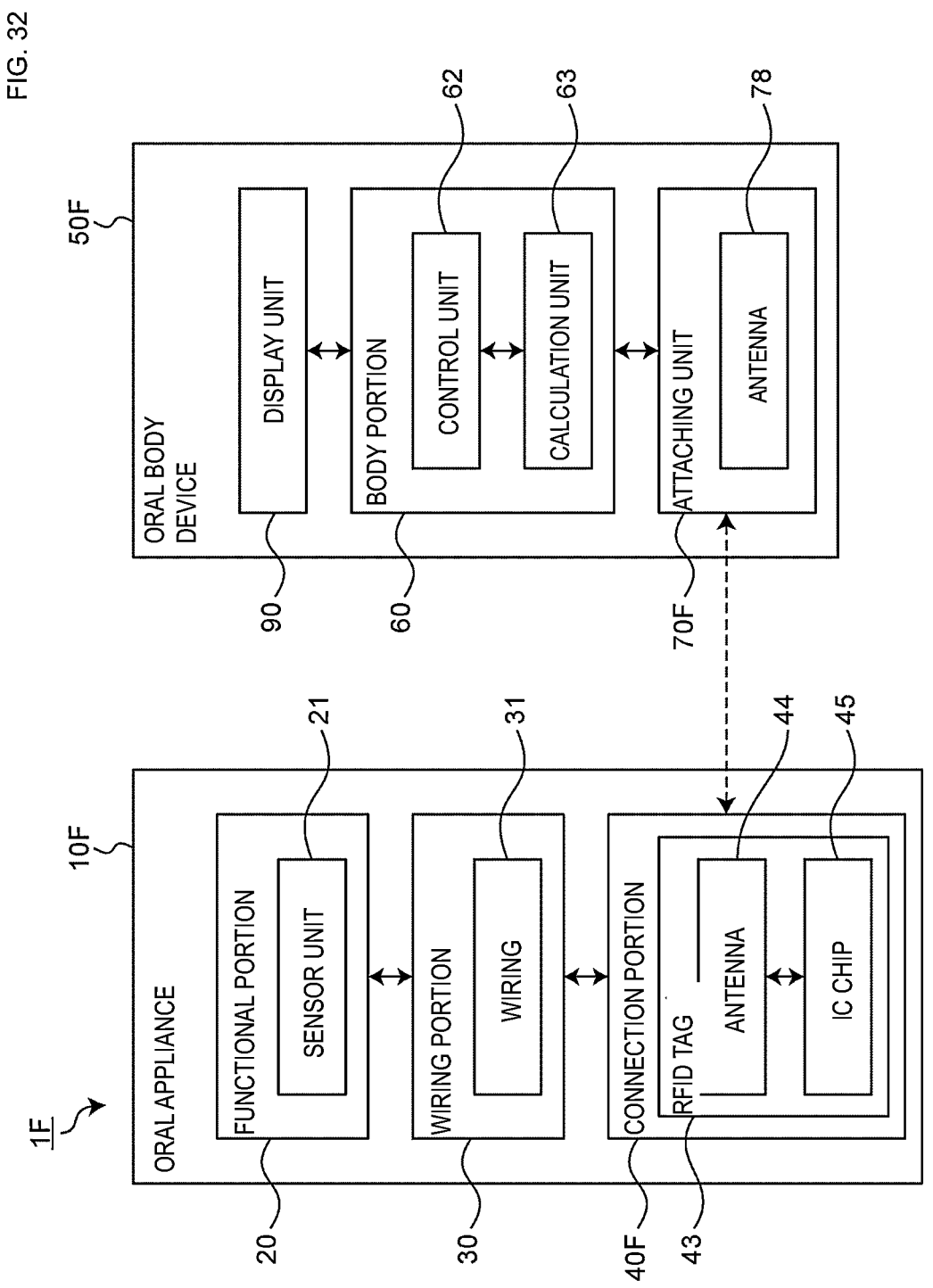
FIG. 32 is a block diagram illustrating a main configuration of an exemplary aspect of an oral device of Embodiment 6.

An exemplary aspect of the oral device of Embodiment 6 will be described with reference to FIG. 32. FIG. 32 is a block diagram illustrating a main configuration of an exemplary aspect of an oral device 1F of Embodiment 6.

Embodiment 6 is different from Embodiment 1 in that an electrical connection portion of an oral appliance 10F is a Radio Frequency Identification (RFID) tag 43, and an electrical connection conductor of an oral body device 50F is an antenna 78.

As illustrated in FIG. 32, in the oral appliance 10F, a connection portion 40F has the RFID tag 43 as an electrical connection portion. The RFID tag 43 is electrically connected to the electrical connection conductor of the oral body device 50F by wireless connection. That is, the RFID tag 43 is electrically connected to the antenna 78 of the oral body device 50F in a non-contact manner.

Figure 33:
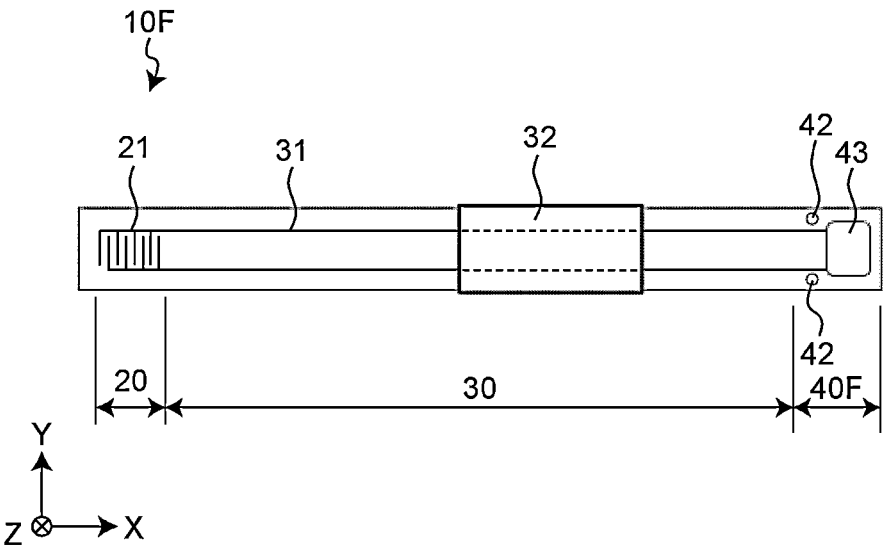
FIG. 33 is a schematic view illustrating an exemplary aspect of an oral appliance.
Figure 34:
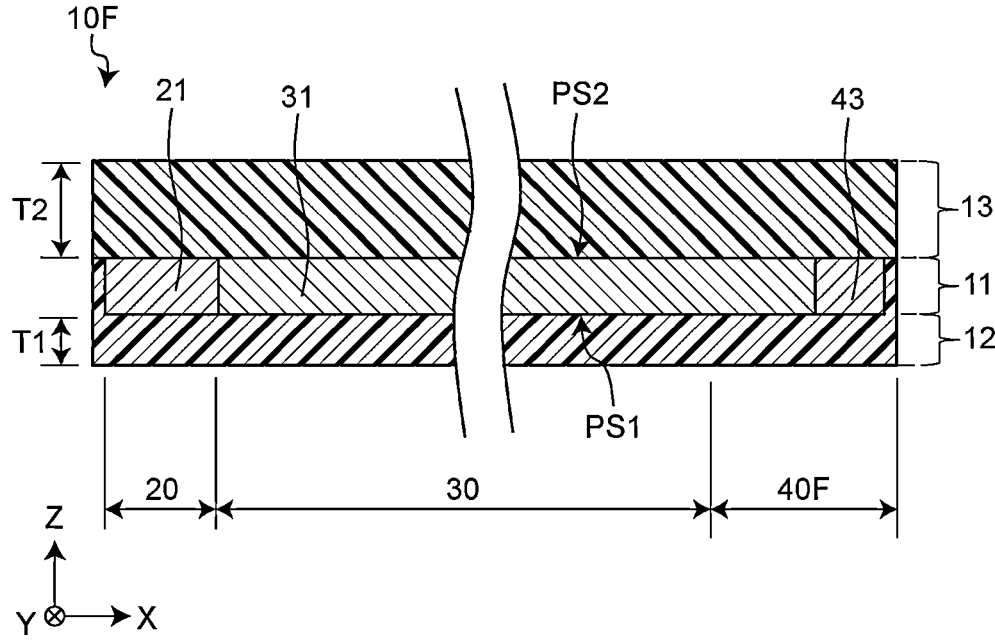
FIG. 34 is a schematic cross-sectional view of an exemplary aspect of the oral appliance of FIG. 33.

FIG. 33 is a schematic view illustrating an exemplary aspect of the oral appliance 10F. FIG. 34 is a schematic cross-sectional view of an exemplary aspect of the oral appliance 10F of FIG. 33. As illustrated in FIG. 33 and FIG. 34, the RFID tag 43 is arranged in a connection portion 40F in the wiring layer 11. The RFID tag 43 is covered with the plurality of insulating layers 12 and 13. That is, the RFID tag 43 is not exposed from the plurality of insulating layers 12 and 13.

Figure 35:
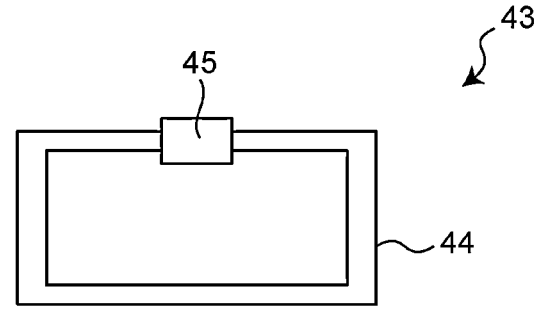
FIG. 35 is a schematic view of an exemplary aspect of an RFID tag.

FIG. 35 is a schematic view of an exemplary aspect of the RFID tag 43. As illustrated in FIG. 35, the RFID tag 43 includes an antenna 44 and an IC chip 45 connected to the antenna 44.

The antenna 44 is formed by winding a conductive linear member into a coil shape. The antenna 44 is formed of, for example, a wiring conductor pattern.

The IC chip 45 is, for example, a packaged RFIC chip (bare chip) having input/output terminals. For example, the IC chip 45 is an IC chip on which an RF circuit for an RFID tag, a memory circuit, a control circuit, and the like are mounted. The IC chip 45 is connected to the sensor unit 21 of the functional portion 20 via the wiring 31.

Figure 36:
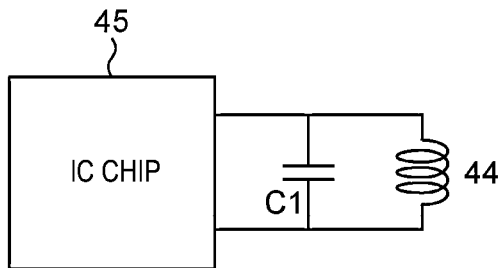
FIG. 36 is a schematic circuit diagram of an exemplary aspect of the RFID tag.

FIG. 36 is a schematic circuit diagram of an exemplary aspect of the RFID tag 43. As illustrated in FIG. 36, the antenna 44 is connected to the IC chip 45. A chip capacitor C1 is connected in parallel to the antenna 44. The chip capacitor C1 is, for example, a multilayer ceramic chip component. The antenna 44, the chip capacitor C1, and the capacitance component of the IC chip 45 form an antenna resonant circuit having a resonant frequency. Note that this circuit is an exemplary aspect, and the resonant circuit of the RFID tag 43 is not limited thereto.

Figure 37:
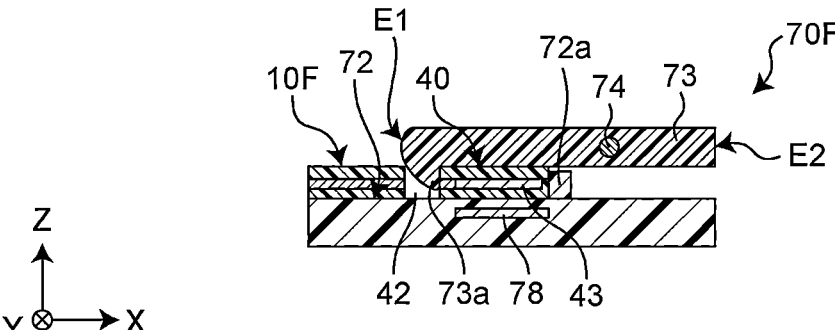
FIG. 37 is a schematic partially enlarged cross-sectional view illustrating an exemplary aspect of an attachment/detachment operation unit in an enlarged manner.

FIG. 37 is a schematic partially enlarged cross-sectional view illustrating an exemplary aspect of an attachment/detachment operation unit 70F in an enlarged manner. FIG. 37 illustrates a state in which the oral appliance 10F is attached to the attachment/detachment operation unit 70F, and the oral appliance 10F and the body device 50F are electrically connected in a non-contact manner.

As illustrated in FIG. 37, the attachment/detachment operation unit 70F includes the antenna 78. In this specification, the antenna 78 can be referred to as the body side antenna 78. Note that the attachment/detachment operation unit 70F has the same configuration as that of the attachment/detachment operation unit 70 of Embodiment 1 except that the attachment/detachment operation unit 70F includes the antenna 78 instead of the connection terminals 71.

The body side antenna 78 is formed by winding a conductive linear member in a coil shape. The body side antenna 78 is formed, for example, a wiring conductor pattern.

The body side antenna 78 is housed inside the body device 50F. The body side antenna 78 is arranged below the arrangement surface 72. To be specific, in a state in which the oral appliance 10F is arranged on the arrangement surface 72 and attached to the attachment/detachment operation unit 70F, the body side antenna 78 is positioned below the antenna 44 of the RFID tag 43. That is, in a state in which the oral appliance 10F is arranged on the arrangement surface 72 and attached to the attachment/detachment operation unit 70F, the body side antenna 78 faces the antenna 44 of the RFID tag 43.

When the antenna 44 of the oral appliance 10F and the body side antenna 78 of the body device 50F face each other, the RFID tag 43 and the body side antenna 78 are magnetic field coupled to each other. As a result, an induced current flows through the antenna 44, and the IC chip 45 operates. This enables the oral appliance 10F to be used.

[Effects]

According to the oral body device 50F according to Embodiment 6, the following effects can be achieved.

The electrical connection portion of the oral appliance 10F is the RFID tag 43. The electrical connection conductor of the oral body device 50F is the antenna 78. The attachment/detachment operation unit 70F electrically connects the RFID tag 43 and the antenna 78 by wireless connection. With such a configuration, attachment and detachment of the oral appliance 10F can be facilitated, and electrical connection between the oral appliance 10F and the oral body device 50F can be easily performed.

Exemplary Embodiment 7

An oral device according to Embodiment 7 of the present invention will be described. Note that in Embodiment 7, differences from Embodiment 1 will be mainly described. In Embodiment 7, configurations identical or equivalent to those in Embodiment 1 are denoted by the same reference numerals and are described. Further, in Embodiment 7, the description overlapping with Embodiment 1 will be omitted.

Figure 38A:
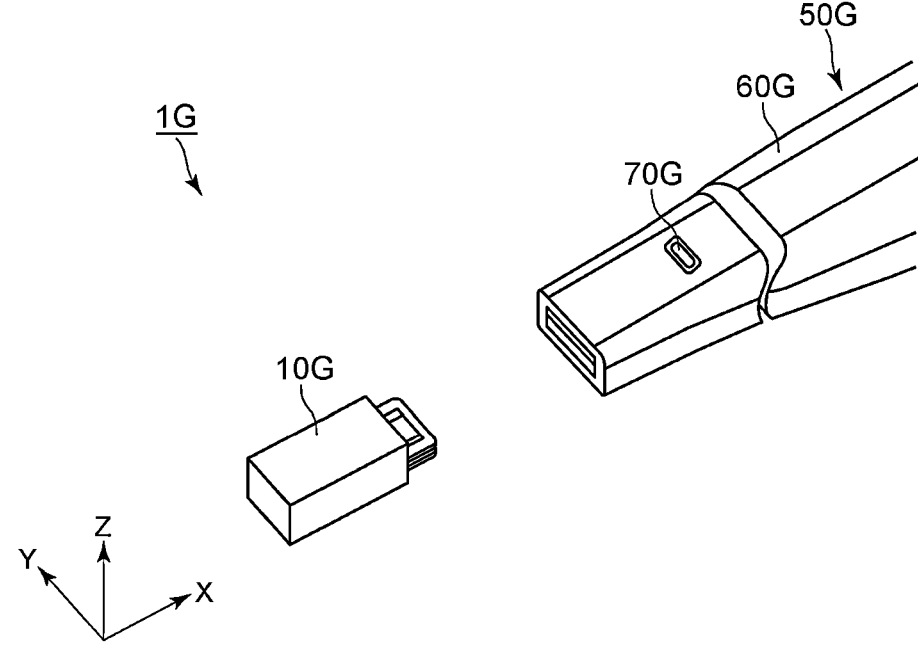
FIG. 38A is a schematic perspective view of an exemplary aspect of an oral device of Embodiment 7.
Figure 38B:
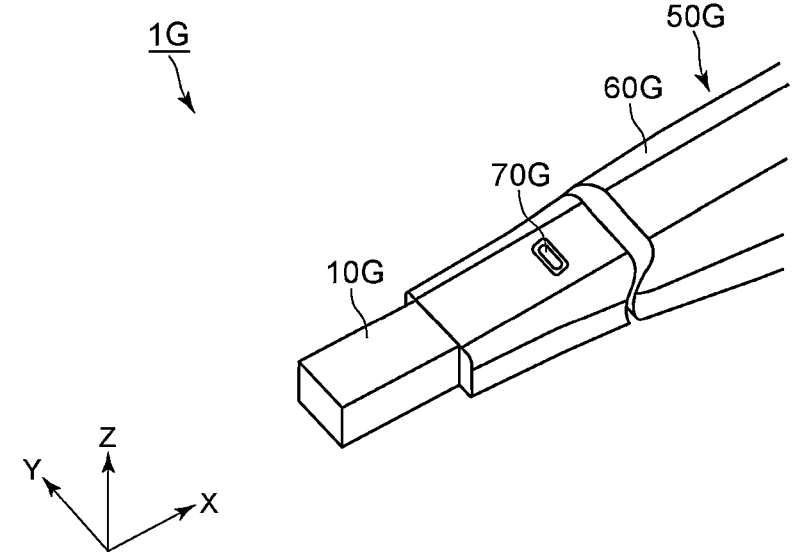
FIG. 38B is a schematic perspective view of an exemplary aspect of the oral device of Embodiment 7.

An exemplary aspect of the oral device of Embodiment 7 will be described with reference to FIG. 38A and FIG. 38B. FIG. 38A and FIG. 38B are schematic perspective views of an exemplary aspect of an oral device 1G of Embodiment 7. FIG. 38A illustrates a state in which an oral appliance 10G is detached from an oral body device 50G. FIG. 38B illustrates a state in which the oral appliance 10G is attached to the oral body device 50G.

In Embodiment 7, an exemplary aspect in which the oral device 1G is an occlusal force meter will be described. The occlusal force meter is a device for measuring a force during occlusion, that is, an occlusal force. In the oral device 1G, the oral appliance 10G acquires information related to the occlusal force and transmits the information related to the occlusal force to the oral body device 50G. The oral body device 50G calculates the occlusal force based on the information related to the occlusal force acquired by the oral appliance 10G.

As illustrated in FIG. 38A and FIG. 38B, the oral appliance 10G is detachably attached to an attachment/detachment operation unit 70G of the oral body device 50G.

Figure 39A:
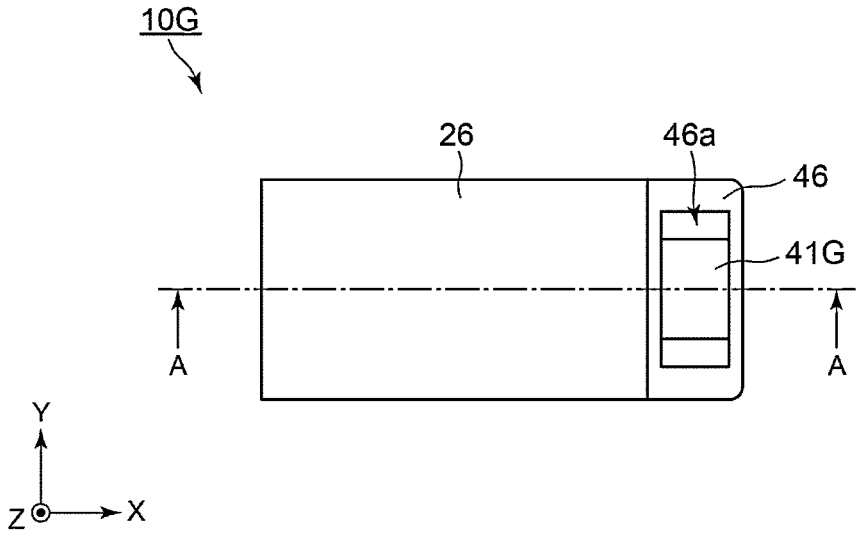
FIG. 39A is a schematic plan view of an exemplary aspect of an oral appliance of Embodiment 7.
Figure 39B:
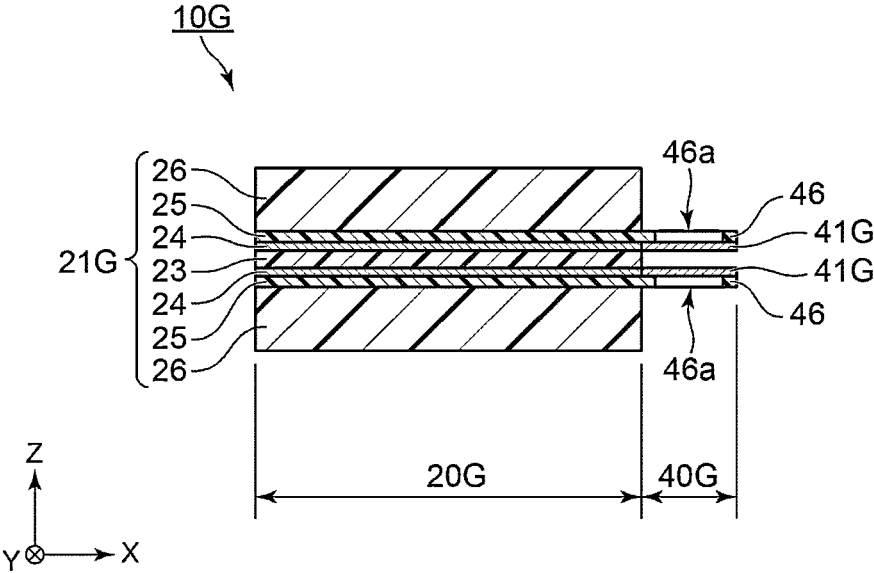
FIG. 39B is a schematic cross-sectional view of the oral appliance of FIG. 39A taken along line A-A.

The oral appliance 10G will be described with reference to FIG. 39A and FIG. 39B. FIG. 39A is a schematic plan view of an exemplary aspect of the oral appliance 10G of Embodiment 7. FIG. 39B is a schematic cross-sectional view of the oral appliance 10G of FIG. 39A taken along line A-A. As illustrated in FIG. 39A and FIG. 39B, the oral appliance 10G includes a functional portion 20G and a connection portion 40G.

The functional portion 20G includes a sensor unit 21G that detects information related to the occlusal force of the user. The sensor unit 21G is a portion bitten by the teeth of the user when the occlusal force is measured. The sensor unit 21G includes an insulating layer 23, an electrode 24, a weight distribution plate 25, and a pressure receiving portion 26.

In Embodiment 7, in the sensor unit 21G, two electrodes 24 are arranged on both surfaces of the insulating layer 23, and two weight distribution plates 25 and two pressure receiving portions 26 are arranged at outer side portions of the electrodes 24.

The insulating layer 23 is formed of a plate-shaped resin member. As the resin member, for example, a thermoplastic elastomer is used. For example, the insulating layer 23 has a length of 15 mm, a width of 30 mm, and a thickness of 0.8 mm. Note that the length means a dimension in the X direction, the width means a dimension in the Y direction, and the thickness means a dimension in the Z direction.

The electrode 24 is formed of a plate-shaped conductive member. As the conductive member, for example, a flexible printed circuit board is used. For example, the electrode 24 has a length of 15 mm, a width of 30 mm, and a thickness of 0.1 mm. Moreover, the electrodes 24 are arranged with the insulating layer 23 interposed therebetween. In addition, the electrode 24 is formed integrally with an electrical connection portion 41G of the connection portion 40G to be described later.

The weight distribution plate 25 is a plate-shaped member that distributes a weight applied to the sensor unit 21G. Specifically, the weight distribution plate 25 distributes the weight received by the pressure receiving portion 26. The weight distribution plate 25 is formed of a material harder than the insulating layer 23. For example, the weight distribution plate 25 is formed of a material, such as SUS. For example, the weight distribution plate 25 has a length of 30 mm, a width of 15 mm, and a thickness of 1 mm. The weight distribution plates 25 are arranged at the outer side portion of the electrodes 24, and sandwich the insulating layer 23 and the electrodes 24. Further, a part of the weight distribution plate 25 forms the connection portion 40G.

The pressure receiving portion 26 is a portion that comes into contact with the teeth of the user and receives pressure due to the occlusal force. The pressure receiving portion 26 is formed of a plate-shaped resin member. As the resin member, for example, rubber is used. For example, the pressure receiving portion 26 has a length of 30 mm, a width of 15 mm, and a thickness of 2 mm. The pressure receiving portions 26 are arranged at the outer side portion of the weight distribution plates 25, and sandwich the insulating layer 23, the electrodes 24, and the weight distribution plates 25.

The connection portion 40G is a portion detachably attached to the attachment/detachment operation unit 70G of the oral body device 50G, and is provided at the rear end on the side opposite to a front end of the oral appliance 10G. The connection portion 40G includes a plurality of engaging portions 46 and a plurality of the electrical connection portions 41G. The plurality of engaging portions 46 is formed by a pair of plate-shaped members arranged to face each other with a space therebetween. The plurality of electrical connection portions 41G is formed by a pair of electrodes arranged between the plurality of engaging portions 46. Further, the plurality of electrical connection portions 41G is respectively arranged inner side portion of the plurality of engaging portions 46.

In Embodiment 7, the engaging portion 46 is formed by a part of the weight distribution plate 25, and the electrical connection portion 41G is formed by a part of the electrode 24. Specifically, the engaging portion 46 is formed by causing one end of the weight distribution plate 25 to protrude from the insulating layer 23 and the pressure receiving portion 26. The electrical connection portion 41G is formed by causing one end of the electrode 24 to protrude from the insulating layer 23 and the pressure receiving portion 26.

The engaging portion 46 is provided with a lock hole 46a penetrating in a thickness direction. The lock hole 46a is formed in a rectangular shape when viewed in the thickness direction of the oral appliance 10G. In addition, when viewed in the thickness direction of the oral appliance 10G, the electrical connection portion 41G is arranged at a position overlapping with the lock hole 46a. The lock hole 46a is a hole into which a protrusion 73e of a pressing member 73G of the attachment/detachment operation unit 70G described later is inserted.

In the oral appliance 10G, the functional portion 20G is arranged in the oral cavity of the user, and the sensor unit 21G of the functional portion 20G is bitten from the upper and lower directions to acquire information related to the occlusal force. In addition, the information related to the occlusal force acquired by the sensor unit 21G is transmitted to the oral body device 50G via the connection portion 40G. In the oral body device 50G, the calculation unit 63 calculates the occlusal force based on the information related to the occlusal force acquired by the oral appliance 10G.

To be specific, in the oral appliance 10G, the user bites the sensor unit 21G from the upper and lower directions, whereby the pressure receiving portion 26 is pressurized. When pressure is applied to the pressure receiving portion 26, the weight distribution plate 25 evenly distributes the pressure. Accordingly, the insulating layer 23 is deformed in a state in which pressure is uniformly applied to the insulating layer 23. When the insulating layer 23 is deformed, the electrostatic capacity between the pair of electrodes 24 arranged on both main surfaces of the insulating layer 23 changes. The oral appliance 10G acquires information on electrostatic capacity as the information related to the occlusal force of the user.

In the connection portion 40G of the oral appliance 10G, the electrical connection portion 41G and an electrical connection conductor 71G of the oral body device 50G are electrically connected by physical contacting. Therefore, the information on the electrostatic capacity acquired by the oral appliance 10G is transmitted to the oral body device 50G via the electrical connection portion 41G and the electrical connection conductor 71G. In the oral body device 50G, the calculation unit 63 calculates the occlusal force based on the information on the electrostatic capacity acquired by the oral appliance 10G.

Figure 40A:
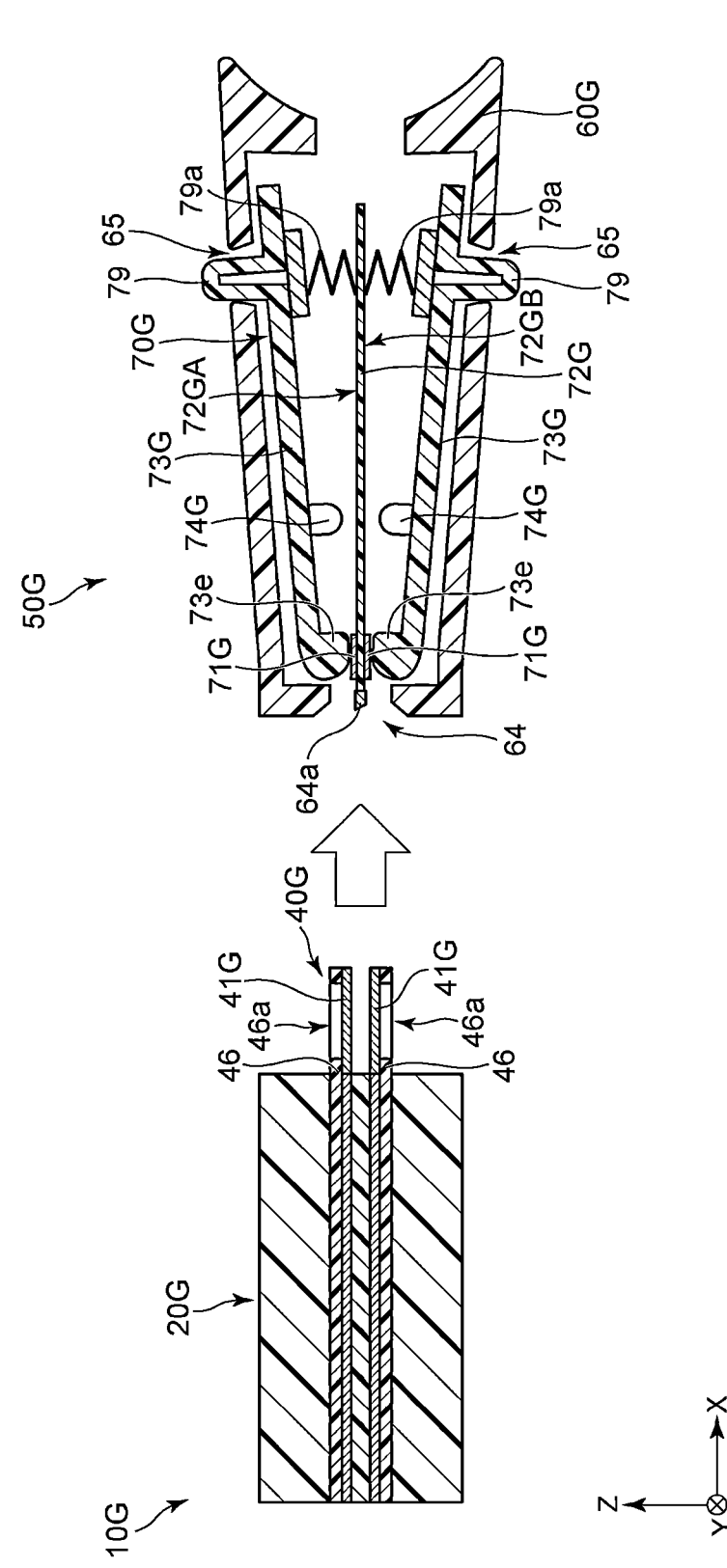
FIG. 40A is a schematic diagram illustrating an exemplary aspect of an operation of an attachment/detachment operation unit.
Figure 40B:
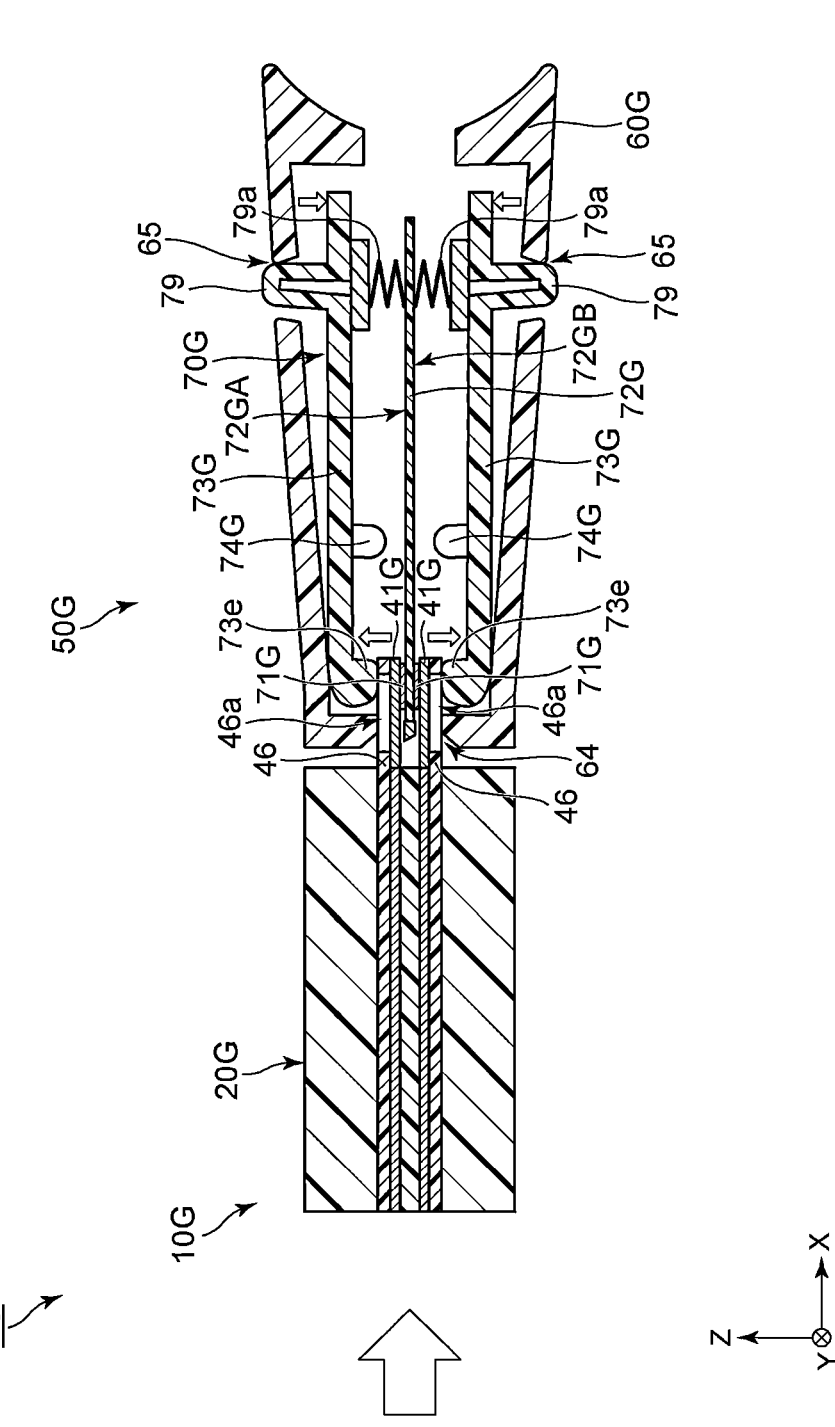
FIG. 40B is a schematic diagram illustrating an exemplary aspect of the operation of the attachment/detachment operation unit.
Figure 40C:
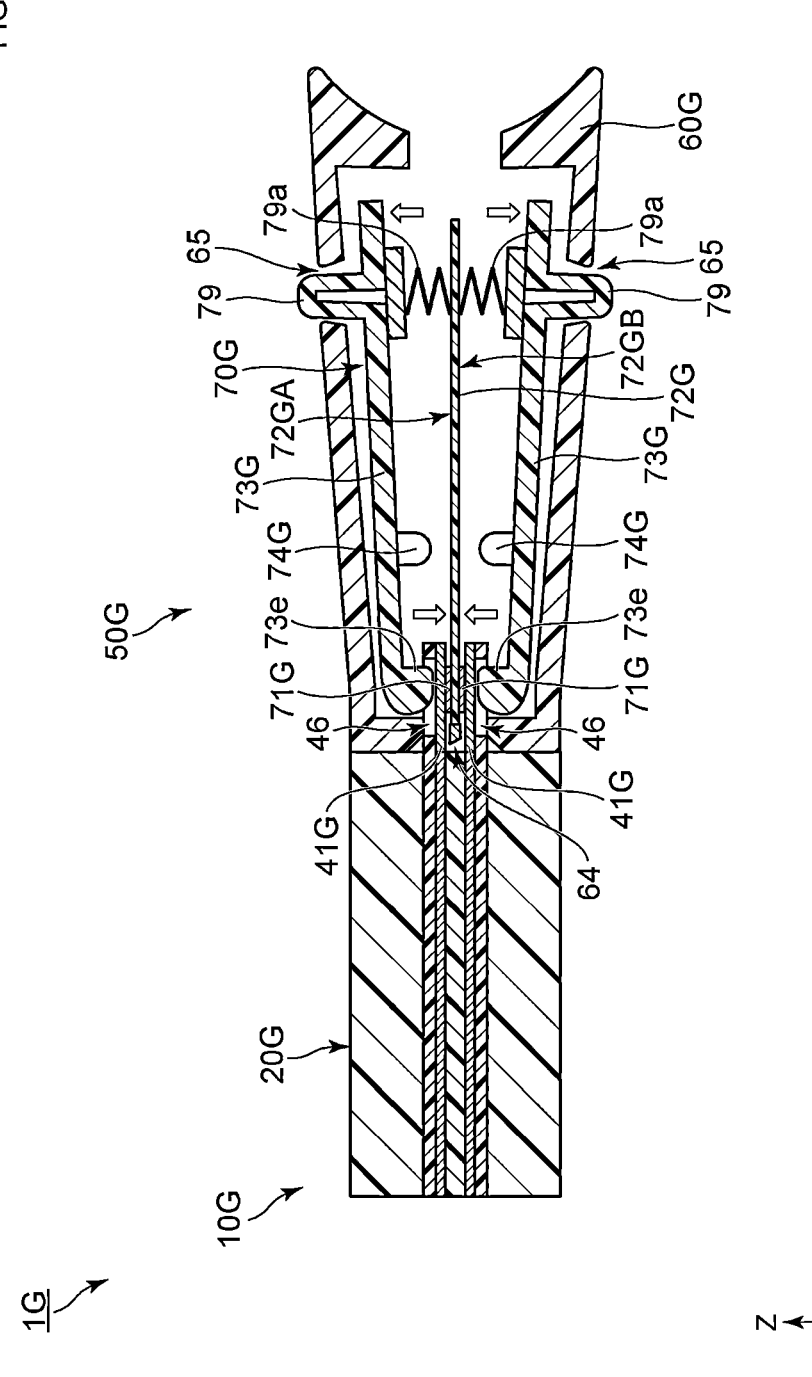
FIG. 40C is a schematic diagram illustrating an exemplary aspect of the operation of the attachment/detachment operation unit.

Next, an exemplary aspect of the configuration of the oral body device 50G and the operation of the attachment/detachment operation unit 70G will be described with reference to FIGS. 40A to 40C. FIGS. 40A to 40C are schematic diagrams illustrating an exemplary aspect of the operation of the attachment/detachment operation unit 70G.

As illustrated in FIGS. 40A to 40C, the oral body device 50G includes a substrate 72G provided with the electrical connection conductor 71G and the attachment/detachment operation unit 70G.

The substrate 72G is formed in a plate shape and is arranged inside a body portion 60G. One end of the substrate 72G is arranged on an opening 64 side provided at a front end of the body portion 60G. The opening 64 is a portion into which the connection portion 40G of the oral appliance 10G is inserted. Further, the opening 64 is provided with a guide 64a when the oral appliance 10G is inserted.

A plurality of the electrical connection conductors 71G is provided on both main surfaces of the substrate 72G. To be specific, the substrate 72G has a first arrangement surface 72GA and a second arrangement surface 72GB opposite to the first arrangement surface 72GA. One electrical connection conductor 71G is provided on the first arrangement surface 72GA of the substrate 72G, and one electrical connection conductor 71G is provided on the second arrangement surface 72GB of a substrate 72G. The plurality of electrical connection conductors 71G is provided on one end side of the substrate 72G.

The plurality of electrical connection conductors 71G is formed by a plurality of connection terminals. For example, a pad electrode can be used as the connection terminal. The pad electrode is formed of, for example, a conductive material. The pad electrode is formed, for example, in a rectangular shape when viewed from the main surface side of the substrate 72G. The pad electrode can be formed of, for example, a material similar to that of the electrode 24.

The attachment/detachment operation unit 70G includes a plurality of the pressing members 73G. The plurality of pressing members 73G is a member configured to apply and release a force to the oral appliance 10G. The plurality of pressing members 73G is respectively arranged on both main surfaces of the substrate 72G, and is configured to apply a force in a direction intersecting both the main surfaces of the substrate 72G. For purposes of this disclosure, it is noted that the phrase "applying a force in a direction intersecting both main surfaces of the substrate 72G" means applying a force in a direction approaching the substrate 72G. To be specific, the plurality of pressing members 73G includes at least two pressing members 73G. The plurality of pressing members 73G is arranged on both main surface sides of the substrate 72G, that is, on the first arrangement surface 72GA side and the second arrangement surface 72GB side inside the body portion 60G. The plurality of pressing members 73G is configured to apply a force in a direction intersecting both main surfaces of the substrate 72G at a portion where the plurality of electrical connection conductors 71G, that is, the plurality of connection terminals is provided. The pressing member 73G applies a force to the connection portion 40G of the oral appliance 10G in a state in which the electrical connection portion 41G (plurality of electrodes) and the plurality of electrical connection conductors 71G (plurality of connection terminals) are in contact with each other. Accordingly, the pressing member 73G can fix the oral appliance 10G to the oral body device 50G in a state in which the electrical connection portion 41G of the oral appliance 10G is electrically connected to the electrical connection conductor 71G.

The pressing member 73G is formed of a rod-shaped member having one end and the other end. The one end of the pressing member 73G is arranged on the opening 64 side, and the other end of the pressing member 73G is arranged inside the body portion 60G on the side opposite to the opening 64.

Each of the plurality of pressing members 73G has the protrusion 73e protruding toward both main surfaces of the substrate 72G. The protrusion 73e is provided at the one end of the pressing member 73G. The protrusion 73e has, for example, a round curved shape. In a state in which the connection portion 40G of the oral appliance 10G is attached to the oral body device 50G, the protrusion 73e is inserted into the lock hole 46a provided in the engaging portion 46 of the connection portion 40G. As such, the protrusion 73e is engaged with the engaging portion 46, and the oral appliance 10G is fixed to the oral body device 50G.

Further, each of the plurality of pressing members 73G has an operation portion 79 positioned in an operation hole 65 of the body portion 60G. The operation portion 79 is provided on the other end side of the pressing member 73G and protrudes from the operation hole 65. In Embodiment 7, the operation portion 79 is formed by bending the pressing member 73G into a U-shape. Note that the shape of the operation portion 79 is not limited thereto.

A plurality of elastic members 79a is arranged on the other end side of the plurality of pressing members 73G. The plurality of elastic members 79a is arranged on both main surfaces of the substrate 72G, and biases the other end side of the plurality of pressing members 73G in a direction away from both the main surfaces of the substrate 72G. To be specific, on the other end side of the substrate 72G, one elastic member 79a is arranged on the first arrangement surface 72GA, and one elastic member 79a is arranged on the second arrangement surface 72GB. This presses against the other end side of the pressing member 73G in a direction away from the substrate 72G and causes the operation portion 79 to protrude from the operation hole 65. The elastic member 79a is, for example, a spring.

Each of the plurality of pressing members 73G has a rotation shaft 74G and rotationally moves around the rotation shaft 74G. The rotation shaft 74G is provided between one end and the other end of the pressing member 73G. When the other end side of the pressing member 73G is biased by the elastic member 79a in a direction away from the substrate 72G, the pressing member 73G rotationally moves around the rotation shaft 74G. Accordingly, the one end side of the pressing member 73G approaches the substrate 72G, whereas the other end side of the pressing member 73G moves away from the substrate 72G. Further, when the operation portion 79 is pressed in a direction approaching the substrate 72G, the pressing member 73G rotationally moves around the rotation shaft 74G, and one end side of the pressing member 73G moves away from the substrate 72G while the other end side of the pressing member 73G approaches the substrate 72G.

Next, an exemplary aspect of an operation of the attachment/detachment operation unit 70G will be described.

As illustrated in FIG. 40A, the connection portion 40G of the oral appliance 10G is inserted into the opening 64 of the body portion 60G. The connection portion 40 of the oral appliance 10G is inserted into the opening 64 along the guide 64a. To be specific, the oral appliance 10G is inserted into the opening 64 such that the guide 64a is positioned between the pair of engaging portions 46.

As illustrated in FIG. 40B, when the connection portion 40G of the oral appliance 10G is inserted into the body portion 60G from the opening 64, one end of the pressing member 73G, that is, the protrusion 73e is pressed by the engaging portion 46 in a direction away from the substrate 72G. At this time, the electrical connection portion 41G of the oral appliance 10G moves along the first arrangement surface 72GA and the second arrangement surface 72GB of the substrate 72G and comes into physical contact with the electrical connection conductor 71G.

As illustrated in FIG. 40C, the protrusion 73e of the pressing member 73G is inserted into the lock hole 46a of the engaging portion 46 of the connection portion 40G, whereby the protrusion 73e and the engaging portion 46 are engaged with each other. In a state in which the protrusion 73e of the pressing member 73G is inserted in the lock hole 46a, the other end side of the pressing member 73G is biased in a direction away from the substrate 72G by the elastic member 79a. Therefore, a force is applied to the one end side of the pressing member 73G in a direction approaching the substrate 72G. Accordingly, it is possible to maintain a state in which the protrusion 73e of the pressing member 73G is inserted in the lock hole 46a, that is, a state in which the protrusion 73e is engaged with the engaging portion 46. As a result, the oral appliance 10G is fixed to the oral body device 50G in a state in which the electrical connection portion 41G and the electrical connection conductor 71G are electrically connected.

Note that when the oral appliance 10G is detached, the protrusion 73e of the pressing member 73G is moved in a direction away from the substrate 72G by pressing the operation portion 79 of the pressing member 73G in a direction approaching the substrate 72G. As a result, the protrusion 73e of the pressing member 73G moves to the outside of the lock hole 46a, and the engagement between the protrusion 73e and the engaging portion 46 is released, so that the oral appliance 10G can be detached from the oral body device 50G.

[Effects]

According to the oral body device 50G according to Embodiment 7, the following effects can be achieved.

The electrical connection portion 41G of the oral appliance 10G has a plurality of electrodes. The electrical connection conductor 71G of the oral body device 50G has a plurality of connection terminals provided on both main surfaces of the substrate 72G. The attachment/detachment operation unit 70G has the plurality of pressing members 73G that is respectively arranged on both main surfaces of the substrate 72G and applies a force in a direction intersecting both the main surfaces of the substrate 72G. The plurality of pressing members 73G fixes the oral appliance 10 by applying a force in a direction intersecting both main surfaces of the substrate 72G in a state in which the plurality of electrodes and the plurality of connection terminals are respectively in contact with each other. With such a configuration, attachment and detachment of the oral appliance 10G can be facilitated, and electrical connection between the oral appliance 10G and the oral body device 50G can be easily performed.

Each of the plurality of pressing members 73G has the protrusion 73e protruding toward both main surfaces of the substrate 72G. According to such a configuration, the plurality of pressing members 73G easily comes into contact with the oral appliance 10G, and the oral appliance 10G can be easily and firmly fixed to the oral body device 50G.

Note that in Embodiment 7, an exemplary aspect in which the lock hole 46a is provided in the engaging portion 46 of the oral appliance 10G has been described, but the exemplary aspects are not limited thereto. In the oral appliance 10, the lock hole 46a is not an essential component, and does not have to be provided in the engaging portion 46.

In Embodiment 7, an exemplary aspect in which the engaging portion 46 is formed by a part of the weight distribution plate 25 has been described, but the exemplary aspects are not limited thereto. For example, the engaging portion 46 can be formed of another member different from the weight distribution plate 25.

In Embodiment 7, an exemplary aspect in which the electrical connection portion 41G is an electrode formed integrally with the electrode 24 has been described, but the exemplary aspects are not limited thereto. For example, the electrical connection portion 41G can be formed of another member different from the electrode 24. In this case, a wiring portion can be provided between the electrode 24 and the electrical connection portion 41G.

In Embodiment 7, an exemplary aspect in which the oral appliance 10G includes the weight distribution plate 25 has been described, but the exemplary aspects are not limited thereto. In the oral appliance 10G, the weight distribution plate 25 is not an essential component.

In Embodiment 7, an exemplary aspect in which the plurality of pressing members 73G rotationally moves around the rotation shaft 74G has been described, but the exemplary aspects are not limited thereto. For example, the pressing member 73G can be the pressing members 73 and 73AA of Modifications 1 to 5 of Embodiment 1.

In Embodiment 7, an exemplary aspect in which the oral appliance 10G acquires information on electrostatic capacity as information related to the occlusal force of the user has been described, but the exemplary aspects are not limited thereto. The oral appliance 10G only needs to acquire information for calculating the occlusal force as the information related to the occlusal force of the user.

Exemplary Embodiment 8

An oral device according to Embodiment 8 of the present invention will be described. It is noted that in Embodiment 8, differences from Embodiment 1 will be mainly described. In Embodiment 8, configurations identical or equivalent to those in Embodiment 1 are denoted by the same reference numerals and are described. Further, in Embodiment 8, the description overlapping with Embodiment 1 will be omitted. Furthermore, in embodiment 8, there are descriptions partially overlapping with those in Embodiment 7, but such descriptions will be omitted.

40

Figure 41A:
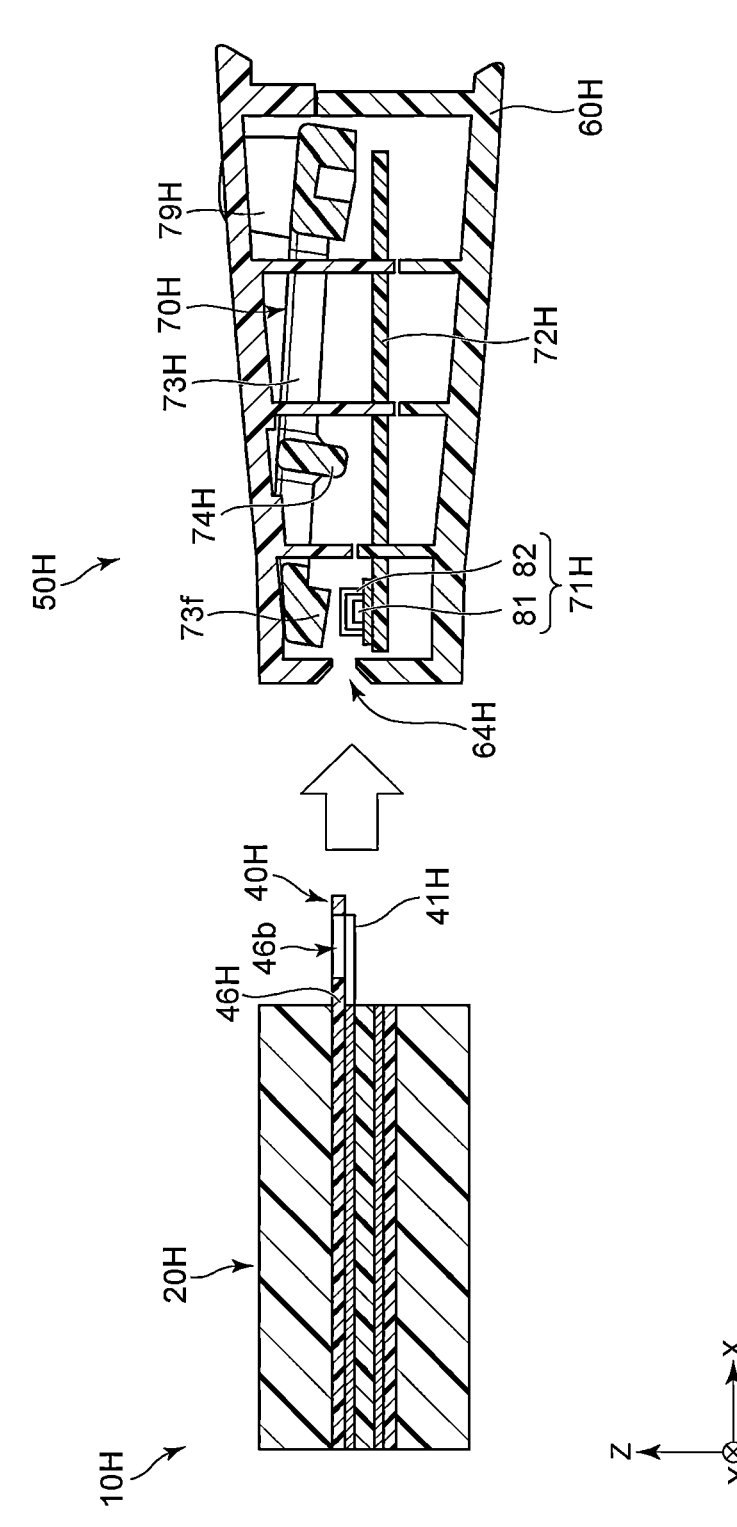
FIG. 41A is a schematic cross-sectional view of an exemplary aspect of an oral device of Embodiment 8.
Figure 41B:
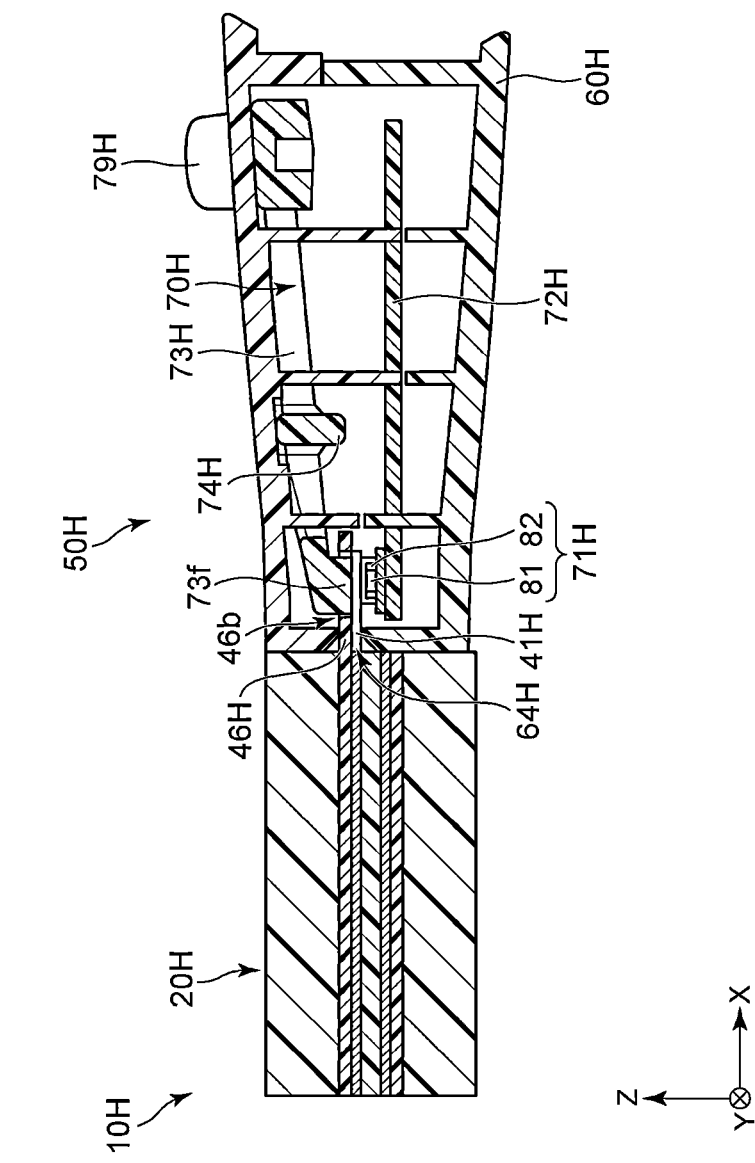
FIG. 41B is a schematic cross-sectional view of an exemplary aspect of the oral device of Embodiment 8.

An exemplary aspect of the oral device of Embodiment 8 will be described with reference to FIG. 41A and FIG. 41B. FIG. 41A and FIG. 41B are schematic cross-sectional views of an exemplary aspect of an oral device 1H of Embodiment 8. FIG. 41A illustrates a state in which an oral appliance 10H is detached from an oral body device 50H. FIG. 41B illustrates a state in which the oral appliance 10H is attached to the oral body device 50H.

In Embodiment 8, an exemplary aspect in which the oral device 1H is an occlusal force meter will be described. Since the occlusal force meter is similar to that in Embodiment 7, the description thereof will be omitted. Further, Embodiment 8 is different from Embodiment 7 in that a pressing member 73H is arranged only on one main surface of a substrate 72H.

As illustrated in FIG. 41A and FIG. 41B, the oral appliance 10H is detachably attached to an attachment/detachment operation unit 70H of the oral body device 50H.

Figure 42A:
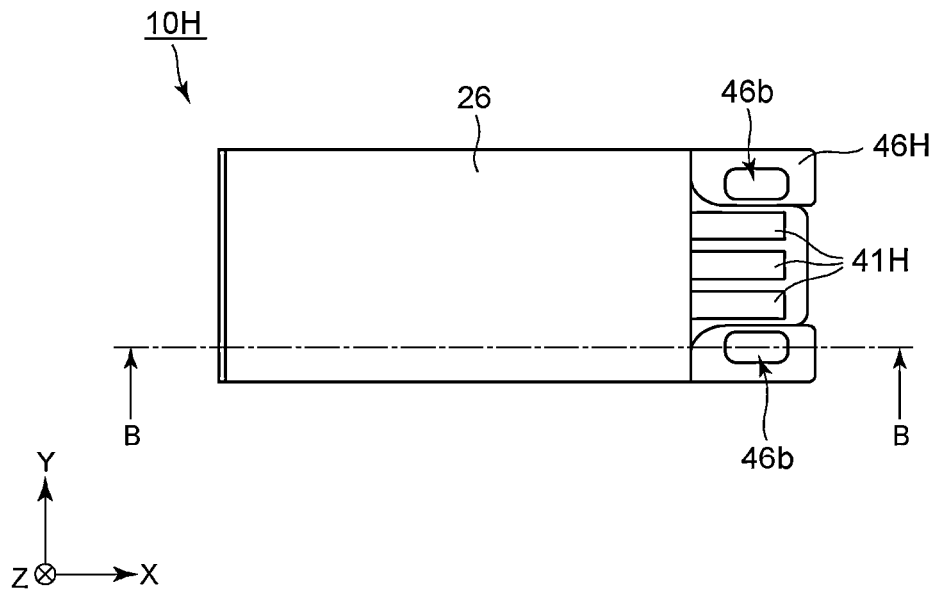
FIG. 42A is a schematic bottom view of an exemplary aspect of an oral appliance of Embodiment 8.
Figure 42B:
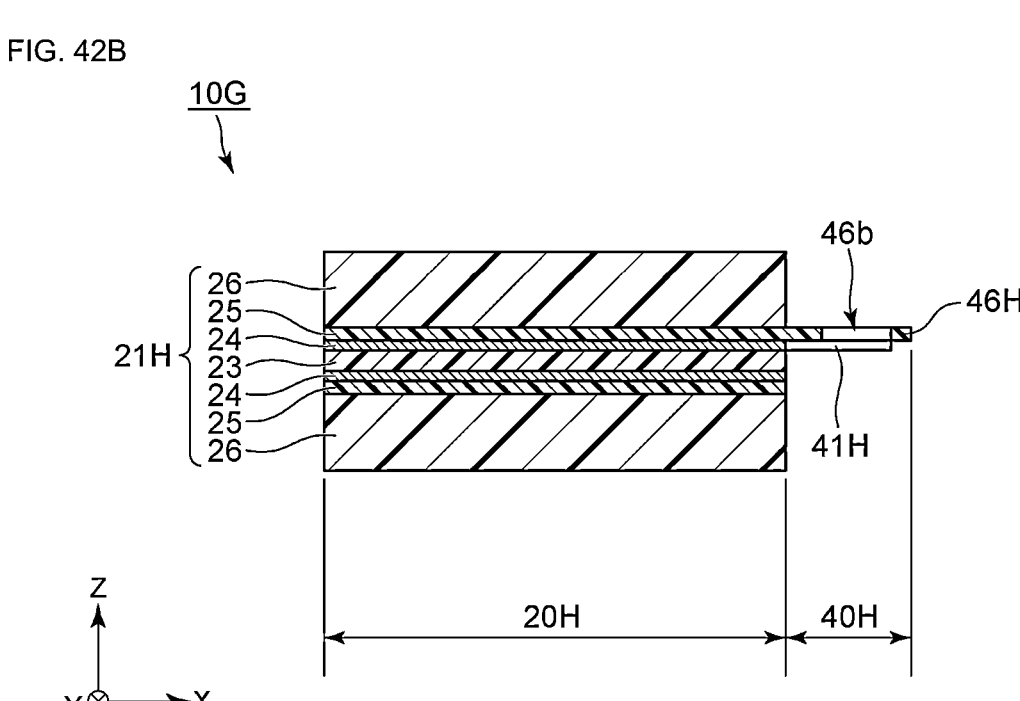
FIG. 42B is a schematic cross-sectional view of the oral appliance of FIG. 42A taken along line B-B.

The oral appliance 10H will be described with reference to FIG. 42A and FIG. 42B. FIG. 42A is a schematic bottom view of an exemplary aspect of the oral appliance 10H of Embodiment 8. FIG. 42B is a schematic cross-sectional view of the oral appliance 10H of FIG. 42A taken along line B-B. As illustrated in FIG. 42A and FIG. 42B, the oral appliance 10H includes a functional portion 20H and a connection portion 40H.

In the exemplary aspect, the functional portion 20H includes a sensor unit 21H that detects information related to the occlusal force of the user. The sensor unit 21H is a portion bitten by the teeth of the user when the occlusal force is measured. The sensor unit 21H includes the insulating layer 23, the electrode 24, the weight distribution plate 25, and the pressure receiving portion 26. Since the insulating layer 23, the electrode 24, the weight distribution plate 25, and the pressure receiving portion 26 are the same as those in Embodiment 7, the description thereof will be omitted.

The connection portion 40H is a portion that is detachably attached to the attachment/detachment operation unit 70H of the oral body device 50H, and is provided on the rear end side opposite to a front end of the oral appliance 10H. The connection portion 40H includes an engaging portion 46H and a plurality of electrical connection portions 41H. The engaging portion 46H is formed of a plate-shaped member. The plurality of electrical connection portions 41H is formed of electrodes, for example. In addition, each of the plurality of electrical connection portions 41H is arranged on the inner surface side of the engaging portion 46H. The inner surface side of the engaging portion 46H is a surface on the side where the insulating layer 23 is arranged in the thickness direction (Z direction) of the oral appliance 10H. In Embodiment 8, three electrical connection portions 41H are arranged in the engaging portion 46H. Note that the number of the electrical connection portions 41H is not limited to three, and can be one or plural.

In Embodiment 8, the engaging portion 46H is formed by a part of the weight distribution plate 25, and the electrical connection portion 41H is formed by a part of the electrode 24. Specifically, the engaging portion 46H is formed by causing one end of the weight distribution plate 25 to protrude from the insulating layer 23 and the pressure receiving portion 26. The electrical connection portion 41H is formed by causing one end of the electrode 24 to protrude from the insulating layer 23 and the pressure receiving portion 26.

In the connection portion 40H, the engaging portion 46H is provided with a lock hole 46b penetrating in the thickness direction. The lock hole 46b is formed in a rectangular shape when viewed in the thickness direction of the oral appliance 10H. The lock hole 46b is a hole into which a protrusion 73f of the pressing member 73H of the attachment/detachment operation unit 70H described later is inserted. In Embodiment 8, two lock holes 46b are provided with a space in the engaging portion 46H. In addition, when viewed in the thickness direction of the oral appliance 10H, the plurality of electrical connection portions 41H is arranged between the two lock holes 46b.

In the connection portion 40H, the electrical connection portion 41H and an electrical connection conductor 71H of the oral body device 50H are electrically connected by physical contacting.

Returning to FIG. 41A and FIG. 41B, an exemplary aspect of the configuration of the oral body device 50H and the operation of the attachment/detachment operation unit 70H will be described.

As illustrated in FIG. 41A and FIG. 41B, the oral body device 50H includes the substrate 72H provided with a plurality of the electrical connection conductors 71H and the attachment/detachment operation unit 70H.

The substrate 72H is formed in a plate shape and is arranged inside a body portion 60H. One end of the substrate 72H is arranged on an opening 64H side provided at a front end of the body portion 60H. The opening 64H is a portion into which the connection portion 40H of the oral appliance 10H is inserted.

Figure 43:
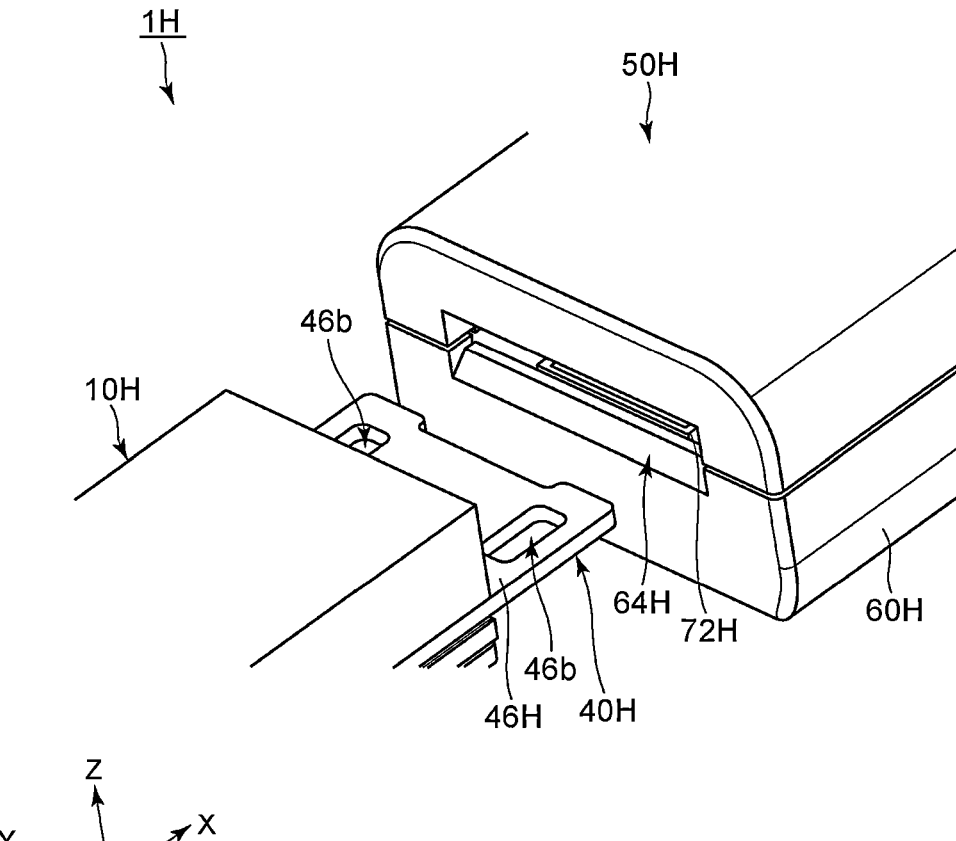
FIG. 43 is a schematic partial perspective view of an exemplary aspect of an oral body device of Embodiment 8.

FIG. 43 is a schematic partial perspective view of an exemplary aspect of the oral body device 50H of Embodiment 8. As illustrated in FIG. 43, the connection portion 40H of the oral appliance 10H is inserted into the opening 64H provided at a front end of the oral body device 50H. Thus, the oral appliance 10H is attached to the oral body device 50H.

Returning to FIG. 41A and FIG. 41B, the plurality of electrical connection conductors 71H is arranged on a front end side of the substrate 72H. To be specific, in the substrate 72H, the plurality of electrical connection conductors 71H is arranged on a main surface (one main surface) on a side on which the pressing member 73H described later is arranged. In Embodiment 8, three electrical connection conductors 71H are arranged on the substrate 72H. Note that the number of the electrical connection conductors 71H is not limited to three, and can be one or plural.

Figure 44:
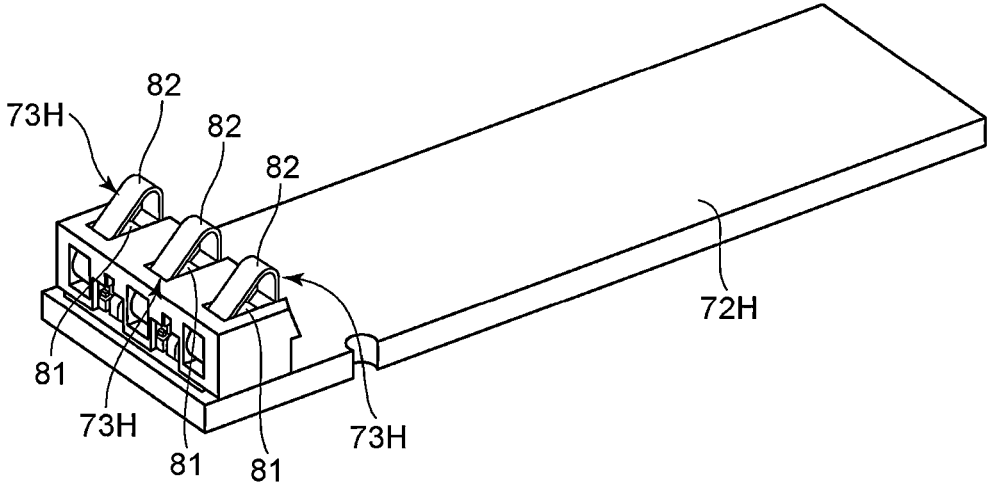
FIG. 44 is a schematic perspective view of an exemplary aspect of an electrical connection conductor provided on a substrate.
Figure 44:
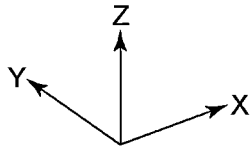

FIG. 44 is a schematic perspective view of an exemplary aspect of the plurality of electrical connection conductors 71H provided on the substrate 72H. As illustrated in FIG. 44, the plurality of electrical connection conductors 71H is formed by contact connectors. The contact connector is a connector that makes an electrical connection by physical contact. Specifically, each of the plurality of electrical connection conductors 71H has a connection terminal 81 and a movable component 82.

The connection terminal 81 only needs to be formed of a conductive material, and can be formed of, for example, the same material as the electrode 24.

The movable component 82 is a component that moves toward the connection terminal 81 and comes into contact with the connection terminal 81. Specifically, the movable component 82 moves toward the connection terminal 81 by being applied with a force, and comes into physical contact with the connection terminal 81. That is, the movable component 82 is not in physical contact with the connection terminal 81 in a state in which no force is applied. Meanwhile, in a state in which a force is applied, the movable component 82 moves toward the connection terminal 81 and comes into physical contact with the connection terminal 81.

The movable component 82 is formed of, for example, a conductive material. Therefore, when the movable component 82 comes into physical contact with the connection terminal 81, the movable component 82 and the connection terminal 81 are electrically connected to each other. The movable component 82 is formed of, for example, a plate spring.

In this exemplary aspect, the movable component 82 is in physical contact with the electrical connection portion 41H (electrode) of the connection portion 40H of the oral appliance 10H. Specifically, when the connection portion 40H of the oral appliance 10H is inserted into the opening 64H of the oral body device 50H, the electrical connection portion 41H of the connection portion 40H comes into contact with and presses against the movable component 82. By this pressing force, the movable component 82 moves toward the connection terminal 81.

When the movable component 82 comes into contact with the electrical connection portion 41H, the movable component 82 comes into physical contact with the connection terminal 81 by moving toward the connection terminal 81. As a result, the electrical connection portion 41H (electrode) of the oral appliance 10H, the movable component 82 and the connection terminal 81 are electrically connected.

Returning to FIG. 41A and FIG. 41B, the attachment/detachment operation unit 70H has the pressing member 73H. The pressing member 73H is a member configured to apply and release a force to the oral appliance 10H. The pressing member 73H is arranged on one main surface of the substrate 72H and configured to apply a force in a direction intersecting the main surface of the substrate 72H. To be specific, the attachment/detachment operation unit 70H includes one pressing member 73H arranged on one main surface of the substrate 72H. The pressing member 73H is configured to apply a force in a direction intersecting one main surface of the substrate 72H in a portion where the electrical connection conductor 71H is arranged. For purposes of this disclosure, the phrase "applying a force in a direction intersecting one main surface of the substrate 72H" means applying a force in a direction approaching the one main surface of the substrate 72H. The pressing member 73H fixes the oral appliance 10H to the oral body device 50H in a state in which the electrical connection portion 41H (electrode) of the oral appliance 10H and the electrical connection conductor 71H (connection terminal 81 and movable component 82) are in contact with each other.

The pressing member 73H is formed of a rod-shaped member having one end and the other end. The one end of the pressing member 73H is arranged on the opening 64H side, and the other end of the pressing member 73H is arranged inside the body portion 60H on the side opposite to the opening 64H.

The pressing member 73H has the protrusion 73f protruding toward one main surface of the substrate 72H. The protrusion 73f is provided at the one end of the pressing member 73H. In a state in which the connection portion 40H of the oral appliance 10H is attached to the oral body device 50H, the protrusion 73f is inserted into the lock hole 46b provided in the engaging portion 46H of the connection portion 40H and is engaged with the engaging portion 46H. As such, the oral appliance 10H is fixed to the oral body device 50H.

Figure 45:
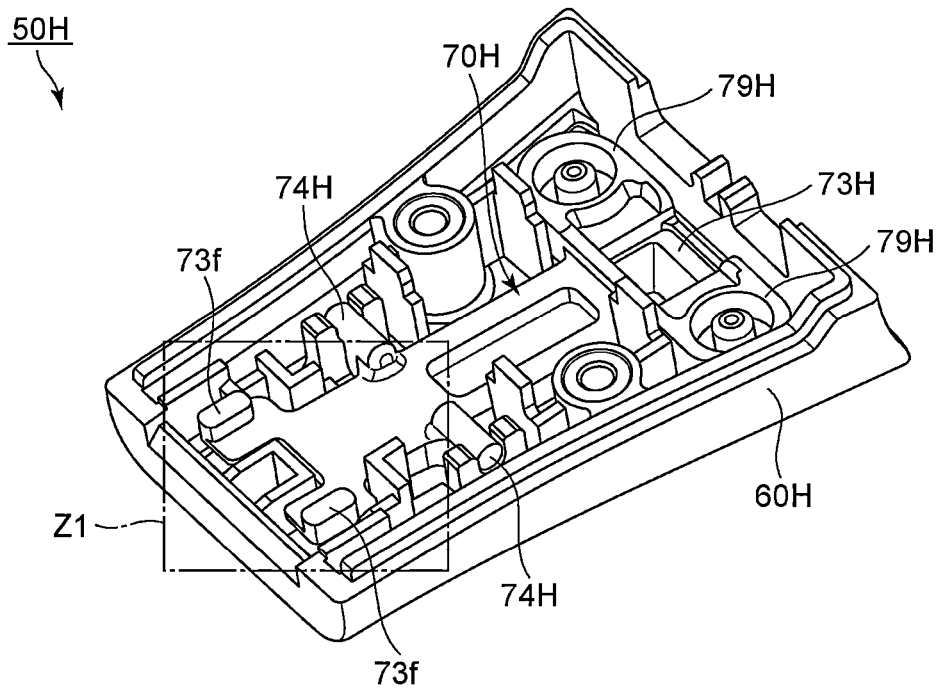
FIG. 45 is a schematic perspective view of an exemplary aspect of a pressing member.
Figure 45:
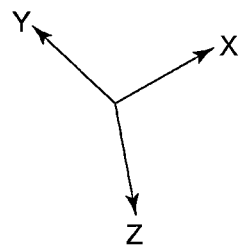
Figure 46:
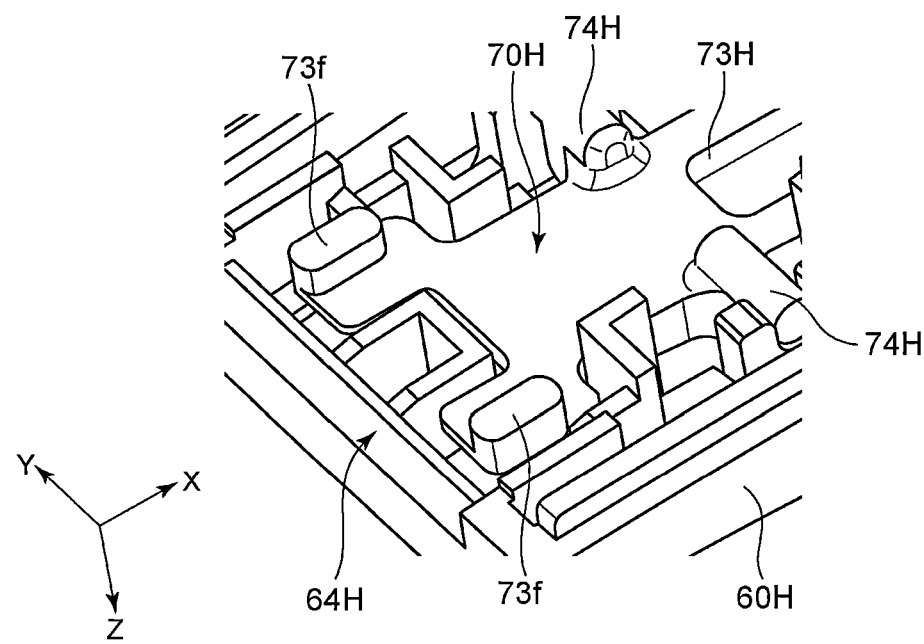
FIG. 46 is a schematic enlarged view of a Z1 portion of FIG. 45.
Figure 47:
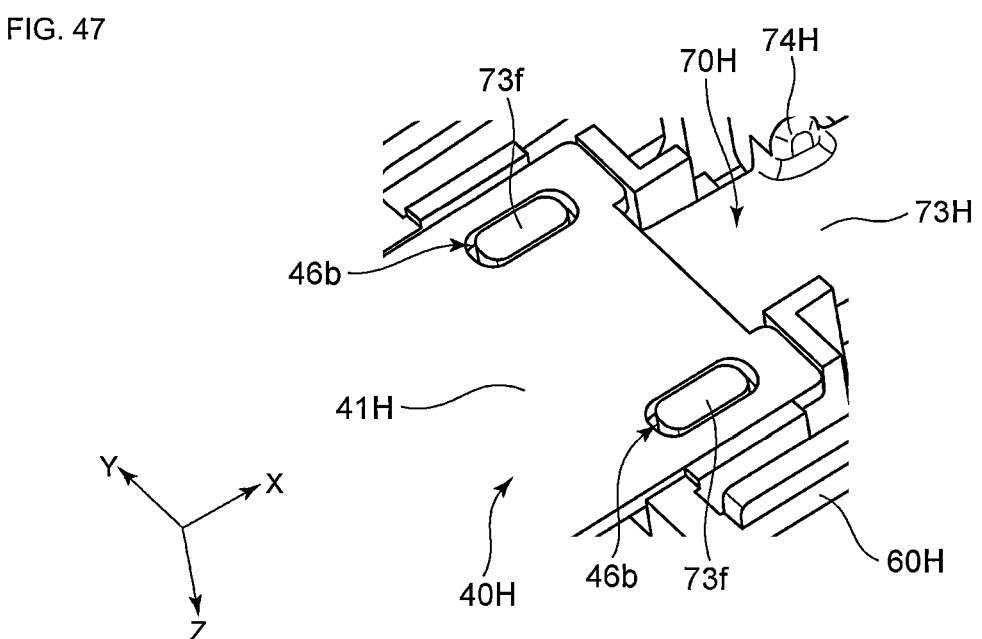
FIG. 47 is a schematic partial enlarged view illustrating a state in which the oral appliance is attached.

FIG. 45 is a schematic perspective view of an exemplary aspect of the pressing member 73H. FIG. 46 is a schematic enlarged view of a Z1 portion of FIG. 45. FIG. 47 is a schematic partial enlarged view illustrating a state in which the oral appliance 10H is attached. As illustrated in FIG. 45 and FIG. 46, two protrusions 73*f* are provided with a space on the one end side of the pressing member 73H. To be specific, the two protrusions 73*f* are arranged with a space in the Y direction. As illustrated in FIG. 46, when the connection portion 41H of the oral appliance 10H is attached to the oral body device 50H, the two protrusions 73*f* are inserted into the two lock holes 46*b* of the oral appliance 10H. Thus, the pressing member 73H fixes the oral appliance 10H to the oral body device 50H.

Returning to FIG. 41A and FIG. 41B, the pressing member 73H has an operation portion 79H. The operation portion 79H is provided on the other end side of the pressing member 73H and protrudes from an operation hole (not illustrated) provided in the body portion 60H. The user operates the operation portion 79H to thereby release the fixation of the oral appliance 10H to the oral body device 50H by the pressing member 73H.

Further, the pressing member 73H has a rotation shaft 74H and rotationally moves around the rotation shaft 74H. The rotation shaft 74H is provided between the one end and the other end of the pressing member 73H. When the other end side of the pressing member 73H moves in a direction away from the substrate 72H, the pressing member 73H rotationally moves around the rotation shaft 74H. Accordingly, the one end side of the pressing member 73H approaches the substrate 72H, whereas the other end side of the pressing member 73H moves away from the substrate 72H. In addition, when the operation portion is pressed in a direction approaching the substrate 72H, the pressing member 73H rotationally moves around the rotation shaft 74H, and the one end side of the pressing member 73H moves away from the substrate 72H while the other end side of the pressing member 73H approaches the substrate 72H.

Figure 48A:
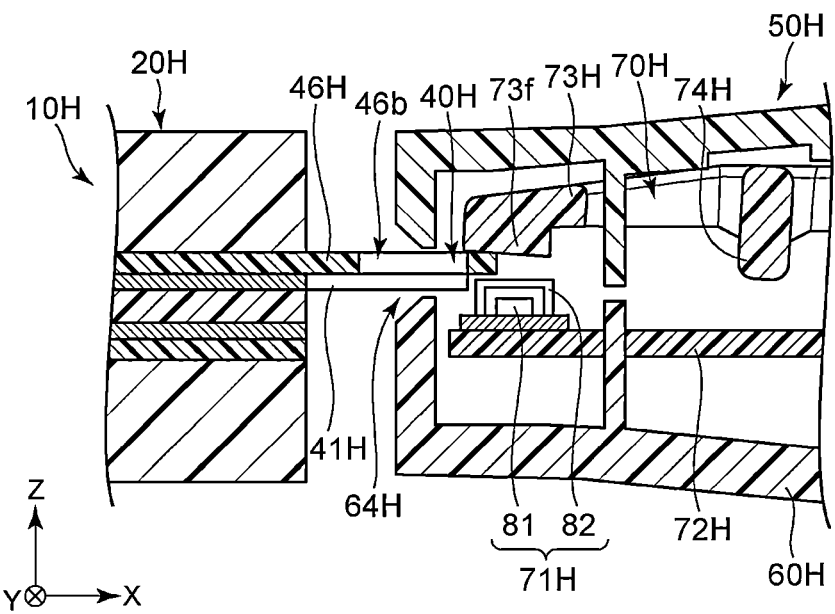
FIG. 48A is a schematic diagram illustrating an exemplary aspect of an operation of an attachment/detachment operation unit.
Figure 48B:
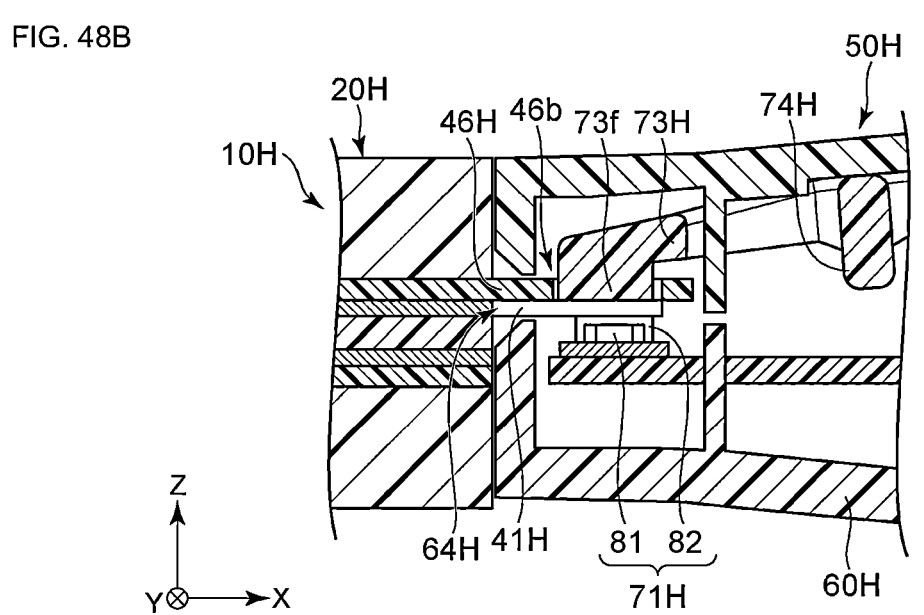
FIG. 48B is a schematic diagram illustrating an exemplary aspect of the operation of the attachment/detachment operation unit.

Next, an exemplary aspect of an operation of the attachment/detachment operation unit 70H will be described with reference to FIG. 48A and FIG. 48B. FIG. 48A and FIG. 48B are diagrams schematically illustrating an exemplary aspect of an operation of the attachment/detachment operation unit 70H.

As illustrated in FIG. 48A, when the connection portion 40H of the oral appliance 10H is inserted into inside the body portion 60H from the opening 64H of the oral body device 50H, the one end of the pressing member 73H comes into contact with the connection portion 40H. The one end of the pressing member 73H is lifted in a direction away from one main surface of the substrate 72H by insertion of the connection portion 40H. Note that in the state illustrated in FIG. 48A, in the electrical connection portion 41H, the movable component 82 is apart from and not in physical contact with the connection terminal 81.

As illustrated in FIG. 48B, when the connection portion 40H is arranged inside the body portion 60H, the electrical connection portion 41H (electrode) of the connection portion 40H comes into contact with the electrical connection conductor 71H. Specifically, the electrical connection portion 41H comes into contact with the movable component 82. When the movable component 82 comes into contact with the electrical connection portion 41H, the movable component 82 moves toward the connection terminal 81 and comes into physical contact with the connection terminal 81. As a result, the electrical connection portion 41H, the movable component 82, and the connection terminal 81 are electrically connected.

The pressing member 73H fixes the oral appliance 10H by applying a force in a direction intersecting one main surface of the substrate 72H in a state in which the electrical connection portion 41H (electrode), the movable component 82, and the connection terminal 81 are in contact with each other. Further, the protrusion 73*f* provided at the one end of the pressing member 73H is arranged in the lock hole 46*b* of the engaging portion 46H. Thus, the oral appliance 10H can be prevented from coming off from the oral body device 50H.

Note that when the oral appliance 10H is detached from the oral body device 50H, the fixation of the oral appliance 10H to the oral body device 50H by the pressing member 73H can be released by operating the operation portion 79H.

[Effects]

According to the oral body device 50H according to Embodiment 8, the following effects can be achieved.

In the oral body device 50H, the electrical connection conductor 71H has the connection terminal 81 provided on one main surface of the substrate 72H, and the movable component 82 that moves toward the connection terminal 81 and comes into contact with the connection terminal 81. When the movable component 82 comes into contact with the electrical connection portion 41H of the oral appliance 10H, the movable component 82 comes into contact with the connection terminal 81 by moving toward the connection terminal 81. The attachment/detachment operation unit 70H is arranged on one main surface of the substrate 72H, and has the pressing member 73H for applying a force in a direction intersecting the one main surface of the substrate 72H. The pressing member 73H fixes the oral appliance 10H by applying a force in a direction intersecting one main surface of the substrate 72H in a state in which the electrical connection portion 41H, the movable component 82, and the connection terminal 81 are in contact with each other. With such a configuration, attachment and detachment of the oral appliance 10H can be facilitated, and electrical connection between the oral appliance 10H and the oral body device 50H can be easily performed.

In addition, the oral body device 50H of Embodiment 8 easily maintains electrical connection with the oral appliance 10H as compared to Embodiment 7. In the oral body device 50H, electrical connection is realized by physical contact between the electrical connection portion 41H and the electrical connection conductor 71H (connection terminal 81 and movable component 82) only on one main surface side of the substrate 72H. Therefore, for example, when the occlusal force is measured, even in a case where a force in a rotation direction (twisting force) is generated in the oral appliance 10H, it is easy to maintain the physical contact between the electrical connection portion 41H and the electrical connection conductor 71H, so that the electrical connection is not easily released.

In addition, the oral appliance 10H is easily attached to and detached from the oral body device 50H of Embodiment 8 as compared to Embodiment 7. In the oral body device 50H, since the oral appliance 10H is fixed by the pressing member 73H only on one main surface side of the substrate 72H, it is not necessary to provide the guide 64*a* in the opening 64H as in Embodiment 7. Therefore, it is not necessary to attach or detach the oral appliance 10H along the guide 64*a*.

In addition, in the oral body device 50H of Embodiment 8, the number of components can be reduced as compared to Embodiment 7, and thus the manufacturing cost can be reduced.

In addition, in the oral body device 50H of Embodiment 8, it is easy to distinguish the front surface and the back surface due to the shape.

In general, it noted that although the present invention has been fully described in connection with the exemplary embodiments with reference to the accompanying drawings, various changes and modifications will become apparent to those skilled in the art. It is to be understood that such changes and modifications are intended to be included within the scope of the present invention as defined by the appended claims unless departing therefrom.

REFERENCE SIGNS LIST 1A, 1B, 1C, 1D, 1E, 1F, 1G, 1H ORAL DEVICE
10, 10A, 10C, 10CA, 10CB, 10D, 10E, 10EA, 10EB, 10F, 10G, 10H ORAL APPLIANCE
11 WIRING LAYER
12 FIRST INSULATING LAYER
13 SECOND INSULATING LAYER
14 RESIN FILM
15 HEAT INSULATING MATERIAL
16 INSULATING LAYER
20, 20E, 20EA, 20EB, 20G, 20H FUNCTIONAL POR-
TION
21, 21H, 21G SENSOR UNIT
21a SENSOR SURFACE
22, 22a, 22b ENERGY IRRADIATION UNIT
23 INSULATING LAYER
24 ELECTRODE
25 WEIGHT DISTRIBUTION PLATE
26 PRESSURE RECEIVING PORTION
30 WIRING PORTION
31 WIRING
32 PROTECTIVE LAYER
40, 40A, 40E, 40F, 40G, 40H CONNECTION PORTION
41, 41G, 41H ELECTRODE (ELECTRICAL CONNEC-
TION PORTION)
42 MOUNTING HOLE
43 RFID TAG (ELECTRICAL CONNECTION POR-
TION)
44 ANTENNA
45 IC CHIP
46, 46H ENGAGING PORTION
46a, 46b LOCK HOLE
50, 50B, 50C, 50D, 50E, 50F, 50G, 50H ORAL BODY
DEVICE
60, 60C, 60D, 60G, 60H BODY PORTION
61, 61C, 61D GRIP PORTION
62 CONTROL UNIT
63 CALCULATION UNIT
64, 64H OPENING
65 OPERATION HOLE
70, 70A, 70AA, 70AB, 70AC, 70B, 70BA, 70BB, 70C,
70CA, 70CB, 70D, 70DA,
70DB, 70F, 70G, 70H ATTACHMENT/DETACHMENT
OPERATION UNIT
71, 71G, 71H CONNECTION TERMINAL (ELECTRI-
CAL CONNECTION CONDUCTOR)
72, 72C, 72CA, 72CB, 72D, 72DA, 72DB, 72GA, 72GB
ARRANGEMENT SURFACE
72G, 72H SUBSTRATE
72a POSITIONING MEMBER
72aa BOTTOM SURFACE
72ab, 72ac, 72ad, 72ae INCLINED SURFACE
73, 73A, 73AA, 73B, 73BA, 73BB, 73C, 73CA, 73CB,
73D, 73DA, 73DB, 73G,
73H PRESSING MEMBER
73a, 73b PROTRUSION
73c CONTACT SURFACE
73ca BOTTOM SURFACE
73cb, 73cc INCLINED SURFACE

73cd, 73ci SEMI-CIRCULAR SURFACE
73ce, 73cf INCLINED SURFACE
73cg, 73ch SEMI-CIRCULAR SURFACE
73d SLIDE GROOVE
73e, 73f PROTRUSION
74, 74G, 74H ROTATION SHAFT
75, 75B, 75BA, 75BB DETECTION UNIT
76a LIGHT EMITTING PORTION
76b LIGHT RECEIVING PORTION
77 RING-SHAPED MEMBER
78 ANTENNA (ELECTRICAL CONNECTION CON-
DUCTOR)
79, 79H OPERATION PORTION
80, 80C GUARD
81 CONNECTION TERMINAL
82 MOVABLE COMPONENT
90 DISPLAY UNIT
91 INPUT UNIT

The invention claimed is:

1. An oral body device that is attachable to an oral appliance having an electrical connection portion, the oral body device comprising:
    a body; and
    an attachment/detachment operation unit that has an elec-
        trical connection conductor and is structurally config-
        ured to detachably attach the oral appliance to the body,
    wherein the attachment/detachment operation unit is con-
        figured to fixedly attach the oral appliance in a state in
        which the electrical connection portion of the oral
        appliance is electrically connected to the electrical
        connection conductor by applying a force to the oral
        appliance,
    wherein the attachment/detachment operation unit is con-
        figured to release fixation and detach the oral appliance
        by releasing the force applied to the oral appliance,
    wherein the attachment/detachment operation unit
        includes an arrangement surface on which the oral
        appliance is arranged, and a pressing member config-
        ured to apply a force in a direction intersecting the
        arrangement surface,
    wherein the pressing member has a contact surface that
        comes into contact with the oral appliance, and the
        pressing member is configured to be slidable in an
        oblique direction with respect to the arrangement sur-
        face, and
    wherein the pressing member includes a protrusion that
        protrudes from the contact surface toward the arrange-
        ment surface.

2. The oral body device according to claim 1, wherein the attachment/detachment operation unit is configured to detachably attach the oral appliance to the body by operating application and release of force to the attachment/detach-ment operation unit.

3. The oral body device according to claim 1,
    wherein the pressing member includes a first end disposed
        on the arrangement surface side and a second end
        disposed on a side opposite to the first end, and
    wherein the pressing member is configured to be rotatable
        around a rotation shaft disposed between the first end
        and the second end.

4. The oral body device according to claim 3, wherein the pressing member includes a protrusion that protrudes toward the arrangement surface between the first end and the rotation shaft.

5. The oral body device according to claim 1,
wherein the pressing member includes a first end disposed on the arrangement surface side and a second end disposed on a side opposite to the first end, and
wherein the pressing member is configured to bring the contact surface into contact with the oral appliance by sliding in a first oblique direction from the first end towards the second end, and further configured to release contact between the contact surface and the oral appliance while pushing out the oral appliance by sliding in a second oblique direction opposite to the first oblique direction.

6. The oral body device according to claim 1, further comprising a protrusion disposed on the arrangement surface and that protrudes towards the pressing member.

7. The oral body device according to claim 1, further comprising:
a detection unit configured to detect whether the oral appliance is attached to the attachment/detachment operation unit; and
a control unit configured to determine an operational state of the oral appliance based on a detection result of the detection unit,
wherein the control unit is configured to:
determine whether the oral appliance attached to the attachment/detachment operation unit has been used,
determine that the operational state of the oral appliance is not possible when the oral appliance is determined to have been used, and
after the operational state of the oral appliance is determined to be not possible, determine that the operational state of the oral appliance is possible when the detection unit detects that a used oral appliance has been detached and replaced with an unused oral appliance that has been attached.

8. The oral body device according to claim 7, further comprising a display unit configured to display information on the operational state of the oral appliance.

9. The oral body device according to claim 7, wherein, when the oral appliance is determined to have been used, the control unit is configured to:
stop use of the oral appliance, and
enable use of the oral appliance based on a determination that the operational state of the oral appliance is possible.

10. The oral body device according to claim 1, wherein the body includes:
a grip configured to be gripped by a user, and
a guard configured to protect the grip.

11. The oral body device according to claim 1,
wherein the electrical connection portion of the oral appliance is an RFID tag,
wherein the electrical connection conductor of the oral body device is an antenna, and
wherein the attachment/detachment operation unit is configured to electrically connect the RFID tag to the antenna by wirelessly connecting the RFID tag and antenna.

12. The oral body device according to claim 1, further comprising a calculation unit configured to calculate an amount of moisture based on information acquired by the oral appliance.

13. The oral body device according to claim 1,
wherein the electrical connection portion of the oral appliance includes a plurality of electrodes, wherein the electrical connection conductor includes a plurality of connection terminals disposed on both main surfaces of a substrate,
wherein the attachment/detachment operation unit includes a plurality of pressing members that are respectively arranged on both main surfaces of the substrate and configured to apply a force in a direction that intersects both the main surfaces of the substrate, and
wherein the plurality of pressing members is configured to fix the oral appliance by applying a force in a direction that intersects both main surfaces of the substrate in a state in which the plurality of electrodes and the plurality of connection terminals are respectively in contact with each other.

14. The oral body device according to claim 13, wherein the plurality of pressing members each has a protrusion that protrudes towards both main surfaces of the substrate.

15. The oral body device according to claim 1,
wherein the electrical connection portion of the oral appliance is at least one electrode,
wherein the electrical connection conductor of the oral body device is at least one connection terminal, and
wherein the attachment/detachment operation unit is configured to electrically connect the at least one electrode to the at least one connection terminal by bringing the at least one electrode into physical contact with the at least one connection terminal.

16. An oral body device that is attachable to an oral appliance having an electrical connection portion, the oral body device comprising:
a body; and
an attachment/detachment operation unit that has an electrical connection conductor and is structurally configured to detachably attach the oral appliance to the body,
wherein the attachment/detachment operation unit is configured to fixedly attach the oral appliance in a state in which the electrical connection portion of the oral appliance is electrically connected to the electrical connection conductor by applying a force to the oral appliance, and
wherein the attachment/detachment operation unit is configured to release fixation and detach the oral appliance by releasing the force applied to the oral appliance,
wherein the attachment/detachment operation unit includes an arrangement surface on which the oral appliance is arranged, and a pressing member configured to apply a force in a direction intersecting the arrangement surface,
wherein the arrangement surface is curved in a concave shape or a convex shape, and
wherein the pressing member is curved in a concave shape or a convex shape along a shape of the arrangement surface.

17. An oral body device that is attachable to an oral appliance having an electrical connection portion, the oral body device comprising:
a body; and
an attachment/detachment operation unit that has an electrical connection conductor and is structurally configured to detachably attach the oral appliance to the body,
wherein the attachment/detachment operation unit is configured to fixedly attach the oral appliance in a state in which the electrical connection portion of the oral appliance is electrically connected to the electrical connection conductor by applying a force to the oral appliance, wherein the attachment/detachment operation unit is configured to release fixation and detach the oral appliance by releasing the force applied to the oral appliance, wherein the electrical connection conductor includes:

a connection terminal disposed on a first main surface of a substrate; and a movable component configured to move towards the connection terminal to come into contact with the connection terminal, wherein the movable component is configured to contact the connection terminal by moving toward the connection terminal when contacting the electrical connection portion of the oral appliance, wherein the attachment/detachment operation unit includes a pressing member that is arranged on one main surface of the substrate and is configured to apply a force in a direction that intersects the first main surface of the substrate, and wherein the pressing member is configured to fix the oral appliance by applying a force in a direction that intersects the first main surface of the substrate in a state in which the electrical connection portion, the movable component, and the connection terminal are in contact with each other.

18. The oral body device according to claim 17, wherein:

the attachment/detachment operation unit includes an arrangement surface on which the oral appliance is arranged, the arrangement surface is curved in a concave shape or a convex shape, and the pressing member is curved in a concave shape or a convex shape along a shape of the arrangement surface.

\*　\*　\*　\*　\*